(12) United States Patent
Altenbach et al.

(10) Patent No.: US 10,138,227 B2
(45) Date of Patent: Nov. 27, 2018

(54) HETEROARYL SUBSTITUTED PYRIDINES AND METHODS OF USE

(71) Applicants: AbbVie S.à.r.l., Luxembourg (LU); Galapagos NV, Mechelen (BE)

(72) Inventors: Robert J. Altenbach, Chicago, IL (US); Andrew Bogdan, Evanston, IL (US); Ghjuvanni Petru Diunisu Coti, Mechelen (BE); Marlon D. Cowart, Round Lake Bach, IL (US); Stephen N Greszler, Vernon Hills, IL (US); Hans Kelgtermans, Mechelen (BE); Philip R Kym, Libertyville, IL (US); Steven Emiel Van der Plas, Mechelen (BE); Xueqing Wang, Northbrook, IL (US)

(73) Assignees: AbbVie S.á.r.l., Luxembourg (LU); Galapagos NV, Mechelen (BE)

(*) Notice: Subject to any disclaimer, the term of this patent is extended or adjusted under 35 U.S.C. 154(b) by 0 days.

(21) Appl. No.: 15/602,892

(22) Filed: May 23, 2017

(65) Prior Publication Data

US 2017/0349576 A1     Dec. 7, 2017

Related U.S. Application Data

(60) Provisional application No. 62/345,315, filed on Jun. 3, 2016.

(51) Int. Cl.

| C07D 413/04 | (2006.01) |
|---|---|
| C07D 417/04 | (2006.01) |
| C07D 413/14 | (2006.01) |
| A61K 45/06 | (2006.01) |
| A61K 31/444 | (2006.01) |
| C07D 417/14 | (2006.01) |
| A61K 31/4439 | (2006.01) |

(52) U.S. Cl.
CPC .......... *C07D 413/04* (2013.01); *A61K 31/444* (2013.01); *A61K 31/4439* (2013.01); *A61K 45/06* (2013.01); *C07D 413/14* (2013.01); *C07D 417/04* (2013.01); *C07D 417/14* (2013.01)

(58) Field of Classification Search
CPC .. C07D 413/04; C07D 413/14; C07D 417/04; C07D 417/14; A61K 31/4439; A61K 31/444; A61K 45/06
USPC ....................................................... 514/333
See application file for complete search history.

(56) References Cited

U.S. PATENT DOCUMENTS

| 8,999,976 B2 | 4/2015 | Binch et al. |
| 9,133,210 B2 | 9/2015 | Van Der Plas et al. |
| 9,382,254 B2 | 7/2016 | De Blieck et al. |
| 9,567,322 B2 | 2/2017 | Kym et al. |
| 9,642,831 B2 | 5/2017 | Altenbach et al. |
| 2016/0355480 A1 | 12/2016 | Altenbach et al. |
| 2017/0015675 A1 | 1/2017 | Altenbach et al. |
| 2017/0101405 A1 | 4/2017 | Akkari et al. |
| 2017/0101406 A1 | 4/2017 | Akkari et al. |

FOREIGN PATENT DOCUMENTS

| WO | 2005120497 A2 | 12/2005 |
| WO | 2006002421 A2 | 1/2006 |
| WO | 2008147952 A1 | 12/2008 |
| WO | 2009074575 A2 | 6/2009 |
| WO | 2009076593 A1 | 6/2009 |
| WO | 2010048573 A1 | 4/2010 |
| WO | 2011072241 A1 | 6/2011 |
| WO | 2011113894 A1 | 9/2011 |
| WO | 2012048181 A1 | 4/2012 |
| WO | 2013038373 A1 | 3/2013 |
| WO | 2013038378 A1 | 3/2013 |
| WO | 2013038381 A1 | 3/2013 |
| WO | 2013038386 A1 | 3/2013 |
| WO | 2013038390 A1 | 3/2013 |
| WO | 2013043720 A1 | 3/2013 |
| WO | 2015138909 A1 | 9/2015 |
| WO | 2015138934 A1 | 9/2015 |

OTHER PUBLICATIONS

Quinton, P.M., 1990. Cystic fibrosis: a disease in electrolyte transport. FASEB J. 4, 2709-2717.

Kerem, B., Rommens, J.M., Buchanan, J.A., Markiewicz, D., Cox, T.K., Chakravarti, A., Buchwald, M., Tsui, L.C., 1989. Identification of the cystic fibrosis gene: genetic analysis. Science 245, 1073-1080.

Bobadilla, J.L., Macek, M., Jr, Fine, J.P., Farrell, P.M., 2002. Cystic fibrosis: a worldwide analysis of CFTR mutations—correlation with incidence data and application to screening. Hum. Mutat. 19, 575-606. doi:10.1002/humu.10041.

Pasyk, E.A., Foskett, J.K., 1995. Mutant (ΔF508) Cystic Fibrosis Transmembrane Conductance Regulator CI—Channel is Functional When Retained in Endoplasmic Reticulum of Mammalian Cells. J. Biol. Chem. 270, 12347-12350.

Morello, J.-P., Bouvier, M., Petaja-Repo, U.E., Bichet, D.G., 2000. Pharmacological chaperones: a new twist on receptor folding. Trends Pharmacol. Sci. 21, 466-469. doi:10.1016/S0165-6147(00)01575-3.

(Continued)

*Primary Examiner* — Daniel R Carcanague
(74) *Attorney, Agent, or Firm* — Quarles & Brady LLP

(57) ABSTRACT

The invention discloses compounds of Formula I,

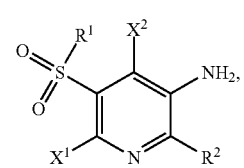

I wherein $X^1$, $X^2$, $R^1$, and $R^2$ are as defined herein. The present invention relates to compounds and their use in the treatment of cystic fibrosis, methods for their production, pharmaceutical compositions comprising the same, and methods of treating cystic fibrosis by administering a compound of the invention.

29 Claims, No Drawings

(56) References Cited

OTHER PUBLICATIONS

Shastry, B.S., 2003. Neurodegenerative disorders of protein aggregation. Neurochem. Int. 43, 1-7. doi:10.1016/S0197-0186(02)00196-1.
Zhang, W., Fujii, N., Naren, A.P., 2012. Recent advances and new perspectives in targeting CFTR for therapy of cystic Fibrosis and enterotoxin-induced secretory diarrheas. Future Med. Chem. 4, 329-345. doi:10.4155/fmc.12.1.
IUPAC 1974 Recommendations for Section E, Fundamental Stereochemistry, in Pure Appl. Chem., 1976, 45: 13-30.
Berge, S.M. et al., 1977, Pharmaceutical Salts, J. Pharmaceutical Sciences, 66: 1-19.
Galietta, L.J.V., Haggle, P.M., Verkman, A.S., 2001. Green fluorescent protein-based halide indicators with improved chloride and iodide affinities. FEBS Lett. 499, 220-224. doi:10.1016/S0014-5793(01)02561-3.
Nagai, T. Ibata, K. Park, E.S., Kubota, M., Mikoshiba, K., Miyawaki, A., 2002. A variant of yellow fluorescent protein with fast and efficient maturation for cell-biological applications. Nat. Biotechnol. 20, 87-90. doi:10.1038/nbt0102-87.
Fulcher, M.L, Gabriel, S., Burns, K.A., Yankaskas, J.R., Randell, S.H., 2005. Well-differentiated human airway epithelial cell cultures. Methods Mol. Med. 107, 183-206.
Rowe, S.M., Verkman, A.S., 2013. Cystic Fibrosis Transmembrane Regulator Correctors and Potentiators. Cold Spring Harb. Perspect. Med. 3, a009761. doi:10.1101/cshperspect.a009761.

HETEROARYL SUBSTITUTED PYRIDINES AND METHODS OF USE

CROSS REFERENCE TO RELATED APPLICATIONS

This application claims priority to U.S. Provisional Application No. 62/345,315, filed Jun. 3, 2016, which is incorporated herein by its entirety for all purposes.

The inventions claimed herein were made by or on behalf of AbbVie S.à.r.l., Luxembourg (LU) and Galapagos NV, Mechelen (BE), who are parties to a joint research agreement that was in effect on or before the date the claimed invention was made. The claimed invention was made as the result of activities undertaken within the scope of the joint research agreement.

BACKGROUND OF THE INVENTION

Technical Field

The invention relates to substituted pyridine compounds that are modulators of the Cystic Fibrosis Transmembrane Conductance Regulator (CFTR) protein, useful in treating diseases and conditions mediated and modulated by CFTR. The invention also relates to compositions containing compounds of the invention, processes for their preparation, and methods of treatment using them.

Description of Related Technology

ABC transporters are a family of homologous membrane transporter proteins regulating the transport of a wide variety of pharmacological agents (for example drugs, xenobiotics, anions, etc.) that bind and use cellular adenosine triphosphate (ATP) for their specific activities. Some of these transporters were found to defend malignant cancer cells against chemotherapeutic agents, acting as multidrug resistance proteins (like the MDR1-P glycoprotein, or the multidrug resistance protein, MRP 1). So far, 48 ABC transporters, grouped into 7 families based on their sequence identity and function, have been identified.

ABC transporters provide protection against harmful environmental compounds by regulating a variety of important physiological roles within the body, and therefore represent important potential drug targets for the treatment of diseases associated with transporter defects, outwards cell drug transport, and other diseases in which modulation of ABC transporter activity may be beneficial.

The cAMP/ATP-mediated anion channel, CFTR, is one member of the ABC transporter family commonly associated with diseases, which is expressed in a variety of cell types, including absorptive and secretory epithelia cells, where it regulates anion flux across the membrane, as well as the activity of other ion channels and proteins. The activity of CFTR in epithelial cells is essential for the maintenance of electrolyte transport throughout the body, including respiratory and digestive tissue (Quinton, P. M., 1990. Cystic fibrosis: a disease in electrolyte transport. FASEB J. 4, 2709-2717).

The gene encoding CFTR has been identified and sequenced (Kerem, B., Rommens, J. M., Buchanan, J. A., Markiewicz, D., Cox, T. K., Chakravarti, A., Buchwald, M., Tsui, L. C., 1989. Identification of the cystic fibrosis gene: genetic analysis. Science 245, 1073-1080). CFTR comprises about 1480 amino acids that encode a protein made up of a tandem repeat of transmembrane domains, each containing six transmembrane helices and a nucleotide binding domain. The pair of transmembrane domains is linked by a large, polar, regulatory (R)-domain with multiple phosphorylation sites that regulate channel activity and cellular trafficking.

Cystic fibrosis (CF) is caused by a defect in this gene which induces mutations in CFTR. Cystic fibrosis is the most common fatal genetic disease in humans, and affects ~0.04% of white individuals (Bobadilla, J. L., Macek, M., Jr, Fine, J. P., Farrell, P. M., 2002. Cystic fibrosis: a worldwide analysis of CFTR mutations—correlation with incidence data and application to screening. Hum. Mutat. 19, 575-606. doi:10.1002/humu.10041), for example, in the United States, about one in every 2,500 infants is affected, and up to 10 million people carry a single copy of the defective gene without apparent ill effects; moreover subjects bearing a single copy of the gene exhibit increased resistance to cholera and to dehydration resulting from diarrhea. This effect might explain the relatively high frequency of the CF gene within the population.

In contrast, individuals with two copies of the CF associated gene suffer from the debilitating and fatal effects of CF, including chronic lung infections.

In cystic fibrosis patients, mutations in endogenous respiratory epithelial CFTR fails to confer chloride and bicarbonate permeability to epithelial cells in lung and other tissues, thus leading to reduced apical anion secretion and disruptions of the ion and fluid transport. This decrease in anion transport causes an enhanced mucus and pathogenic agent accumulation in the lung triggering microbial infections that ultimately cause death in CF patients.

Beyond respiratory disease, CF patients also suffer from gastrointestinal problems and pancreatic insufficiency that result in death if left untreated. Furthermore, female subjects with cystic fibrosis suffer from decreased fertility, whilst males with cystic fibrosis are infertile.

A variety of disease causing mutations has been identified through sequence analysis of the CFTR gene of CF chromosomes (Kerem, B., Rommens, J. M., Buchanan, J. A., Markiewicz, D., Cox, T. K., Chakravarti, A., Buchwald, M., Tsui, L. C., 1989. Identification of the cystic fibrosis gene: genetic analysis. Science 245, 1073-1080). ΔF508-CFTR, the most common CF mutation (present in at least 1 allele in ~90% of CF patients) and occurring in approximately 70% of the cases of cystic fibrosis, contains a single amino acid deletion of phenylalanine 508. This deletion prevents the nascent protein from folding correctly, which protein in turn cannot exit the endoplasmic reticulum (ER) and traffic to the plasma membrane, and then is rapidly degraded. As a result, the number of channels present in the membrane is far less than in cells expressing wild-type CFTR. In addition to impaired trafficking, the mutation results in defective channel gating. Indeed, even if ΔF508-CFTR is allowed to reach the cell plasma membrane by low-temperature (27° C.) rescue where it can function as a cAMP-activated chloride channel, its activity is decreased significantly compared with WT-CFTR (Pasyk, E. A., Foskett, J. K., 1995. Mutant (ΔF508) Cystic Fibrosis Transmembrane Conductance Regulator Cl⁻ Channel Is Functional When Retained in Endoplasmic Reticulum of Mammalian Cells. J. Biol. Chem. 270, 12347-12350).

Other mutations with lower incidence have also been identified that alter the channel regulation or the channel conductance. In case of the channel regulation mutants, the mutated protein is properly trafficked and localized to the plasma membrane but either cannot be activated or cannot function as a chloride channel (e.g. missense mutations located within the nucleotide binding domains), examples of these mutations are G551D, G178R, and G1349D. Mutations affecting chloride conductance have a CFTR protein that is correctly trafficked to the cell membrane but that generates reduced chloride flow (e.g. missense mutations located within the membrane-spanning domain), examples of these mutations are R117H and R334W.

In addition to cystic fibrosis, CFTR activity modulation may be beneficial for other diseases not directly caused by mutations in CFTR, such as, for example, chronic obstructive pulmonary disease (COPD), dry eye disease, and Sjögren's syndrome.

COPD is characterized by a progressive and non-reversible airflow limitation, which is due to mucus hypersecretion, bronchiolitis, and emphysema. A potential treatment of mucus hypersecretion and impaired mucociliary clearance that is common in COPD could consist in using activators of mutant or wild-type CFTR. In particular, the anion secretion increase across CFTR may facilitate fluid transport into the airway surface liquid to hydrate the mucus and optimize periciliary fluid viscosity. The resulting enhanced mucociliary clearance would help in reducing the symptoms associated with COPD.

Dry eye disease is characterized by a decrease in tear production and abnormal tear film lipid, protein and mucin profiles. Many factors may cause dry eye disease, some of which include age, arthritis, Lasik eye surgery, chemical/thermal burns, medications, allergies, and diseases, such as cystic fibrosis and Sjögren's syndrome. Increasing anion secretion via CFTR could enhance fluid transport from the corneal endothelial cells and secretory glands surrounding the eye, and eventually improve corneal hydration, thus helping to alleviate dry eye disease associated symptoms. Sjögren's syndrome is an autoimmune disease where the immune system harms moisture-producing glands throughout the body, including the eye, mouth, skin, respiratory tissue, liver, vagina, and gut. The ensuing symptoms, include, dry eye, mouth, and vagina, as well as lung disease. Sjögren's syndrome is also associated with rheumatoid arthritis, systemic lupus, systemic sclerosis, and polymyositis/dermatomyositis. The cause of the disease is believed to lie in defective protein trafficking, for which treatment options are limited. As a consequence, modulation of CFTR activity may help hydrating the various organs and help to elevate the associated symptoms.

In addition to CF, the defective protein trafficking induced by the ΔF508-CFTR has been shown to be the underlying basis for a wide range of other diseases, in particular diseases where the defective functioning of the endoplasmic reticulum (ER) may either prevent the CFTR protein to exit the EP, and/or the misfolded protein is degraded (Morello, J.-P., Bouvier, M., Petäjä-Repo, U. E., Bichet, D. G., 2000. Pharmacological chaperones: a new twist on receptor folding. Trends Pharmacol. Sci. 21, 466-469. doi:10.1016/S0165-6147(00)01575-3; Shastry, B. S., 2003. Neurodegenerative disorders of protein aggregation. Neurochem. Int. 43, 1-7. doi:10.1016/S0197-0186(02)00196-1; Zhang, W., Fujii, N., Naren, A. P., 2012. Recent advances and new perspectives in targeting CFTR for therapy of cystic fibrosis and enterotoxin-induced secretory diarrheas. Future Med. Chem. 4, 329-345. doi:10.4155/fmc.12.1).

A number of genetic diseases are associated with a defective ER processing equivalent to the defect observed with CFTR in CF such as glycanosis CDG type 1, hereditary emphysema (α-1-antitrypsin (PiZ variant)), congenital hyperthyroidism, osteogenesis imperfecta (Type I, II, or IV procollagen), hereditary hypofibrinogenemia (fibrinogen), ACT deficiency (α-1-antichymotrypsin), diabetes insipidus (DI), neurohypophyseal DI (vasopressin hormoneN2-receptor), nephrogenic DI (aquaporin II), Charcot-Marie Tooth syndrome (peripheral myelin protein 22), Pelizaeus-Merzbacher disease, neurodegenerative diseases such as Alzheimer's disease (APP and presenilins), Parkinson's disease, amyotrophic lateral sclerosis, progressive supranuclear palsy, Pick's disease, several polyglutamine neurological disorders such as Huntington's disease, spinocerebellar ataxia type I, spinal and bulbar muscular atrophy, dentatorubral pallidoluysian, and myotonic dystrophy, as well as spongiform encephalopathies, such as hereditary Creutzfeldt-Jakob disease (prion protein processing defect), Fabry disease (lysosomal α-galactosidase A), Straussler-Scheinker syndrome, chronic obstructive pulmonary disease (COPD), dry eye disease, and Sjögren's syndrome.

In addition to up-regulation of the activity of CFTR, anion secretion reduction by CFTR modulators may be beneficial for the treatment of secretory diarrheas, in which epithelial water transport is dramatically increased as a result of secretagogue activated chloride transport. The mechanism involves elevation of cAMP and stimulation of CFTR.

Regardless of the cause, excessive chloride transport is seen in all diarrheas, and results in dehydration, acidosis, impaired growth and death. Acute and chronic diarrheas remain a major medical problem worldwide, and are a significant factor in malnutrition, leading to death in children of less than five years old (5,000,000 deaths/year). Furthermore, in patients with chronic inflammatory bowel disease (IBD) and/or acquired immunodeficiency syndrome (AIDS), diarrhea is a dangerous condition.

Accordingly, there is a need for novel compounds able to modulate CFTR. In particular, the present invention discloses compounds that may act as CFTR modulators for the treatment of cystic fibrosis. The present invention also provides methods for the preparation of these compounds, pharmaceutical compositions comprising these compounds and methods for the treatment of cystic fibrosis by administering the compounds of the invention.

SUMMARY

In one aspect the invention provides for compounds of Formula I, and pharmaceutically acceptable salts thereof,

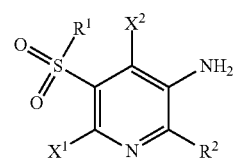

I wherein
$X^1$ and $X^2$ are independently selected
  H;
  halo;
  $C_{1-4}$ alkyl optionally substituted with one or more independently selected halo;
  $C_{1-4}$ alkoxy optionally substituted with one or more independently selected
    —OH;
    $C_{1-4}$ alkoxy; or
    —$NR^{8A}R^{8B}$;
  —$NR^{9A}R^{9B}$;
  cyclopropyl optionally substituted with one or more independently selected $R^5$ groups;
  phenoxy optionally substituted with one or more independently selected $R^5$ groups; or phenyl optionally substituted with one or more independently selected $R^5$ groups;

$R^1$ is $C_{1-4}$ alkyl optionally substituted with one or more independently selected
—OH;
$C_{1-4}$ alkoxy; or
4-6 membered monocyclic heterocycle comprising 1 or 2 heteroatoms independently selected from the group consisting of O, S, and N;

phenyl optionally substituted with one or more independently selected $R^4$ groups;

N-linked 4-6 membered monocyclic heterocycle comprising 1, 2, or 3 heteroatoms independently selected from the group consisting of N, O, and S, wherein the monocyclic heterocycle is optionally substituted with one or more independently selected $R^5$ groups;

N-linked 4-6 membered monocyclic heterocycle comprising 1, 2, or 3 heteroatoms independently selected from the group consisting of N, O, and S, fused to a phenyl, wherein the monocyclic heterocycle and the phenyl are optionally substituted with one or more independently selected $R^5$ groups;

$C_{3-7}$ cycloalkyl optionally substituted with one or more independently selected $R^5$ groups; or —$NR^6R^7$;

$R^2$ is 5-6 membered monocyclic heteroaryl comprising 1, 2, or 3 heteroatoms independently selected from the group consisting of O, S, and N, wherein the monocyclic heteroaryl is optionally substituted with one or more independently selected $R^3$ groups;

each $R^3$ is independently selected from the group consisting of:

$C_{1-4}$ alkyl optionally substituted with one or more independently selected
$C_{3-7}$ cycloalkyl; wherein the $C_{3-7}$ cycloalkyl is optionally substituted with one or more independently selected $R^4$ groups;
4-6 membered monocyclic heterocycle comprising 1 or 2 heteroatoms independently selected from the group consisting of O, S, and N; wherein the monocyclic heterocycle is optionally substituted with one or more independently selected $R^4$ groups;
phenyl; wherein the phenyl is optionally substituted with one or more independently selected $R^4$ groups;
$C_{1-4}$ alkoxy optionally substituted with one or more independently selected $C_{3-7}$ cycloalkyl, halo, or —OCH$_3$;
—OR$^{11}$;
—OH;
halo;
—CN;
—OC(O)R$^{10}$;
—OS(O)$_2$OH;
—NHC(=S)R$^{11}$; or
—OP(O)(OH)(OH);
—C(O)NH$_2$;
phenyl; wherein the phenyl is optionally substituted with one or more independently selected $R^4$ groups;
5-6 membered monocyclic heteroaryl comprising 1, 2, or 3 heteroatoms independently selected from the group consisting of O, S, and N; wherein the monocyclic heteroaryl is optionally substituted with one or more independently selected $R^4$ groups;
$C_{3-7}$ cycloalkyl; wherein the $C_{3-7}$ cycloalkyl is optionally substituted with one or more independently selected $R^4$ groups; and 4-6 membered monocyclic heterocycle comprising 1 or 2 heteroatoms independently selected from the group consisting of O, S, and N; wherein the monocyclic heterocycle is optionally substituted with one or more independently selected $R^4$ groups;

each $R^4$ is independently selected from the group consisting of:
halo;
$C_{1-4}$ alkyl optionally substituted with one or more independently selected halo; and
$C_{1-4}$ alkoxy optionally substituted with one or more independently selected halo;

each $R^5$ is independently selected from the group consisting of:
—OH;
halo;
$C_{1-4}$ alkyl optionally substituted with one or more independently selected $C_{1-4}$ alkoxy, halo or —OH; and
$C_{1-4}$ alkoxy optionally substituted with one or more independently selected halo;

$R^6$ is H, $C_{1-4}$ alkyl, or $C_{3-7}$ cycloalkyl wherein the $C_{3-7}$ cycloalkyl is optionally substituted with one or more independently selected $R^5$ groups;

$R^7$ is $C_{1-4}$ alkyl optionally substituted with one or more independently selected halo;
phenyl optionally substituted with one or more independently selected halo;
$C_{1-4}$ alkyl optionally substituted with one or more independently selected halo; or
$C_{1-4}$ alkoxy optionally substituted with one or more independently selected halo;
$C_{1-4}$ alkoxy optionally substituted with one or more independently selected halo; or
4-6 membered monocyclic heterocycle comprising 1 or 2 heteroatoms independently selected from the group consisting of O, S, and N; wherein the monocyclic heterocycle is optionally substituted with one or more independently selected $R^5$ groups;

each $R^{8a}$ and $R^{8b}$ is independently selected from the group consisting of
H; and
$C_{1-4}$ alkyl;

$R^{9a}$ and $R^{9b}$ are independently selected from the group consisting of
H;
$C_{1-4}$ alkyl; and
$C_{3-7}$ cycloalkyl; and each $R^{10}$ is independently selected from the group consisting of
$C_{1-6}$ alkyl; and
phenyl; wherein phenyl is optionally substituted with one or more independently selected $R^4$ groups;

each $R^{11}$ is independently selected from the group consisting of
4-6 membered monocyclic heterocycle comprising 1 or 2 heteroatoms independently selected from the group consisting of O, S, and N; wherein the monocyclic heterocycle is optionally substituted with one or more independently selected $R^4$ groups;
5-6 membered monocyclic heteroaryl comprising 1, 2, or 3 heteroatoms independently selected from the group consisting of O, S, and N; wherein the monocyclic heteroaryl is optionally substituted with one or more independently selected $R^4$ groups;

$C_{3-7}$ cycloalkyl; wherein the $C_{3-7}$ cycloalkyl is optionally substituted with one or more independently selected $R^A$ groups; and phenyl; wherein phenyl is optionally substituted with one or more independently selected $R^A$ groups; and each $R^A$ is independently selected from the group consisting of

—CN, halo;

$C_{1-4}$ alkyl optionally substituted with one or more independently selected halo; and $C_{1-4}$ alkoxy optionally substituted with one or more independently selected halo.

Another aspect of the invention relates to pharmaceutical compositions comprising a compound of the invention, and a pharmaceutical carrier. Such compositions can be administered in accordance with a method of the invention, typically as part of a therapeutic regimen for treatment or prevention of conditions and disorders related to Cystic Fibrosis Transmembrane Conductance Regulator activity. In a particular aspect, the pharmaceutical compositions may additionally comprise further therapeutically active ingredients suitable for use in combination with the compounds of the invention. In a more particular aspect, the further therapeutically active ingredient is an agent for the treatment of cystic fibrosis.

Moreover, the compounds of the invention, useful in the pharmaceutical compositions and treatment methods disclosed herein, are pharmaceutically acceptable as prepared and used.

Yet another aspect of the invention relates to a method for treating, or preventing conditions and disorders related to Cystic Fibrosis Transmembrane Conductance Regulator activity in mammals. More particularly, the method is useful for treating or preventing conditions and disorders related to cystic fibrosis, Sjögren's syndrome, pancreatic insufficiency, chronic obstructive lung disease, or chronic obstructive airway disease. Accordingly, the compounds and compositions of the invention are useful as a medicament for treating or preventing Cystic Fibrosis Transmembrane Conductance Regulator modulated disease.

The compounds, compositions comprising the compounds, methods for making the compounds, and methods for treating or preventing conditions and disorders by administering the compounds are further described herein.

In a particular aspect, the compounds of the invention are provided for use in the treatment of cystic fibrosis. In a particular aspect, the compounds of the invention are provided for use in the treatment of cystic fibrosis caused by class I, II, III, IV, V, and/or VI mutations.

The present invention also provides pharmaceutical compositions comprising a compound of the invention, and a suitable pharmaceutical carrier for use in medicine. In a particular aspect, the pharmaceutical composition is for use in the treatment of cystic fibrosis.

These and other objects of the invention are described in the following paragraphs. These objects should not be deemed to narrow the scope of the invention.

DETAILED DESCRIPTION OF THE INVENTION

Described herein are compounds of Formula I,

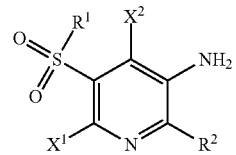

I wherein $X^1$, $X^2$, $R^1$, and $R^2$ are defined above in the Summary and below in the Detailed Description. Further, compositions comprising such compounds and methods for treating conditions and disorders using such compounds and compositions are also included.

Compounds included herein may contain one or more variable(s) that occur more than one time in any substituent or in the formulae herein. Definition of a variable on each occurrence is independent of its definition at another occurrence. Further, combinations of substituents are permissible only if such combinations result in stable compounds. Stable compounds are compounds which can be isolated from a reaction mixture.

Definitions

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "a pharmaceutically acceptable carrier" means a single pharmaceutically acceptable carrier as well as one or more pharmaceutically acceptable carriers, and the like.

As used in the specification and the appended claims, unless specified to the contrary, the following terms have the meaning presented therewith below:

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy. In some instances, the number of carbon atoms in an alkoxy moiety is indicated by the prefix "$C_{x-y}$", wherein x is the minimum and y is the maximum number of carbon atoms in the substituent. Thus, for example, "$C_{1-6}$ alkoxy" means an alkoxy substituent containing from 1 to 6 carbon atoms and "$C_{1-4}$ alkoxy" means an alkoxy substituent containing from 1 to 4 carbon atoms.

The term "alkyl" as used herein, means a saturated, straight or branched hydrocarbon chain radical. In some instances, the number of carbon atoms in an alkyl moiety is indicated by the prefix "$C_{x-y}$", wherein x is the minimum and y is the maximum number of carbon atoms in the substituent. Thus, for example, "$C_{1-6}$ alkyl" means an alkyl substituent containing from 1 to 6 carbon atoms and "$C_{1-4}$ alkyl" means an alkyl substituent containing from 1 to 4 carbon atoms. Examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 3,3-dimethylbutyl, 1,1-dimethylpropyl, 1,2-dimethylpropyl, 2,2-dimethylpropyl, 1-methylpropyl, 2-methylpropyl, 1-ethylpropyl, and 1,2,2-trimethylpropyl.

The term "C$_{3-7}$ cycloalkyl" as used herein, means cyclopropyl, cyclobutyl, cyclopentyl, cyclohexyl, and cycloheptyl, each of which is optionally substituted unless otherwise indicated.

The term "C$_{3-6}$ cycloalkyl" as used herein, means cyclopropyl, cyclobutyl, cyclopentyl, and cyclohexyl, each of which is optionally substituted unless otherwise indicated.

The term "C$_{4-6}$ cycloalkyl" as used herein, means cyclobutyl, cyclopentyl, and cyclohexyl, each of which is optionally substituted unless otherwise indicated.

The term "halo" or "halogen" as used herein, means chloro (Cl), bromo (Br), iodo (I), and fluoro (F).

The term "monocyclic heterocycle" or "monocyclic heterocyclic" as used herein, means a three-, four-, five-, six-, seven-, or eight-membered fully saturated monocyclic carbocyclic ring wherein one or more carbon ring atom is replaced by heteroatom independently selected from the group consisting of O, N, and S. 3- and 4-Membered monocyclic heterocycles have one carbon ring atom replaced by a heteroatom selected from the group consisting of O, N, and S. 5-, 6-, 7-, and 8-Membered monocyclic heterocycles may have one, two, or three carbon ring atoms replaced by heteroatoms selected from the group consisting of O, N, and S. Examples of five-membered monocyclic heterocycles include those containing in the ring: 1 O; 1 S; 1 N; 2 N; 3 N; 1 S and 1 N; 1 S, and 2 N; 1 O and 1 N; or 1 O and 2 N. Non-limiting examples of 5-membered monocyclic heterocyclic groups include 1,3-dioxolanyl, tetrahydrofuranyl, dihydrofuranyl, tetrahydrothienyl, dihydrothienyl, imidazolidinyl, oxazolidinyl, imidazolinyl, isoxazolidinyl, pyrazolidinyl, pyrazolinyl, pyrrolidinyl, 2-pyrrolinyl, 3-pyrrolinyl, thiazolinyl, and thiazolidinyl. Examples of six-membered monocyclic heterocyclic include those containing in the ring: 1 O; 2 O; 1 S; 2 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Examples of 6-membered monocyclic heterocyclic groups include tetrahydropyranyl, dihydropyranyl, 1,4-dioxanyl, 1,4-dithianyl, hexahydropyrimidine, morpholinyl, piperazinyl, piperidinyl, 1,2,3,6-tetrahydropyridinyl, tetrahydrothiopyranyl, thiomorpholinyl, thioxanyl, and trithianyl. Representative examples of monocyclic heterocycles include, but are not limited to, azetidinyl, azepanyl, aziridinyl, diazepanyl, 1,4-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyridinyl, tetrahydropyranyl, tetrahydrothienyl, thiadiazolinyl, thiadiazolidinyl, thiazolinyl, thiazolidinyl, thiomorpholinyl, thiopyranyl, and trithianyl.

The term "4-6 membered monocyclic heterocycle" or "4-6 membered monocyclic heterocyclic" as used herein, means a 4-, 5-, or 6-membered monocyclic heterocycle as defined herein above. Non-limiting examples of 4-6 membered monocyclic heterocycle include azetidinyl, oxetanyl, 1,3-dioxolanyl, pyrrolidinyl, tetrahydrofuranyl, tetrahydropyranyl, 1,4-dioxanyl, piperazinyl, piperidinyl, thiomorpholinyl, and morpholinyl.

The term "3-6 membered monocyclic heterocycle" or "3-6 membered monocyclic heterocyclic" as used herein, means a 3-, 4-, 5-, or 6-membered monocyclic heterocycle as defined herein above. Non-limiting examples of 3-6 membered monocyclic heterocycle include aziridinyl, azetidinyl, oxetanyl, pyrrolidinyl, tetrahydrofuranyl, tetrahydropyranyl, piperazinyl, piperidinyl, thiomorpholinyl, and morpholinyl.

The term "5-11 membered spiro heterocycle" as used herein, means a 3-6 membered monocyclic heterocycle wherein two substituents on the same carbon atom of the 3-6 membered monocyclic heterocycle ring together with said carbon atom form a second ring system; wherein the second ring system is a C$_{3-6}$ cycloalkyl or a 3-6 membered monocyclic heterocycle. Examples of 5-11 membered spiro heterocycle include, but not limited to, 1-oxaspiro[4.4]non-3-yl, and 1-oxaspiro[4.5]decan-3-yl.

The term "7-11 membered spiro heterocycle" as used herein, means a 4-6 membered monocyclic heterocycle wherein two substituents on the same carbon atom of the 4-6 membered monocyclic heterocycle ring together with said carbon atom form a second ring system; wherein the second ring system is a C$_{4-6}$ cycloalkyl or a 4-6 membered monocyclic heterocycle. Particular examples of 7-11 membered spiro heterocycles are 6-oxa-2-azaspiro[3.5]nonyl, 6-oxa-2-azaspiro[3.4]octyl, and 2-oxa-6-azaspiro[3.3]heptyl.

The monocyclic heterocycles and the spiro heterocycles, including the exemplary rings, are optionally substituted, and are connected to the parent molecular moiety through any carbon atom or any nitrogen atom contained within the ring systems, unless otherwise indicated. The nitrogen atoms within the heterocycle rings may optionally be oxidized or may optionally be quaternized.

The term "5-6 membered monocyclic heteroaryl" as used herein, means a five- or six-membered monocyclic aromatic ring structure wherein one or more of the ring carbon atoms are replaced with heteroatom(s) independently selected from the group consisting of O, N, and S. The five-membered ring contains two double bonds. The 5 membered ring may also contain one heteroatom selected from the group consisting of O and S; or may contain one, two, three, or four nitrogen atoms and optionally one oxygen or one sulfur atom. The 6-membered ring contains three double bonds and one, two, three or four nitrogen atoms. Representative examples of 5-6 membered monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The 5-6 membered monocyclic heteroaryls, including exemplary rings, are optionally substituted unless otherwise indicated, and are connected to the parent molecular moiety through any substitutable carbon atom or any substitutable nitrogen atom contained within the ring systems. The nitrogen atom in the heteroaryl rings may optionally be oxidized and may optionally be quaternized.

The term "phenoxy" as used herein means a phenyl appended to the parent molecular moiety through an oxygen atom.

The term "heteroatom" as used herein, means a nitrogen (N), oxygen (O), or sulfur (S).

The term "radiolabel" refers to a compound of the invention in which at least one of the atoms is a radioactive atom or radioactive isotope, wherein the radioactive atom or isotope spontaneously emits gamma rays or energetic particles, for example alpha particles or beta particles, or positrons. Examples of such radioactive atoms include, but are not limited to, $^{3}$H (tritium), $^{14}$C, $^{11}$C, $^{15}$O, $^{18}$F, $^{35}$S, $^{123}$I, and $^{125}$I.

If a moiety is described as "substituted", a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The term "substituted with one or more" refers to one to four substituents. In one embodiment it refers to one to three substituents. In further embodiments it refers to one or two substituents. In a yet further embodiment it refers to one substituent.

The terms "treat", "treating", and "treatment" refer to a method of alleviating or abrogating a disease and/or its attendant symptoms. In certain embodiments, "treat," "treating," and "treatment" refer to ameliorating at least one physical parameter, which may not be discernible by the subject. In yet another embodiment, "treat", "treating", and "treatment" refer to modulating the disease or disorder, either physically (for example, stabilization of a discernible symptom), physiologically (for example, stabilization of a physical parameter), or both. In a further embodiment, "treat", "treating", and "treatment" refer to slowing the progression of the disease or disorder.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring or developing a disease or disorder.

The phrase "therapeutically effective amount" means an amount of a compound, or a pharmaceutically acceptable salt thereof, sufficient to prevent the development of, or to alleviate to some extent, one or more of the symptoms of the condition or disorder being treated when administered alone or in conjunction with another therapeutic agent for treatment in a particular subject or subject population. The "therapeutically effective amount" may vary depending on the compound, the disease and its severity, and the age, weight, health, etc., of the subject to be treated. For example in a human or other mammal, a therapeutically effective amount may be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, pigs, horses, dogs, cats, rabbits, rats, mice and the like. In preferred embodiments, the subject is a human. The terms "human," "patient," and "subject" are used interchangeably herein.

As used herein, "Class I mutation(s)" refers to mutations which interfere with protein synthesis. They result in the introduction of a premature signal of termination of translation (stop codon) in the mRNA. The truncated CFTR proteins are unstable and rapidly degraded, so, the net effect is that there is no protein at the apical membrane. In particular, Class I mutation(s) refers to p.Gly542X (G542X), W1282X, c.489+1G>T (621+1G>T), or c.579+1G>T (711+1G>T) mutation. More particularly, Class I mutation(s) refers to G542X; or W1282X mutations.

As used herein, "Class II mutation(s)" refers to mutations which affect protein maturation. These lead to the production of a CFTR protein that cannot be correctly folded and/or trafficked to its site of function on the apical membrane. In particular, Class II mutation(s) refers to p.Phe508del (F508del), p.Ile507del, or p.Asn1303Lys (N1303K) mutations. More particularly, Class II mutation(s) refers to F508del or N1303K mutations.

As used herein, "Class III mutation(s)" refers to mutations which alter the regulation of the CFTR channel. The mutated CFTR protein is properly trafficked and localized to the plasma membrane but cannot be activated, or it cannot function as a chloride channel. In particular, Class III mutation(s) refers to p.Gly551Asp (G551D), G551S, R553G; G1349D; 51251N, G178R, S549N mutations. More particularly, Class III mutation(s) refers to G551D, R553G, G1349D, 51251N, G178R, or S549N mutations.

As used herein, "Class IV mutation(s)" refers to mutations which affect chloride conductance. The CFTR protein is correctly trafficked to the cell membrane but generates reduced chloride flow or a "gating defect" (most are missense mutations located within the membrane-spanning domain). In particular, Class IV mutation(s) refers to p.Arg117His (R117H), R347P, or p.Arg334Trp (R334W) mutations.

As used herein, "Class V mutation(s)" refers to mutations which reduce the level of normally functioning CFTR at the apical membrane or result in a "conductance defect" (for example partially aberrant splicing mutations or inefficient trafficking missense mutations). In particular, Class V mutation(s) refers to c.1210-12T[5] (5T allele), c.S3140-26A>G (3272-26A>G), c.3850-2477C>T (3849+10kbC>T) mutations.

As used herein, "Class VI mutation(s)" refers to mutations which decrease the stability of the CFTR which is present or which affect the regulation of other channels, resulting in inherent instability of the CFTR protein. In effect, although functional, the CFTR protein is unstable at the cell surface and it is rapidly removed and degraded by cell machinery. In particular, Class VI mutation(s) refers to Rescued F508del, 120del23, N287Y, 4326delTC, or 4279insA mutations. More particularly, Class VI mutation(s) refers to Rescued F508del mutations.

Compounds

Compounds of the invention have the general Formula I as described above.

Particular values of variable groups are as follows. Such values may be used where appropriate with any of the other values, definitions, claims or embodiments defined hereinbefore or hereinafter.

Certain embodiments pertain to compounds of Formula I, $$\text{Structure I: pyridine ring with } O_2S(R^1) \text{ at one position, } X^2 \text{ and } NH_2 \text{ adjacent, } X^1 \text{ and } R^2 \text{ flanking N}$$

wherein
$X^1$ and $X^2$ are independently selected
  H;
  halo;
  $C_{1-4}$ alkyl optionally substituted with one or more independently selected halo;
  $C_{1-4}$ alkoxy optionally substituted with one or more independently selected
    —OH;
    $C_{1-4}$ alkoxy; or
    —$NR^{8A}R^{8B}$;
  —$NR^{9A}R^{9B}$;
  cyclopropyl optionally substituted with one or more independently selected $R^5$ groups;
  phenoxy optionally substituted with one or more independently selected $R^5$ groups; or
  phenyl optionally substituted with one or more independently selected $R^5$ groups;
$R^1$ is
  $C_{1-4}$ alkyl optionally substituted with one or more independently selected
    —OH;
    $C_{1-4}$ alkoxy; or
    4-6 membered monocyclic heterocycle comprising 1 or 2 heteroatoms independently selected from the group consisting of O, S, and N;
  phenyl optionally substituted with one or more independently selected $R^4$ groups;
  N-linked 4-6 membered monocyclic heterocycle comprising 1, 2, or 3 heteroatoms independently selected from the group consisting of N, O, and S, wherein the monocyclic heterocycle is optionally substituted with one or more independently selected $R^5$ groups;
  N-linked 4-6 membered monocyclic heterocycle comprising 1, 2, or 3 heteroatoms independently selected from the group consisting of N, O, and S, fused to a phenyl, wherein the monocyclic heterocycle and the phenyl are optionally substituted with one or more independently selected $R^5$ groups;
  $C_{3-7}$ cycloalkyl optionally substituted with one or more independently selected $R^5$ groups; or —$NR^6R^7$;
$R^2$ is 5-6 membered monocyclic heteroaryl comprising 1, 2, or 3 heteroatoms independently selected from the group consisting of O, S, and N, wherein the monocyclic heteroaryl is optionally substituted with one or more independently selected $R^3$ groups;
each $R^3$ is independently selected from the group consisting of:
  $C_{1-4}$ alkyl optionally substituted with one or more independently selected
    $C_{3-7}$ cycloalkyl; wherein the $C_{3-7}$ cycloalkyl is optionally substituted with one or more independently selected $R^A$ groups;
    4-6 membered monocyclic heterocycle comprising 1 or 2 heteroatoms independently selected from the group consisting of O, S, and N; wherein the monocyclic heterocycle is optionally substituted with one or more independently selected $R^A$ groups;
    phenyl; wherein the phenyl is optionally substituted with one or more independently selected $R^A$ groups;
    $C_{1-4}$ alkoxy optionally substituted with one or more independently selected $C_{3-7}$ cycloalkyl, halo, or —$OCH_3$;
    —$OR^{11}$;
    —OH;
    halo;
    —CN;
    —$OC(O)R^{10}$;
    —$OS(O)_2OH$;
    —$NHC(=S)R^{11}$; or
    —$OP(O)(OH)(OH)$;
  —$C(O)NH_2$;
  phenyl; wherein the phenyl is optionally substituted with one or more independently selected $R^A$ groups;
  5-6 membered monocyclic heteroaryl comprising 1, 2, or 3 heteroatoms independently selected from the group consisting of O, S, and N; wherein the monocyclic heteroaryl is optionally substituted with one or more independently selected $R^A$ groups;
  $C_{3-7}$ cycloalkyl; wherein the $C_{3-7}$ cycloalkyl is optionally substituted with one or more independently selected $R^A$ groups; and
  4-6 membered monocyclic heterocycle comprising 1 or 2 heteroatoms independently selected from the group consisting of O, S, and N; wherein the monocyclic heterocycle is optionally substituted with one or more independently selected $R^A$ groups;
each $R^4$ is independently selected from the group consisting of:
  halo;
  $C_{1-4}$ alkyl optionally substituted with one or more independently selected halo; and
  $C_{1-4}$ alkoxy optionally substituted with one or more independently selected halo;
each $R^5$ is independently selected from the group consisting of:
  —OH;
  halo;
  $C_{1-4}$ alkyl optionally substituted with one or more independently selected $C_{1-4}$ alkoxy, halo or —OH; and
  $C_{1-4}$ alkoxy optionally substituted with one or more independently selected halo;
$R^6$ is H, $C_{1-4}$ alkyl, or $C_{3-7}$ cycloalkyl wherein the $C_{3-7}$ cycloalkyl is optionally substituted with one or more independently selected $R^5$ groups;
$R^7$ is
  $C_{1-4}$ alkyl optionally substituted with one or more independently selected halo;
    phenyl optionally substituted with one or more independently selected halo;
      $C_{1-4}$ alkyl optionally substituted with one or more independently selected halo; or
      $C_{1-4}$ alkoxy optionally substituted with one or more independently selected halo;
    $C_{1-4}$ alkoxy optionally substituted with one or more independently selected halo; or
    4-6 membered monocyclic heterocycle comprising 1 or 2 heteroatoms independently selected from the group consisting of O, S, and N; wherein the monocyclic heterocycle is optionally substituted with one or more independently selected $R^5$ groups;

each $R^{8a}$ and $R^{8b}$ is independently selected from the group consisting of
H; and
$C_{1-4}$ alkyl;
$R^{9a}$ and $R^{9b}$ are independently selected from the group consisting of
H;
$C_{1-4}$ alkyl; and
$C_{3-7}$ cycloalkyl; and
each $R^{10}$ is independently selected from the group consisting of
$C_{1-6}$ alkyl; and
phenyl; wherein phenyl is optionally substituted with one or more independently selected $R^A$ groups;
each $R^{11}$ is independently selected from the group consisting of
4-6 membered monocyclic heterocycle comprising 1 or 2 heteroatoms independently selected from the group consisting of O, S, and N; wherein the monocyclic heterocycle is optionally substituted with one or more independently selected $R^A$ groups;
5-6 membered monocyclic heteroaryl comprising 1, 2, or 3 heteroatoms independently selected from the group consisting of O, S, and N; wherein the monocyclic heteroaryl is optionally substituted with one or more independently selected $R^A$ groups;
$C_{3-7}$ cycloalkyl; wherein the $C_{3-7}$ cycloalkyl is optionally substituted with one or more independently selected $R^A$ groups; and
phenyl; wherein phenyl is optionally substituted with one or more independently selected $R^A$ groups; and
each $R^A$ is independently selected from the group consisting of
—CN,
halo;
$C_{1-4}$ alkyl optionally substituted with one or more independently selected halo; and
$C_{1-4}$ alkoxy optionally substituted with one or more independently selected halo. Certain embodiments pertain to compounds of Formula I,

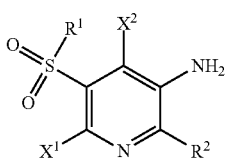

I wherein
$X^1$ and $X^2$ are independently selected
H;
halo;
$C_{1-4}$ alkyl optionally substituted with one or more independently selected halo;
$C_{1-4}$ alkoxy optionally substituted with one or more independently selected
—OH;
$C_{1-4}$ alkoxy; or
—$NR^{8A}R^{8B}$;
—$NR^{9A}R^{9B}$;
cyclopropyl optionally substituted with one or more independently selected $R^5$ groups;
phenoxy optionally substituted with one or more independently selected $R^5$ groups; or
phenyl optionally substituted with one or more independently selected $R^5$ groups;
$R^1$ is
$C_{1-4}$ alkyl optionally substituted with one or more independently selected
—OH;
$C_{1-4}$ alkoxy; or
4-6 membered monocyclic heterocycle comprising 1 or 2 heteroatoms independently selected from the group consisting of O, S, and N;
phenyl optionally substituted with one or more independently selected $R^4$ groups;
N-linked 4-6 membered monocyclic heterocycle comprising 1, 2, or 3 heteroatoms independently selected from the group consisting of N, O, and S, wherein the monocyclic heterocycle is optionally substituted with one or more independently selected $R^5$ groups;
N-linked 4-6 membered monocyclic heterocycle comprising 1, 2, or 3 heteroatoms independently selected from the group consisting of N, O, and S, fused to a phenyl, wherein the monocyclic heterocycle and the phenyl are optionally substituted with one or more independently selected $R^5$ groups;
$C_{3-7}$ cycloalkyl optionally substituted with one or more independently selected $R^5$ groups; or
—$NR^6R^7$;
$R^2$ is 5-6 membered monocyclic heteroaryl comprising 1, 2, or 3 heteroatoms independently selected from the group consisting of O, S, and N, wherein the monocyclic heteroaryl is optionally substituted with one or more independently selected $R^3$ groups;
each $R^3$ is independently selected from the group consisting of:
$C_{1-4}$ alkyl optionally substituted with one or more independently selected cyclopropyl;
4-6 membered monocyclic heterocycle comprising 1 or 2 heteroatoms independently selected from the group consisting of O, S, and N;
phenyl;
$C_{1-4}$ alkoxy optionally substituted with one or more independently selected cyclopropyl, halo, or —$OCH_3$;
—$OR^{11}$;
—OH;
halo;
—CN;
—$OC(O)R^{10}$;
—$OS(O)_2OH$;
—$NHC(=S)R^{11}$; or
—$OP(O)(OH)(OH)$;
—$C(O)NH_2$;
$C_{3-7}$ cycloalkyl; and
4-6 membered monocyclic heterocycle comprising 1 or 2 heteroatoms independently selected from the group consisting of O, S, and N;
each $R^4$ is independently selected from the group consisting of:
halo;
$C_{1-4}$ alkyl optionally substituted with one or more independently selected halo; and
$C_{1-4}$ alkoxy optionally substituted with one or more independently selected halo;
each $R^5$ is independently selected from the group consisting of:
—OH;
halo;

$C_{1-4}$ alkyl optionally substituted with one or more independently selected $C_{1-4}$ alkoxy, halo or —OH; and
$C_{1-4}$ alkoxy optionally substituted with one or more independently selected halo;

$R^6$ is H, $C_{1-4}$ alkyl, or $C_{3-7}$ cycloalkyl wherein the $C_{3-7}$ cycloalkyl is optionally substituted with one or more independently selected $R^5$ groups;

$R^7$ is
$C_{1-4}$ alkyl optionally substituted with one or more independently selected halo;
phenyl optionally substituted with one or more independently selected halo;
$C_{1-4}$ alkyl optionally substituted with one or more independently selected halo; or
$C_{1-4}$ alkoxy optionally substituted with one or more independently selected halo;
$C_{1-4}$ alkoxy optionally substituted with one or more independently selected halo; or
4-6 membered monocyclic heterocycle comprising 1 or 2 heteroatoms independently selected from the group consisting of O, S, and N; wherein the monocyclic heterocycle is optionally substituted with one or more independently selected $R^5$ groups;

each $R^{8a}$ and $R^{8b}$ is independently selected from the group consisting of
H; and
$C_{1-4}$ alkyl;

$R^{9a}$ and $R^{9b}$ are independently selected from the group consisting of
H;
$C_{1-4}$ alkyl; and
$C_{3-7}$ cycloalkyl; and each $R^{10}$ is independently selected from the group consisting of
$C_{1-6}$ alkyl; and
phenyl; and each $R^{11}$ is independently selected from the group consisting of
4-6 membered monocyclic heterocycle comprising 1 or 2 heteroatoms independently selected from the group consisting of O, S, and N;
5-6 membered monocyclic heteroaryl comprising 1, 2, or 3 heteroatoms independently selected from the group consisting of O, S, and N;
$C_{3-7}$ cycloalkyl; and
phenyl optionally substituted with one or more independently selected halo.

In certain embodiments of Formula I, $R^1$ is phenyl optionally substituted with one or more independently selected $R^4$ groups.

In certain embodiments of Formula I, $R^1$ is phenyl optionally substituted with one, two, or three independently selected $R^4$ groups.

In certain embodiments of Formula I, $R^1$ is phenyl which is unsubstituted.

In certain embodiments of Formula I, $R^1$ is phenyl which is substituted with one or two independently selected $R^4$ groups.

In certain embodiments of Formula I, $R^1$ is phenyl which is substituted with one independently selected $R^4$ groups.

In certain embodiments of Formula I, each $R^4$ is independently selected from the group consisting of fluoro; $C_{1-4}$ alkyl optionally substituted with 1, 2, or 3 fluoro; and $C_{1-4}$ alkoxy optionally substituted with 1, 2, or 3 fluoro.

In certain embodiments of Formula I, each $R^4$ is independently selected from the group consisting of $C_{1-4}$ alkyl optionally substituted with 1, 2, or 3 fluoro; and $C_{1-4}$ alkoxy optionally substituted with 1, 2, or 3 fluoro.

In certain embodiments of Formula I, each $R^4$ is selected form the group consisting of F, —$CH_3$, —$CH(CH_3)_2$, t-Bu, —$CF_3$, —$OCH_3$, —$OCH(CH_3)_2$, and —$OCF_3$. In some embodiments of Formula I, $R^4$ is selected form the group consisting of F, —$CF_3$, and —$OCF_3$. In some embodiments of Formula I, $R^4$ is —$CH(CH_3)_2$. In some embodiments of Formula I, $R^4$ is F. In some embodiments of Formula I, $R^4$ is —$CF_3$. In some embodiments of Formula I, $R^4$ is —$OCF_3$.

In certain embodiments of Formula I, $R^1$ is phenyl substituted with one —$OCF_3$.

In certain embodiments of Formula I, $R^1$ is N-linked 4-6 membered monocyclic heterocycle comprising 1, 2, or 3 heteroatoms independently selected from the group consisting of N, O, and S, wherein the monocyclic heterocycle is optionally substituted with 1, 2, or 3 independently selected $R^5$ groups.

In certain embodiments of Formula I, $R^1$ is N-linked 4-6 membered monocyclic heterocycle comprising 1 or 2 heteroatoms independently selected from the group consisting of N and O, wherein the monocyclic heterocycle is optionally substituted with 1, 2, or 3 independently selected $R^5$ groups. In some such embodiments of Formula I, each $R^5$ is independently selected from the group consisting of F, —$CH_3$, —$CH(CH_3)_2$, t-Bu, —$CF_3$, —$OCH_3$, and —$OCF_3$. In some such embodiments of Formula I, each $R^5$ is independently selected from the group consisting of F, —$CH_3$, t-Bu, —$CF_3$, —$OCH_3$, —$CH_2OH$, and —$OCF_3$.

In certain embodiments of Formula I, $R^1$ is azetidinyl, pyrrolidinyl, morpholinyl, or piperidinyl, each of which is optionally substituted with 1 or 2 independently selected $R^5$ groups. In some such embodiments of Formula I, each $R^5$ is independently selected from the group consisting of F, —$CH_3$, —$CH(CH_3)_2$, t-Bu, —$CF_3$, —$OCH_3$, and —$OCF_3$.

In certain embodiments of Formula I, $R^1$ is piperidinyl, which is optionally substituted with 1 or 2 independently selected $R^5$ groups. In some such embodiments of Formula I, each $R^5$ is independently selected from the group consisting of F, —$CH_3$, t-Bu, —$CF_3$, —$OCH_3$, and —$OCF_3$. In some such embodiments, $R^1$ is piperidinyl substituted with two fluoro groups. In some such embodiments of Formula I, $R^1$ is piperidinyl substituted with one fluoro group. In some such embodiments of Formula I, $R^1$ is piperidinyl substituted with one methyl group. In some such embodiments of Formula I, $R^1$ is piperidinyl substituted with two methyl groups. In some such embodiments of Formula I, $R^1$ is piperidinyl substituted with one —$CF_3$, group. In some such embodiments of Formula I, $R^1$ is piperidinyl substituted with one —$OCH_3$, group. In some such embodiments of Formula I, $R^1$ is piperidinyl substituted with one —$OCF_3$, group. In some such embodiments of Formula I, $R^1$ is piperidinyl substituted with one t-Bu group.

In certain embodiments of Formula I, $R^1$ is N-linked 4-6 membered monocyclic heterocycle comprising 1, 2, or 3 heteroatoms independently selected from the group consisting of N, O, and S, fused to a phenyl, wherein the monocyclic heterocycle and the phenyl are optionally substituted with 1, 2, or 3 independently selected $R^5$ groups. In some such embodiments of Formula I, $R^1$ is 3,4-dihydro-2H-benzo[b][1,4]oxazinyl, optionally substituted with 1, 2, or 3 independently selected $R^5$ groups. In some such embodiments of Formula I, $R^1$ is unsubstituted 3,4-dihydro-2H-benzo[b][1,4]oxazinyl.

In certain embodiments of Formula I, $R^1$ is $C_{1-4}$ alkyl optionally substituted with one or more independently selected —OH, $C_{1-4}$ alkoxy, or 4-6 membered monocyclic heterocycle comprising 1 or 2 heteroatoms independently selected from the group consisting of O, S, and N. In some such embodiments of Formula I, $R^1$ is $C_{1-4}$ alkyl which is unsubstituted. In some such embodiments of Formula I, $R^1$ is $C_{1-4}$ alkyl which is substituted with —OH. In some such embodiments of Formula I, $R^1$ is $C_{1-4}$ alkyl which is substituted with $C_{1-4}$ alkoxy. In some such embodiments of Formula I, $R^1$ is $C_{1-4}$ alkyl which is substituted with 4-6 membered monocyclic heterocycle comprising 1 or 2 heteroatoms independently selected from the group consisting of O, S, and N. In some such embodiments of Formula I, $R^1$ is —$CH_2CH_3$. In some such embodiments of Formula I, $R^1$ is —$CH_2CH_2OH$. In some such embodiments of Formula I, $R^1$ is —$CH(CH_3)_2$. In some such embodiments, $R^1$ is —$CH_2CH_2OCH_3$. In some such embodiments of Formula I, $R^1$ is $C_1$ alkyl substituted with tetrahydrofuran.

In certain embodiments of Formula I, $R^1$ is $C_{3-7}$ cycloalkyl optionally substituted with one or more independently selected $R^5$ groups. In some such embodiments of Formula I, $R^1$ is cyclopropyl, cyclobutyl, cyclopentyl, or cyclohexyl. In some such embodiments of Formula I, $R^1$ is cyclopentyl.

In certain embodiments of Formula I, $R^1$ is —$NR^6R^7$.

In certain embodiments of Formula I, $R^1$ is —$NR^6R^7$; wherein
$R^6$ is H, —$CH_3$, or cyclopropyl; wherein the cyclopropyl is optionally substituted with 1 or 2 independently selected $R^5$ groups; and
$R^7$ is
  $C_{1-4}$ alkyl;
  $C_{1-4}$ alkyl substituted with 1, 2, or 3 fluoro;
  $C_{1-4}$ alkyl substituted with one phenyl wherein the phenyl is optionally substituted with 1, 2, or 3 independently selected fluoro;
    $C_{1-4}$ alkyl optionally substituted with 1, 2, or 3 fluoro; or
    $C_{1-4}$ alkoxy optionally substituted with 1, 2, or 3 fluoro;
  $C_{2-4}$ alkyl substituted with one $C_{1-4}$ alkoxy; or
  $C_{1-4}$ alkyl substituted with one 4-6 membered monocyclic heterocycle comprising 1 or 2 heteroatoms independently selected from the group consisting of O, S, and N; wherein the monocyclic heterocycle is optionally substituted with 1, 2, or 3 independently selected $R^5$ groups.

In certain embodiments of Formula I, $R^1$ is —$NR^6R^7$; wherein
$R^6$ is H, —$CH_3$, cyclobutyl or cyclopropyl; wherein the cyclobutyl and cyclopropyl are optionally substituted with 1 or 2 independently selected $R^5$ groups; and
$R^7$ is
  $C_{1-4}$ alkyl;
  $C_{1-4}$ alkyl substituted with 1, 2, or 3 fluoro;
  $C_{1-4}$ alkyl substituted with one phenyl wherein the phenyl is optionally substituted with 1, 2, or 3 independently selected fluoro;
    $C_{1-4}$ alkyl optionally substituted with 1, 2, or 3 fluoro; or
    $C_{1-4}$ alkoxy optionally substituted with 1, 2, or 3 fluoro;
  $C_{2-4}$ alkyl substituted with one $C_{1-4}$ alkoxy; or
  $C_{1-4}$ alkyl substituted with one 4-6 membered monocyclic heterocycle comprising 1 or 2 heteroatoms independently selected from the group consisting of O, S, and N; wherein the monocyclic heterocycle is optionally substituted with 1, 2, or 3 independently selected $R^5$ groups.

In certain embodiments of Formula I, $R^7$ is $C_{1-4}$ alkyl substituted with one phenyl wherein the phenyl is optionally substituted with 1, 2, or 3 independently selected —$CF_3$, fluoro, or $C_{1-4}$ alkoxy. In some such embodiments, $R^7$ is $C_{1-4}$ alkyl substituted with one phenyl wherein the phenyl is unsubstituted.

In certain embodiments of Formula I, $X^1$ is H; halo; $C_{1-4}$ alkyl optionally substituted with one or more independently selected halo; $C_{1-4}$ alkoxy optionally substituted with one or more independently selected —OH, $C_{1-4}$ alkoxy, or —$NR^{11A}R^{11B}$; —$NR^{12A}R^{12B}$; optionally substituted cyclopropyl; optionally substituted phenoxy; or optionally substituted phenyl.

In certain embodiments of Formula I, $R^1$ is —$NR^6R^7$; wherein
$R^6$ is —$CH_3$; and
$R^7$ is
  $C_{1-4}$ alkyl substituted with one phenyl wherein the phenyl is optionally substituted with 1, 2, or 3 independently selected fluoro;
    $C_{1-4}$ alkyl optionally substituted with 1, 2, or 3 fluoro; or
    $C_{1-4}$ alkoxy optionally substituted with 1, 2, or 3 fluoro;
  $C_{2-4}$ alkyl substituted with one $C_{1-4}$ alkoxy; or
  $C_{1-4}$ alkyl substituted with one 4-6 membered monocyclic heterocycle comprising 1 or 2 heteroatoms independently selected from the group consisting of O, S, and N; wherein the monocyclic heterocycle is optionally substituted with 1, 2, or 3 independently selected $R^5$ groups.

In certain embodiments of Formula I, $R^1$ is —$NR^6R^7$; wherein
$R^6$ is —$CH_3$; and
$R^7$ is $C_{1-4}$ alkyl substituted with one phenyl. In some such embodiments, $R^1$ is —$NR^6R^7$; wherein $R^6$ is —$CH_3$; and $R^7$ is $C_{1-4}$ alkyl substituted with one phenyl.

In certain embodiments of Formula I, $X^1$ and $X^2$ are independently selected H, halo, optionally substituted cyclopropyl, or optionally substituted phenyl.

In certain embodiments of Formula I, $X^1$ and $X^2$ are independently selected H, halo, or unsubstituted cyclopropyl.

In certain embodiments of Formula I, $X^1$ and $X^2$ are each H.

In certain embodiments of Formula I, $X^1$ is H; and $X^2$ is Cl. In certain embodiments of Formula I $X^1$ is H; and $X^2$ is Br.

In certain embodiments of Formula I, $X^1$ is Cl; and $X^2$ is H. In certain embodiments of Formula I, $X^1$ is Br; and $X^2$ is H.

In certain embodiments of Formula I, $X^1$ and $X^2$ are each independently selected H, bromo, —$NR^{12A}R^{12B}$, $C_{1-4}$ alkoxy, cyclopropyl, phenoxy, or phenyl; wherein the cyclopropyl, phenoxy, and phenyl are optionally substituted with 1, 2, or 3 independently selected $R^5$ groups, and the $C_{1-4}$ alkoxy is optionally substituted with one or more independently selected —OH, $C_{1-4}$ alkoxy, or —$NR^{11A}R^{11B}$. In some such embodiments of Formula I, the cyclopropyl is unsubstituted. In some such embodiments of Formula I, the phenyl and phenoxy are substituted with F.

In certain embodiments of Formula I, $X^1$ and $X^2$ are each H, bromo, cyclopropyl, or phenyl; wherein the cyclopropyl and the phenyl are optionally substituted with 1, 2, or 3 independently selected $R^5$ groups. In some such embodiments of Formula I, the cyclopropyl is unsubstituted.

In certain embodiments of Formula I, $X^1$ is bromo.

In certain embodiments of Formula I, $X^2$ is bromo.

In certain embodiments of Formula I, $X^1$ is cyclopropyl, or phenyl; wherein the cyclopropyl and the phenyl are optionally substituted with 1, 2, or 3 independently selected $R^5$ groups, and $X^2$ is H. In some such embodiments of Formula I, the cyclopropyl is unsubstituted.

In certain embodiments of Formula I, $X^1$ is cyclopropyl, phenoxy, or phenyl; wherein the cyclopropyl, phenoxy, and phenyl are optionally substituted with 1, 2, or 3 independently selected $R^5$ groups, and $X^2$ is H. In some such embodiments of Formula I, the cyclopropyl is unsubstituted.

In certain embodiments of Formula I, $X^1$ is unsubstituted cyclopropyl or phenyl substituted with one fluoro; and $X^2$ is H.

In certain embodiments of Formula I, $X^1$ is unsubstituted cyclopropyl, phenyl substituted with one fluoro, or phenoxy substituted with one fluoro; and $X^2$ is H.

In certain embodiments of Formula I, $X^1$ is unsubstituted cyclopropyl; and $X^2$ is H.

In certain embodiments of Formula I, $X^1$ is phenyl substituted with one fluoro; and $X^2$ is H.

In certain embodiments of Formula I, $X^1$ is phenoxy substituted with one fluoro; and $X^2$ is H.

In certain embodiments of Formula I, $X^1$ is $C_{1-4}$ alkoxy optionally substituted with one or more independently selected —OH, $C_{1-4}$ alkoxy, or —$NR^{11A}R^{11B}$; and $X^2$ is H. In some such embodiments of Formula I, $R^{11A}$ and $R^{11B}$ are H or $C_{1-4}$ alkyl. In some such embodiments of Formula I, $R^{11A}$ and $R^{11B}$ are both —$CH_3$.

In certain embodiments of Formula I, $X^1$ is $C_{1-4}$ alkoxy which is unsubstituted; and $X^2$ is H. In some such embodiments, $X^1$ is —$OCH_3$.

In certain embodiments of Formula I, $X^1$ is $C_{1-4}$ alkoxy which is substituted with $C_{1-4}$ alkoxy; and $X^2$ is H. In some such embodiments of Formula I, $X^1$ is —$OCH_2CH_2OCH_3$.

In certain embodiments of Formula I, $X^1$ is $C_{1-4}$ alkoxy which is substituted with —$NR^{11A}R^{11B}$; and $X^2$ is H. In some such embodiments of Formula I, $R^{11A}$ and $R^{11B}$ are H or $C_{1-4}$ alkyl. In some such embodiments of Formula I, $R^{11A}$ and $R^{11B}$ are both —$CH_3$.

In certain embodiments of Formula I, $X^1$ is —$NR^{12A}R^{12B}$; and $X^2$ is H. In some such embodiments of Formula I, $R^{12A}$ and $R^{12B}$ are H, $C_{1-4}$ alkyl, or $C_{3-7}$ cycloalkyl. In some such embodiments of Formula I, $R^{12A}$ and $R^{12B}$ are both —$CH_3$. In some such embodiments of Formula I, $R^{12A}$ is H and $R^{12B}$ is cyclopropyl.

In certain embodiments of Formula I, $R^2$ is 5-6 membered monocyclic heteroaryl comprising 1, 2, or 3 heteroatoms independently selected from the group consisting of O, S, and N, wherein the monocyclic heteroaryl is optionally substituted with one or more independently selected $R^3$ groups;

each $R^3$ is independently selected from the group consisting of:
  $C_{1-4}$ alkyl optionally substituted with one or more independently selected
    $C_{3-7}$ cycloalkyl; wherein the $C_{3-7}$ cycloalkyl is optionally substituted with one or more independently selected $R^A$ groups;
    4-6 membered monocyclic heterocycle comprising 1 or 2 heteroatoms independently selected from the group consisting of O, S, and N; wherein the monocyclic heterocycle is optionally substituted with one or more independently selected $R^A$ groups;
    phenyl; wherein the phenyl is optionally substituted with one or more independently selected $R^A$ groups;
  $C_{1-4}$ alkoxy optionally substituted with one or more independently selected $C_{3-7}$ cycloalkyl, halo, or —$OCH_3$;
  —$OR^{11}$;
  —OH;
  halo;
  —CN;
  —$OC(O)R^{10}$;
  —$OS(O)_2OH$;
  —$NHC(=S)R^{11}$; or
  —$OP(O)(OH)(OH)$;
  —$C(O)NH_2$,
  phenyl; wherein the phenyl is optionally substituted with one or more independently selected $R^A$ groups;
  5-6 membered monocyclic heteroaryl comprising 1, 2, or 3 heteroatoms independently selected from the group consisting of O, S, and N; wherein the monocyclic heteroaryl is optionally substituted with one or more independently selected $R^A$ groups;
  $C_{3-7}$ cycloalkyl; wherein the $C_{3-7}$ cycloalkyl is optionally substituted with one or more independently selected $R^A$ groups; and
  4-6 membered monocyclic heterocycle comprising 1 or 2 heteroatoms independently selected from the group consisting of O, S, and N; wherein the monocyclic heterocycle is optionally substituted with one or more independently selected $R^A$ groups.

In certain embodiments of Formula I, $R^2$ is 5-6 membered monocyclic heteroaryl comprising 1, 2, or 3 heteroatoms independently selected from the group consisting of O, S, and N; wherein the monocyclic heteroaryl is optionally substituted with one or more independently selected $R^3$ groups. In some such embodiments of Formula I, the monocyclic heteroaryl is unsubstituted. In some such embodiments of Formula I, the monocyclic heteroaryl is optionally substituted with one independently selected $R^3$. In some such embodiments of Formula I, the monocyclic heteroaryl is substituted with one independently selected $R^3$.

In certain embodiments of Formula I, $R^2$ is a 5 membered monocyclic heteroaryl comprising 1, 2, or 3 heteroatoms independently selected from the group consisting of O, S, and N; wherein the monocyclic heteroaryl is optionally substituted with one or more independently selected $R^3$ groups. In some such embodiments of Formula I, $R^2$ is imidazolyl, isoxazolyl, isothiazolyl, oxadiazolyl, oxazolyl, pyrazolyl, thiadiazolyl, or thiazolyl; wherein the imidazolyl, isoxazolyl, isothiazolyl, oxadiazolyl, oxazolyl, pyrazolyl, thiadiazolyl, and thiazolyl are optionally substituted with one or more independently selected $R^3$ groups. In some such embodiments of Formula I, the imidazolyl, isoxazolyl, isothiazolyl, oxadiazolyl, oxazolyl, pyrazolyl, thiadiazolyl, and thiazolyl are unsubstituted. In some such embodiments of Formula I, the imidazolyl, isoxazolyl, isothiazolyl, oxadiazolyl, oxazolyl, pyrazolyl, thiadiazolyl, and thiazolyl are optionally substituted with one or two independently selected $R^3$. In some such embodiments of Formula I, the imidazolyl, isoxazolyl, isothiazolyl, oxadiazolyl, oxazolyl, pyrazolyl, thiadiazolyl, and thiazolyl are substituted with one or two independently selected $R^3$. In some such embodiments of Formula I, $R^2$ is oxadiazolyl or thiazolyl; wherein the oxadiazolyl or thiazolyl is substituted with one independently selected $R^3$. In some such embodiments of Formula I, $R^2$ is substituted oxadiazolyl. In some such embodiments of Formula I, $R^2$ is substituted thiazolyl. In some such embodiments of Formula I, $R^2$ is 1,3,4-oxadiazolyl, 1,2,4-oxadiazolyl, 1,3,4-thiadiazolyl, or thiazolyl; wherein the 1,3,4-oxadiazolyl, 1,2,4-oxadiazolyl, 1,3,4-thiadiazolyl, and thiazolyl are optionally substituted with one or more independently selected $R^3$ groups. In some such embodiments of Formula I, the $R^2$ 1,3,4-oxadiazolyl, 1,2,4-oxadiazolyl, 1,3,4-thiadiazolyl, and thiazolyl are optionally substituted with one or two independently selected $R^3$. In some such embodiments of Formula I, the $R^2$ 1,3,4-oxadiazolyl, 1,2,4-oxadiazolyl, 1,3,4-thiadiazolyl, and thiazolyl are substituted with one or two independently selected $R^3$. In some such embodiments of Formula I, the $R^2$ 1,3,4-oxadiazolyl, 1,2,4-oxadiazolyl, 1,3,4-thiadiazolyl, and thiazolyl are substituted with one independently selected $R^3$. In some such embodiments of Formula I, $R^2$ is substituted 1,3,4-oxadiazolyl. In some such embodiments of Formula I, $R^2$ is substituted 1,2,4-oxadiazolyl. In some such embodiments of Formula I, $R^2$ is substituted 1,3,4-thiadiazolyl. In some such embodiments of Formula I, $R^2$ is substituted thiazolyl.

In certain embodiments of Formula I, $R^2$ is a 6 membered monocyclic heteroaryl comprising 1, 2, or 3 heteroatoms independently selected from the group consisting of O, S, and N; wherein the monocyclic heteroaryl is optionally substituted with one or more independently selected $R^3$ groups. In some such embodiments of Formula I, $R^2$ is pyridinyl, pyrimidinyl, pyridazinyl, or pyrazinyl; wherein the pyridinyl, pyrimidinyl, pyridazinyl, and pyrazinyl are optionally substituted with one or more independently selected $R^3$ groups. In some such embodiments of Formula I, the pyridinyl, pyrimidinyl, pyridazinyl, and pyrazinyl are unsubstituted. In some such embodiments of Formula I, the pyridinyl, pyrimidinyl, pyridazinyl, and pyrazinyl are optionally substituted with one or two independently selected $R^3$. In some such embodiments of Formula I, the pyridinyl, pyrimidinyl, pyridazinyl, and pyrazinyl are substituted with one or two independently selected $R^3$.

In certain embodiments of Formula I, each $R^3$ is independently selected from the group consisting of:
  $C_{1-4}$ alkyl optionally substituted with one or more independently selected
    $C_{3-7}$ cycloalkyl; wherein the $C_{3-7}$ cycloalkyl is optionally substituted with one or more independently selected $R^A$ groups;
    4-6 membered monocyclic heterocycle comprising 1 or 2 heteroatoms independently selected from the group consisting of O, S, and N; wherein the monocyclic heterocycle is optionally substituted with one or more independently selected $R^A$ groups;
  phenyl; wherein the phenyl is optionally substituted with one or more independently selected $R^A$ groups;
  $C_{1-4}$ alkoxy optionally substituted with one or more independently selected $C_{3-7}$ cycloalkyl, halo, or —OCH$_3$;
  —OR$^{11}$;
  —OH;
  halo;
  —CN;
  —OC(O)R$^{10}$;
  —OS(O)$_2$OH;
  —NHC(=S)R$^{11}$; or
  —OP(O)(OH)(OH);
  —C(O)NH$_2$;
  phenyl; wherein the phenyl is optionally substituted with one or more independently selected $R^A$ groups;
  5-6 membered monocyclic heteroaryl comprising 1, 2, or 3 heteroatoms independently selected from the group consisting of O, S, and N; wherein the monocyclic heteroaryl is optionally substituted with one or more independently selected $R^A$ groups;
  $C_{3-7}$ cycloalkyl; wherein the $C_{3-7}$ cycloalkyl is optionally substituted with one or more independently selected $R^A$ groups; and
  4-6 membered monocyclic heterocycle comprising 1 or 2 heteroatoms independently selected from the group consisting of O, S, and N; wherein the monocyclic heterocycle is optionally substituted with one or more independently selected $R^A$ groups.

In certain embodiments of Formula I, each $R^3$ is independently selected from the group consisting of:
  $C_{1-4}$ alkyl optionally substituted with one or more independently selected
    $C_{3-7}$ cycloalkyl;
    4-6 membered monocyclic heterocycle comprising 1 or 2 heteroatoms independently selected from the group consisting of O, S, and N;
  phenyl;
  $C_{1-4}$ alkoxy optionally substituted with one or more independently selected $C_{3-7}$ cycloalkyl, halo, or —OCH$_3$;
  —OR$^{11}$;
  —OH;
  halo;
  —NHC(=S)R$^{11}$; or
  —OP(O)(OH)(OH);
  —C(O)NH$_2$;
  $C_{3-7}$ cycloalkyl; and
  4-6 membered monocyclic heterocycle comprising 1 or 2 heteroatoms independently selected from the group consisting of O, S, and N.

In certain embodiments of Formula I, each $R^3$ is independently —C(O)NH$_2$.

In some embodiments of Formula I, each $R^3$ is independently $C_{3-7}$ cycloalkyl. In some embodiments of Formula I, each $R^3$ is independently $C_6$ cycloalkyl.

In certain embodiments of Formula I, $R^3$ is independently 4-6 membered monocyclic heterocycle comprising 1 or 2 heteroatoms independently selected from the group consisting of O, S, and N; wherein the monocyclic heterocycle is optionally substituted with one or more independently selected $R^A$ groups. In some such embodiments of Formula I, $R^3$ is independently tetrahydrofuranyl. In some such embodiments of Formula I, $R^3$ is independently tetrahydropyranyl.

In certain embodiments of Formula I, each $R^3$ is
  $C_{1-4}$ alkyl optionally substituted with one or more independently selected
    $C_{3-7}$ cycloalkyl;
    4-6 membered monocyclic heterocycle comprising 1 or 2 heteroatoms independently selected from the group consisting of O, S, and N;
  phenyl;
  $C_{1-4}$ alkoxy optionally substituted with one or more independently selected $C_{3-7}$ cycloalkyl, halo, or —OCH$_3$;
  —OR$^{11}$;
  —OH;
  halo;
  —NHC(=S)R$^{11}$; or
  —OP(O)(OH)(OH).

In certain embodiments of Formula I, each $R^3$ is independently $C_{1-4}$ alkyl; optionally substituted with one or more independently selected —OH, halo, or —OP(O)(OH)(OH). In some such embodiments of Formula I, $R^3$ is independently $C_{1-4}$ alkyl, which is unsubstituted. In some such embodiments of Formula I, $R^3$ is independently —C(CH$_3$)$_3$. In some such embodiments of Formula I, $R^3$ is independently $C_{1-4}$ alkyl substituted with one —OH. In some such embodiments of Formula I, $R^3$ is independently —CH$_2$OH. In some such embodiments of Formula I, $R^3$ is independently —CH$_2$CH$_2$OH. In some such embodiments of Formula I, $R^3$ is independently —CH(OH)CH$_3$. In some such embodiments of Formula I, $R^3$ is independently —C(OH)(CH$_3$)$_2$. In some such embodiments of Formula I, $R^3$ is independently —CH(OH)CF$_3$. In some such embodiments of Formula I, $R^3$ is independently $C_{1-4}$ alkyl substituted with one —OP(O)(OH)(OH). In some such embodiments of Formula I, $R^3$ is independently $C_1$ alkyl substituted with one —OP(O)(OH)(OH). In some such embodiments of Formula I, $R^3$ is independently $C_{1-4}$ alkyl substituted with one —OH and three F. In some such embodiments of Formula I, $R^3$ is independently $C_2$ alkyl substituted with one —OH and three F. In some such embodiments of Formula I, $R^3$ is independently $C_3$ alkyl substituted with one —OH and three F.

In certain embodiments of Formula I, each $R^3$ is independently optionally substituted $C_{1-4}$ alkyl. In some such embodiments of Formula I, $R^3$ is independently $C_{1-4}$ alkyl substituted with one $C_{1-4}$ alkoxy and one phenyl. In some such embodiments of Formula I, $R^3$ is independently —CH(OCH$_3$)-phenyl. In some such embodiments of Formula I, $R^3$ is independently $C_{1-4}$ alkyl substituted with one $C_{1-4}$ alkoxy wherein the $C_{1-4}$ alkoxy is optionally substituted with one or more independently selected $C_{3-7}$ cycloalkyl, halo, or —OCH$_3$. In some such embodiments of Formula I, $R^3$ is —CH(OCH$_3$)CH$_3$. In some such embodiments, $R^3$ is independently —C(OCH$_3$)(CH$_3$)$_2$. In some such embodiments of Formula I, $R^3$ is —CH$_2$OCH$_3$. In some such embodiments of Formula I, $R^3$ is —CH$_2$CH$_2$OCH$_3$. In some such embodiments of Formula I, $R^3$ is —CH$_2$OCH$_2$CH$_3$. In some such embodiments of Formula I, $R^3$ is —CH$_2$OCF$_3$. In some such embodiments of Formula I, $R^3$ is —CH$_2$OCHF$_2$. In some such embodiments of Formula I, $R^3$ is —CH$_2$OCH$_2$CH$_2$OCH$_3$. In some such embodiments of Formula I, $R^3$ is independently $C_{1-4}$ alkyl substituted with one $C_{1-4}$ alkoxy; wherein the $C_{1-4}$ alkoxy is optionally substituted with one or more independently selected $C_{3-7}$ cycloalkyl. In some such embodiments of Formula I, $R^3$ is independently

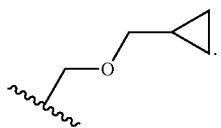 [SMILES: *COCC1CC1]

In certain embodiments of Formula I, $R^3$ is independently $C_{1-4}$ alkyl substituted with one —OR$^{11}$; and each $R^{11}$ is independently selected from the group consisting of 4-6 membered monocyclic heterocycle comprising 1 or 2 heteroatoms independently selected from the group consisting of O, S, and N; 5-6 membered monocyclic heteroaryl comprising 1, 2, or 3 heteroatoms independently selected from the group consisting of O, S, and N; $C_{3-7}$ cycloalkyl; and phenyl; wherein the phenyl is optionally substituted with one or more independently selected $R^4$ groups. In some such embodiments of Formula I, $R^3$ is independently $C_{1-4}$ alkyl substituted with one —OR$^{11}$; and $R^{11}$ is independently phenyl; wherein the phenyl is optionally substituted with one or more independently selected $R^4$ groups. In some such embodiments of Formula I, $R^3$ is independently

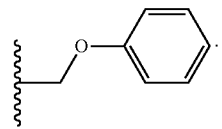

In some such embodiments of Formula I, $R^3$ is independently

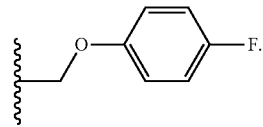

In some such embodiments of Formula I, $R^3$ is independently $C_{1-4}$ alkyl substituted with one —OR$^{11}$, and $R^{11}$ is independently $C_{3-7}$ cycloalkyl. In some such embodiments of Formula I, $R^3$ is independently —CH$_2$O—C$_5$ cycloalkyl. In some such embodiments of Formula I, $R^3$ is independently $C_{1-4}$ alkyl substituted with one —OR$^{11}$, and $R^{11}$ is independently 4-6 membered monocyclic heterocycle comprising 1 or 2 heteroatoms independently selected from the group consisting of O, S, and N. In some such embodiments of Formula I, $R^3$ is independently

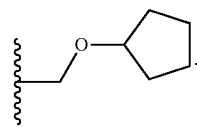 [SMILES: *COC1CCCC1]

In certain embodiments of Formula I, $R^3$ is independently $C_{1-4}$ alkyl substituted with one $C_{3-7}$ cycloalkyl; wherein the $C_{3-7}$ cycloalkyl is optionally substituted with one or more independently selected $R^4$ groups. In some such embodiments of Formula I, $R^3$ is independently $C_{1-4}$ alkyl substituted with one $C_{3-7}$ cycloalkyl; wherein the $C_{3-7}$ cycloalkyl is unsubstituted. In some such embodiments of Formula I, $R^3$ is independently $C_1$ alkyl substituted with one $C_3$ cycloalkyl; wherein the $C_3$ cycloalkyl is unsubstituted.

In certain embodiments of Formula I, $R^3$ is independently $C_{3-7}$ cycloalkyl; wherein the $C_{3-7}$ cycloalkyl is optionally substituted with one or more independently selected $R^4$ groups. In some such embodiments of Formula I, $R^3$ is independently $C_{3-7}$ cycloalkyl; wherein the $C_{3-7}$ cycloalkyl is unsubstituted. In some such embodiments of Formula I, $R^3$ is independently cyclopropyl.

In certain embodiments of Formula I, $R^3$ is independently $C_{1-4}$ alkyl substituted with one —NHC(=S)R$^{11}$; and each $R^{11}$ is independently selected from the group consisting of 4-6 membered monocyclic heterocycle comprising 1 or 2 heteroatoms independently selected from the group consisting of O, S, and N; 5-6 membered monocyclic heteroaryl comprising 1, 2, or 3 heteroatoms independently selected from the group consisting of O, S, and N; $C_{3-7}$ cycloalkyl; and phenyl; wherein the phenyl is optionally substituted with one or more independently selected $R^4$ groups; and each $R^4$ is independently selected halo. In some such embodiments of Formula I, $R^3$ is independently $C_{1-4}$ alkyl substituted with one —NHC(=S)R$^{11}$; and each $R^{11}$ is independently $C_{3-7}$ cycloalkyl. In some such embodiments of Formula I, $R^3$ is independently $C_1$ alkyl substituted with one —NHC(=S)$R^{11}$; and each $R^{11}$ is independently cyclopropyl.

In certain embodiments of Formula I, $R^3$ is independently $C_{1-4}$ alkyl substituted with one 4-6 membered monocyclic heterocycle comprising 1 or 2 heteroatoms independently selected from the group consisting of O, S, and N; wherein the monocyclic heterocycle is optionally substituted with one or more independently selected $R^A$ groups. In some such embodiments of Formula I, $R^3$ is independently $C_1$ alkyl substituted with tetrahydrofuranyl.

In certain embodiments of Formula I, $R^2$ is a 5 membered monocyclic heteroaryl comprising 1, 2, or 3 heteroatoms independently selected from the group consisting of O, S, and N, wherein the monocyclic heteroaryl is optionally substituted with one independently selected $R^3$; wherein $R^3$ is independently $C_{1-4}$ alkyl optionally substituted with one or more independently selected —OH, halo, or —OP(O)(OH)(OH). In some such embodiments of Formula I, $R^2$ is oxadiazolyl or thiazolyl wherein the oxadiazolyl or thiazolyl is substituted with one independently selected $R^3$; wherein $R^3$ is independently $C_{1-4}$ alkyl optionally substituted with one or more independently selected —OH, halo, or —OP(O)(OH)(OH).

Included herein are compounds of Formula I-a, or pharmaceutically acceptable salts thereof I-a wherein n is 0, 1, or 2, $R^{4A}$ is H, F, $CH_3$, —CH($CH_3$)$_2$, t-Bu, $CF_3$, —$OCH_3$, —O—CH($CH_3$)$_2$, or —$OCF_3$, each $R^{4B}$ is independently F or —$OCF_3$, and $X^1$ and $R^2$ are as defined in the Summary and embodiments herein for Formula I and I-b.

In certain embodiments of Formula I-a, $X^1$ is H.

In certain embodiments of Formula I-a, n is 0 or 1. In certain embodiments of Formula I-a, n is 0. In certain embodiments of Formula I-a, n is 1.

In certain embodiments of Formula I-a, $R^{4A}$ is H, —CH($CH_3$)$_2$, —O—CH($CH_3$)$_2$, t-Bu, —$CH_3$, —$OCH_3$, F, $CF_3$, or —$OCF_3$.

In certain embodiments of Formula I-a, $R^{4A}$ is H, F, $CF_3$, or —$OCF_3$.

In certain embodiments of Formula I-a, $R^{4A}$ is F, $CF_3$, or —$OCF_3$.

In certain embodiments of Formula I-a, n is 0 or 1, $R^{4A}$ is F, $CF_3$ or —$OCF_3$, and $R^{4B}$ is F.

In certain embodiments of Formula I-a, $R^{4A}$ is F.

In certain embodiments of Formula I-a, n is 0 and $R^{4A}$ is F.

In certain embodiments of Formula I-a, n is 0 and $R^{4A}$ is -$OCF_3$.

In certain embodiments of Formula I-a, n is 0 and $R^{4A}$ is H.

In certain embodiments of Formula I-a, $X^1$ is H; n is 0; $R^{4A}$ is —$OCF_3$; $R^2$ is 1,3,4-oxadiazolyl or thiazolyl substituted with one $R^3$; and $R^3$ is $C_{1-4}$ alkyl optionally substituted with one or more independently selected —OH; halo; or —OP(O)(OH)(OH).

Included herein are compounds of Formula I-b, or pharmaceutically acceptable salts thereof, I-b wherein $X^1$, $R_1$, and $R^2$ are as defined below and in the Summary and embodiments herein for Formula I.

Certain embodiments pertain to compounds of Formula I-b,

I-b wherein
$X^1$ is
  H;
  halo;
  $C_{1-4}$ alkyl optionally substituted with one or more independently selected halo;
  $C_{1-4}$ alkoxy optionally substituted with one or more independently selected
    —OH;
    $C_{1-4}$ alkoxy; or
    —$NR^{8A}R^{8B}$;
  —$NR^{9A}R^{9B}$;
  cyclopropyl optionally substituted with one or more independently selected $R^5$ groups;
  phenoxy optionally substituted with one or more independently selected $R^5$ groups; or
  phenyl optionally substituted with one or more independently selected $R^5$ groups;
$R^1$ is
  $C_{1-4}$ alkyl optionally substituted with one or more independently selected
    —OH;
    $C_{1-4}$ alkoxy; or
    4-6 membered monocyclic heterocycle comprising 1 or 2 heteroatoms independently selected from the group consisting of O, S, and N;
  phenyl optionally substituted with one or more independently selected $R^4$ groups;
  N-linked 4-6 membered monocyclic heterocycle comprising 1, 2, or 3 heteroatoms independently selected from the group consisting of N, O, and S, wherein the monocyclic heterocycle is optionally substituted with one or more independently selected $R^5$ groups;
  N-linked 4-6 membered monocyclic heterocycle comprising 1, 2, or 3 heteroatoms independently selected from the group consisting of N, O, and S, fused to a phenyl, wherein the monocyclic heterocycle and the phenyl are optionally substituted with one or more independently selected $R^5$ groups;

$C_{3-7}$ cycloalkyl optionally substituted with one or more independently selected $R^5$ groups; or

—$NR^6R^7$;

$R^2$ is 5-6 membered monocyclic heteroaryl comprising 1, 2, or 3 heteroatoms independently selected from the group consisting of O, S, and N, wherein the monocyclic heteroaryl is optionally substituted with one or more independently selected $R^3$ groups;

each $R^3$ is independently:

$C_{1-4}$ alkyl optionally substituted with one or more independently selected $C_{1-4}$ alkoxy optionally substituted with one or more independently selected halo;

—OH;

halo;

—CN;

—OC(O)$R^{10}$;

—OS(O)$_2$OH; or

—OP(O)(OH)(OH);

each $R^4$ is independently selected from the group consisting of:

halo;

$C_{1-4}$ alkyl optionally substituted with one or more independently selected halo; and $C_{1-4}$ alkoxy optionally substituted with one or more independently selected halo;

each $R^5$ is independently selected from the group consisting of:

—OH;

halo;

$C_{1-4}$ alkyl optionally substituted with one or more independently selected $C_{1-4}$ alkoxy, halo or OH; and $C_{1-4}$ alkoxy optionally substituted with one or more independently selected halo;

$R^6$ is H, $C_{1-4}$ alkyl, or $C_{3-7}$ cycloalkyl wherein the $C_{3-7}$ cycloalkyl is optionally substituted with one or more independently selected $R^5$ groups;

$R^7$ is $C_{1-4}$ alkyl optionally substituted with one or more independently selected halo;

phenyl optionally substituted with one or more independently selected halo;

$C_{1-4}$ alkyl optionally substituted with one or more independently selected halo; or $C_{1-4}$ alkoxy optionally substituted with one or more independently selected halo;

$C_{1-4}$ alkoxy optionally substituted with one or more independently selected halo; or 4-6 membered monocyclic heterocycle comprising 1 or 2 heteroatoms independently selected from the group consisting of O, S, and N; wherein the monocyclic heterocycle is optionally substituted with one or more independently selected $R^5$ groups;

each $R^{8a}$ and $R^{8b}$ is independently selected from the group consisting of H; and $C_{1-4}$ alkyl;

$R^{9a}$ and $R^{9b}$ are independently selected from the group consisting of

H;

$C_{1-4}$ alkyl; and $C_{3-7}$ cycloalkyl; and each $R^{10}$ is independently selected from the group consisting of $C_{1-6}$ alkyl; and phenyl. In certain embodiments of Formula I-b, $X^1$ is H, halo, optionally substituted cyclopropyl, or optionally substituted phenyl.

In certain embodiments of Formula I-b, $X^1$ is H, halo, or unsubstituted cyclopropyl.

In certain embodiments of Formula I-b, $X^1$ is H.

In certain embodiments of Formula I-b, $X^1$ is bromo, —$NR^{12A}R^{12B}$, alkoxy, cyclopropyl, phenoxy, or phenyl; wherein the cyclopropyl, phenoxy, and phenyl are optionally substituted with 1, 2, or 3 independently selected $R^5$ groups, and the $C_{1-4}$ alkoxy is optionally substituted with one or more independently selected —OH, $C_{1-4}$ alkoxy, or —$NR^{11A}R^{11B}$. In some such embodiments of Formula I-b, the cyclopropyl is unsubstituted. In some such embodiments of Formula I-b, the phenyl and phenoxy are substituted with F.

In certain embodiments of Formula I-b, $X^1$ is bromo, cyclopropyl, or phenyl; wherein the cyclopropyl and the phenyl are optionally substituted with 1, 2, or 3 independently selected $R^5$ groups. In some such embodiments of Formula I-b, the cyclopropyl is unsubstituted.

In certain embodiments of Formula I-b, $X^1$ is bromo.

In certain embodiments of Formula I-b, $X^1$ is cyclopropyl, or phenyl; wherein the cyclopropyl and the phenyl are optionally substituted with 1, 2, or 3 independently selected $R^5$ groups. In some such embodiments of Formula I-b, the cyclopropyl is unsubstituted.

In certain embodiments of Formula I-b, $X^1$ is cyclopropyl, phenoxy, or phenyl; wherein the cyclopropyl, phenoxy, and phenyl are optionally substituted with 1, 2, or 3 independently selected $R^5$ groups. In some such embodiments of Formula I-b, the cyclopropyl is unsubstituted.

In certain embodiments of Formula I-b, $X^1$ is unsubstituted cyclopropyl or phenyl substituted with one fluoro.

In certain embodiments of Formula I-b, $X^1$ is unsubstituted cyclopropyl or phenyl substituted with one fluoro, or phenoxy substituted with one fluoro.

In certain embodiments of Formula I-b, $X^1$ is unsubstituted cyclopropyl.

In certain embodiments of Formula I-b, $X^1$ is phenyl substituted with one fluoro.

In certain embodiments of Formula I-b, $X^1$ is phenoxy substituted with one fluoro.

In certain embodiments of Formula I-b, $X^1$ is $C_{1-4}$ alkoxy optionally substituted with one or more independently selected —OH, $C_{1-4}$ alkoxy, or —$NR^{11A}R^{11B}$ In some such embodiments of Formula I-b, $R^{11A}$ and $R^{11B}$ are H or $C_{1-4}$ alkyl. In some such embodiments of Formula I-b, $R^{11A}$ and $R^{11B}$ are both —CH$_3$.

In certain embodiments of Formula I-b, $X^1$ is $C_{1-4}$ alkoxy which is unsubstituted. In some such embodiments of Formula I-b, $X^1$ is —OCH$_3$.

In certain embodiments of Formula I-b, $X^1$ is $C_{1-4}$ alkoxy which is substituted with $C_{1-4}$ alkoxy. In some such embodiments of Formula I-b, $X^1$ is —OCH$_2$CH$_2$OCH$_3$.

In certain embodiments of Formula I-b, $X^1$ is $C_{1-4}$ alkoxy which is substituted with —$NR^{11A}R^{11B}$. In some such embodiments of Formula I-b, $R^{11A}$ and $R^{11B}$ are H or $C_{1-4}$ alkyl. In some such embodiments of Formula I-b, $R^{11A}$ and $R^{11B}$ are both —CH$_3$.

In certain embodiments of Formula I-b, $X^1$ is —$NR^{12A}R^{12B}$. In some such embodiments of Formula I-b, $R^{12A}$ and $R^{12B}$ are H, $C_{1-4}$ alkyl, or $C_{3-7}$ cycloalkyl. In some such embodiments of Formula I-b, $R^{12A}$ and $R^{12B}$ are both —CH$_3$. In some such embodiments of Formula I-b, $R^{12A}$ is H and $R^{12B}$ is cyclopropyl.

In one embodiment, the invention is directed to compounds of Formula I-b wherein
X¹ is
H;
R¹ is
phenyl optionally substituted with one or more independently selected R⁴ groups;
R² is 5-6 membered monocyclic heteroaryl comprising 1, 2, or 3 heteroatoms independently selected from the group consisting of O, S, and N, wherein the monocyclic heteroaryl is optionally substituted with one or more independently selected R³ groups;
each R³ is independently
$C_{1-4}$ alkyl optionally substituted with one or more independently selected
—OH;
halo; or
—OP(O)(OH)(OH); and
each R⁴ is independently
$C_{1-4}$ alkoxy optionally substituted with one or more independently selected halo.

In one embodiment, the invention is directed to compounds of Formula I-b wherein
X¹ is
H;
R¹ is
phenyl optionally substituted with one or more independently selected R⁴ groups;
R² is 5 membered monocyclic heteroaryl comprising 1, 2, or 3 heteroatoms independently selected from the group consisting of O, S, and N, wherein the monocyclic heteroaryl is optionally substituted with one or more independently selected R³ groups;
each R³ is independently:
$C_{1-4}$ alkyl optionally substituted with one or more independently selected
—OH;
halo; or
—OP(O)(OH)(OH); and
each R⁴ is independently
$C_{1-4}$ alkoxy optionally substituted with one or more independently selected halo.

In one embodiment, the invention is directed to compounds of Formula I-b wherein
X¹ is
H;
R¹ is
phenyl optionally substituted with one or more independently selected R⁴ groups;
R² is oxadiazolyl or thiazolyl comprising 1, 2, or 3 heteroatoms independently selected from the group consisting of O, S, and N, wherein the oxadiazolyl and thiazolyl are optionally substituted with one or more independently selected R³ groups;
each R³ is independently:
$C_{1-4}$ alkyl optionally substituted with one or more independently selected
—OH;
halo; or
—OP(O)(OH)(OH); and
each R⁴ is independently
$C_{1-4}$ alkoxy optionally substituted with one or more independently selected halo.

Various embodiments of substituents X¹, X², R¹, and R² have been discussed above. These substituent's embodiments can be combined to form various embodiments of the invention. All embodiments of present compounds, formed by combining the substituent embodiments discussed above are within the scope of Applicant's invention.

Exemplary compounds of Formula I include, but are not limited to:
(5-{3-amino-5-[4-(trifluoromethoxy)benzene-1-sulfonyl]pyridin-2-yl}-1,3,4-oxadiazol-2-yl)methanol;
(5-{3-amino-5-[4-(trifluoromethoxy)benzene-1-sulfonyl]pyridin-2-yl}-1,3,4-oxadiazol-2-yl)methyldihydrogenphosphate;
2-(5-{3-amino-5-[4-(trifluoromethoxy)benzene-1-sulfonyl]pyridin-2-yl}-1,3,4-oxadiazol-2-yl)-1,1,1-trifluoropropan-2-ol;
1-(5-{3-amino-5-[4-(trifluoromethoxy)benzene-1-sulfonyl]pyridin-2-yl}-1,3,4-oxadiazol-2-yl)-2,2,2-trifluoroethan-1-ol;
(2-{3-amino-5-[4-(trifluoromethoxy)benzene-1-sulfonyl]pyridin-2-yl}-1,3-thiazol-5-yl)methanol;
2-(1,3,4-oxadiazol-2-yl)-5-[4-(trifluoromethoxy)benzene-1-sulfonyl]pyridin-3-amine; (5-{3-amino-5-[4-(trifluoromethyl)benzene-1-sulfonyl]pyridin-2-yl}-1,3,4-oxadiazol-2-yl)methanol;
5-{3-amino-5-[4-(trifluoromethoxy)benzene-1-sulfonyl]pyridin-2-yl}-1,3,4-oxadiazole-2-carboxamide;
{5-[3-amino-5-(4-fluorobenzene-1-sulfonyl)pyridin-2-yl]-1,3,4-oxadiazol-2-yl}methanol;
2-(5-cyclohexyl-1,3,4-oxadiazol-2-yl)-5-[4-(trifluoromethoxy)benzene-1-sulfonyl]pyridin-3-amine;
2-{5-[(S)-methoxy(phenyl)methyl]-1,3,4-oxadiazol-2-yl}-5-[4-(trifluoromethoxy)benzene-1-sulfonyl]pyridin-3-amine;
2-{5-[(cyclopropylmethoxy)methyl]-1,3,4-oxadiazol-2-yl}-5-[4-(trifluoromethoxy)benzene-1-sulfonyl]pyridin-3-amine;
2-[5-(phenoxymethyl)-1,3,4-oxadiazol-2-yl]-5-[4-(trifluoromethoxy)benzene-1-sulfonyl]pyridin-3-amine;
2-{5-[(cyclopentyloxy)methyl]-1,3,4-oxadiazol-2-yl}-5-[4-(trifluoromethoxy)benzene-1-sulfonyl]pyridin-3-amine;
5-[4-(trifluoromethoxy)benzene-1-sulfonyl]-2-{5-[(trifluoromethoxy)methyl]-1,3,4-oxadiazol-2-yl}pyridin-3-amine;
2-(5-{[(oxolan-3-yl)oxy]methyl}-1,3,4-oxadiazol-2-yl)-5-[4-(trifluoromethoxy)benzene-1-sulfonyl]pyridin-3-amine;
2-{5-[(2-methoxyethoxy)methyl]-1,3,4-thiadiazol-2-yl}-5-[4-(trifluoromethoxy)benzene-1-sulfonyl]pyridin-3-amine;
N-[(5-{3-amino-5-[4-(trifluoromethoxy)benzene-1-sulfonyl]pyridin-2-yl}-1,3,4-thiadiazol-2-yl)methyl]cyclopropanecarbothioamide;
2-{5-[(S)-methoxy(phenyl)methyl]-1,3,4-thiadiazol-2-yl}-5-[4-(trifluoromethoxy)benzene-1-sulfonyl]pyridin-3-amine;
(2S)-2-(5-{3-amino-5-[4-(trifluoromethoxy)benzene-1-sulfonyl]pyridin-2-yl}-1,3,4-thiadiazol-2-yl)-1, 1, 1-trifluoropropan-2-ol;
2-{5-[(1R)-1-methoxyethyl]-1,3,4-thiadiazol-2-yl}-5-[4-(trifluoromethoxy)benzene-1-sulfonyl]pyridin-3-amine;
2-[5-(1-methoxyethyl)-1,3,4-thiadiazol-2-yl]-5-[4-(trifluoromethoxy)benzene-1-sulfonyl]pyridin-3-amine;
2-{5-[(1 S)-1-methoxyethyl]-1,3,4-thiadiazol-2-yl}-5-[4-(trifluoromethoxy)benzene-1-sulfonyl]pyridin-3-amine;
2-{5-[(cyclopropylmethoxy)methyl]-1,3,4-thiadiazol-2-yl}-5-[4-(trifluoromethoxy)benzene-1-sulfonyl]pyridin-3-amine;
2-[5-(ethoxymethyl)-1,3,4-thiadiazol-2-yl]-5-[4-(trifluoromethoxy)benzene-1-sulfonyl]pyridin-3-amine;

2-[5-(methoxymethyl)-1,3,4-thiadiazol-2-yl]-5-[4-(trifluoromethoxy)benzene-1-sulfonyl]pyridin-3-amine;
2-(5-{[(pyridin-3-yl)oxy]methyl}-1,3,4-thiadiazol-2-yl)-5-[4-(trifluoromethoxy)benzene-1-sulfonyl]pyridin-3-amine;
5-[4-(trifluoromethoxy)benzene-1-sulfonyl]-2-{5-[(trifluoromethoxy)methyl]-1,3,4-thiadiazol-2-yl}pyridin-3-amine;
2-(5-{[(oxolan-3-yl)oxy]methyl}-1,3,4-thiadiazol-2-yl)-5-[4-(trifluoromethoxy)benzene-1-sulfonyl]pyridin-3-amine;
2-{5-[(difluoromethoxy)methyl]-1,3,4-thiadiazol-2-yl}-5-[4-(trifluoromethoxy)benzene-1-sulfonyl]pyridin-3-amine;
2-(5-{[(2S)-oxolan-2-yl]methyl}-1,3,4-thiadiazol-2-yl)-5-[4-(trifluoromethoxy)benzene-1-sulfonyl]pyridin-3-amine;
2-(5-{[(2R)-oxolan-2-yl]methyl}-1,3,4-thiadiazol-2-yl)-5-[4-(trifluoromethoxy)benzene-1-sulfonyl]pyridin-3-amine;
2-{5-[(2-methoxyethoxy)methyl]-1,3,4-oxadiazol-2-yl}-5-[4-(trifluoromethoxy)benzene-1-sulfonyl]pyridin-3-amine;
2-{5-[(1R)-1-methoxyethyl]-1,3,4-oxadiazol-2-yl}-5-[4-(trifluoromethoxy)benzene-1-sulfonyl]pyridin-3-amine;
2-{5-[(1 S)-1-methoxyethyl]-1,3,4-oxadiazol-2-yl}-5-[4-(trifluoromethoxy)benzene-1-sulfonyl]pyridin-3-amine;
2-[5-(ethoxymethyl)-1,3,4-oxadiazol-2-yl]-5-[4-(trifluoromethoxy)benzene-1-sulfonyl]pyridin-3-amine;
2-[5-(methoxymethyl)-1,3,4-oxadiazol-2-yl]-5-[4-(trifluoromethoxy)benzene-1-sulfonyl]pyridin-3-amine;
2-(5-{[(pyridin-3-yl)oxy]methyl}-1,3,4-oxadiazol-2-yl)-5-[4-(trifluoromethoxy)benzene-1-sulfonyl]pyridin-3-amine;
2-{5-[(difluoromethoxy)methyl]-1,3,4-oxadiazol-2-yl}-5-[4-(trifluoromethoxy)benzene-1-sulfonyl]pyridin-3-amine;
2-(5-{[(2S)-oxolan-2-yl]methyl}-1,3,4-oxadiazol-2-yl)-5-[4-(trifluoromethoxy)benzene-1-sulfonyl]pyridin-3-amine;
2-(5-{[(2R)-oxolan-2-yl]methyl}-1,3,4-oxadiazol-2-yl)-5-[4-(trifluoromethoxy)benzene-1-sulfonyl]pyridin-3-amine;
1-(5-{3-amino-5-[4-(trifluoromethoxy)benzene-1-sulfonyl]pyridin-2-yl}-1,3,4-oxadiazol-2-yl)ethan-1-ol;
2-(5-{3-amino-5-[4-(trifluoromethoxy)benzene-1-sulfonyl]pyridin-2-yl}-1,3,4-oxadiazol-2-yl)propan-2-ol;
(1S)-1-(5-{3-amino-5-[4-(trifluoromethoxy)benzene-1-sulfonyl]pyridin-2-yl}-1,3,4-oxadiazol-2-yl)-2-phenylethan-1-ol;
(S)-(5-{3-amino-5-[4-(trifluoromethoxy)benzene-1-sulfonyl]pyridin-2-yl}-1,3,4-oxadiazol-2-yl)(phenyl)methanol;
2-[3-(2-methoxypropan-2-yl)-1,2,4-oxadiazol-5-yl]-5-[4-(trifluoromethoxy)benzene-1-sulfonyl]pyridin-3-amine;
2-[3-(1-methoxyethyl)-1,2,4-oxadiazol-5-yl]-5-[4-(trifluoromethoxy)benzene-1-sulfonyl]pyridin-3-amine;
2-[3-(oxan-4-yl)-1,2,4-oxadiazol-5-yl]-5-[4-(trifluoromethoxy)benz ene-1-sulfonyl]pyridin-3-amine;
2-{3-[(4-fluorophenoxy)methyl]-1,2,4-oxadiazol-5-yl}-5-[4-(trifluoromethoxy)benzene-1-sulfonyl]pyridin-3-amine;
2-[3-(cyclopropylmethyl)-1,2,4-oxadiazol-5-yl]-5-[4-(trifluoromethoxy)benzene-1-sulfonyl]pyridin-3-amine;
2-{3-[(oxolan-2-yl)methyl]-1,2,4-oxadiazol-5-yl}-5-[4-(trifluoromethoxy)benzene-1-sulfonyl]pyridin-3-amine;
2-(3-cyclopropyl-1,2,4-oxadiazol-5-yl)-5-[4-(trifluoromethoxy)benz ene-1-sulfonyl]pyridin-3-amine;
2-[3-(oxolan-3-yl)-1,2,4-oxadiazol-5-yl]-5-[4-(trifluoromethoxy)benzene-1-sulfonyl]pyridin-3-amine;
2-(3-tert-butyl-1,2,4-oxadiazol-5-yl)-5-[4-(trifluoromethoxy)benzene-1-sulfonyl]pyridin-3-amine;
2-[3-(2-methoxyethyl)-1,2,4-oxadiazol-5-yl]-5-[4-(trifluoromethoxy)benzene-1-sulfonyl]pyridin-3-amine;
2-[3-(methoxymethyl)-1,2,4-oxadiazol-5-yl]-5-[4-(trifluoromethoxy)benzene-1-sulfonyl]pyridin-3-amine;
(5-{3-amino-4-chloro-5-[4-(trifluoromethoxy)benzene-1-sulfonyl]pyridin-2-yl}-1,3,4-oxadiazol-2-yl)methanol;
(5-{3-amino-5-[3-(trifluoromethoxy)benzene-1-sulfonyl]pyridin-2-yl}-1,3,4-oxadiazol-2-yl)methanol;
(5-{3-amino-5-[2-(trifluoromethoxy)benzene-1-sulfonyl]pyridin-2-yl}-1,3,4-oxadiazol-2-yl)methanol;
5-amino-N-benzyl-6-[5-(hydroxymethyl)-1,3,4-oxadiazol-2-yl]-N-methylpyridine-3-sulfonamide;
{5-[3-amino-5-(benzenesulfonyl)pyridin-2-yl]-1,3,4-oxadiazol-2-yl}methanol;
(5-{3-amino-5-[4-(trifluoromethyl)benzene-1-sulfonyl]pyridin-2-yl}-1,3,4-thiadiazol-2-yl)methanol;
(5-{3-amino-6-bromo-5-[4-(trifluoromethoxy)benzene-1-sulfonyl]pyridin-2-yl}-1,3,4-oxadiazol-2-yl)methanol;
(5-{3-amino-6-chloro-5-[4-(trifluoromethoxy)benzene-1-sulfonyl]pyridin-2-yl}-1,3,4-oxadiazol-2-yl)methanol;
(5-{3-amino-5-[2-(propan-2-yl)benzene-1-sulfonyl]pyridin-2-yl}-1,3,4-oxadiazol-2-yl)methanol;
(5-{3-amino-4-bromo-5-[4-(trifluoromethoxy)benzene-1-sulfonyl]pyridin-2-yl}-1,3,4-oxadiazol-2-yl)methanol;
2-(5-{3-amino-5-[4-(trifluoromethoxy)benzene-1-sulfonyl]pyridin-2-yl}-1,2,4-oxadiazol-3-yl)ethan-1-ol; and pharmaceutically acceptable salts thereof.

Compounds of the invention were named by using Name 2015 naming algorithm by Advanced Chemical Development or Struct=Name naming algorithm as part of CHEMDRAW® Professional Version 15.0.0.106.

Compounds of the invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furnis, Hannaford, Smith, and Tatchell, "Vogel's Textbook of Practical Organic Chemistry", 5th edition (1989), Longman Scientific & Technical, Essex CM20 27E, England, or (2) direct separation of the mixture of optical enantiomers on chiral chromatographic columns or (3) fractional recrystallization methods.

Compounds of the invention may exist as cis or trans isomers, wherein substituents on a ring may attached in such a manner that they are on the same side of the ring (cis)

relative to each other, or on opposite sides of the ring relative to each other (trans). For example, cyclobutane may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well-known to those of ordinary skill in the art, and may include separation of isomers by recrystallization or chromatography.

It should be understood that the compounds of the invention may possess tautomeric forms, as well as geometric isomers, and that these also constitute an aspect of the invention.

The present disclosure includes all pharmaceutically acceptable isotopically-labelled compounds of Formula I and I-a wherein one or more atoms are replaced by atoms having the same atomic number, but an atomic mass or mass number different from the atomic mass or mass number which predominates in nature. Examples of isotopes suitable for inclusion in the compounds of the disclosure include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S. Certain isotopically-labelled compounds of Formula I, I-a, and I-b for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labelled compounds of Formula I, I-a, and I-b may generally be prepared by conventional techniques known to those skilled in the art or by processes analogous to those described in the accompanying Examples using an appropriate isotopically-labelled reagents in place of the non-labelled reagent previously employed.

Thus, the formula drawings within this specification can represent only one of the possible tautomeric, geometric, or stereoisomeric forms. It is to be understood that the invention encompasses any tautomeric, geometric, or stereoisomeric form, and mixtures thereof, and is not to be limited merely to any one tautomeric, geometric, or stereoisomeric form utilized within the formula drawings.

Compounds of Formula I, I-a, and I-b may be used in the form of pharmaceutically acceptable salts. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts have been described in S. M. Berge et al. J. Pharmaceutical Sciences, 1977, 66: 1-19.

Compounds of Formula I, I-a, and I-b may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid, and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

Compounds described herein may exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

Pharmaceutical Compositions

When employed as a pharmaceutical, a compound of the invention is typically administered in the form of a pharmaceutical composition. In one embodiment, such compositions can be prepared in a manner well known in the pharmaceutical art and comprise a therapeutically effective amount of a compound of Formula I, I-a, I-b, or a pharmaceutically acceptable salt thereof, together with a pharmaceutically acceptable carrier. The phrase "pharmaceutical composition" refers to a composition suitable for administration in medical or veterinary use.

The pharmaceutical compositions that comprise a compound of Formula I, I-a, or I-b, alone or in combination with further therapeutically active ingredient, may be administered to the subjects orally, rectally, parenterally, intracisternally, intravaginally, intraperitoneally, topically (as by powders, ointments or drops), buccally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which may serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants may also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous diluents, solvents, or vehicles include water, ethanol, polyols (such as glycerol, propylene glycol, polyethylene glycol and the like), vegetable oils (such as olive oil), injectable organic esters (such as ethyl oleate), and suitable mixtures thereof. Proper fluidity may be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

In some cases, in order to prolong the effect of the drug, it may be desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release may be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations may be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In certain embodiments, solid dosage forms may contain from 1% to 95% (w/w) of a compound of Formula I, I-a, or I-b. In certain embodiments, the compound of Formula I, I-a, or I-b, or pharmaceutically acceptable salts thereof, may be present in the solid dosage form in a range of from 5% to 70% (w/w). In such solid dosage forms, the active compound may be mixed with at least one inert, pharmaceutically acceptable carrier, such as sodium citrate or dicalcium phosphate and/or a), fillers or extenders such as starches, lactose, sucrose, glucose, mannitol, and silicic acid; b) binders such as carboxymethylcellulose, alginates, gelatin, polyvinylpyrrolidone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form may be a capsule, tablet, cachet, or lozenge itself, or it may be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition may, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician may evaluate factors such as the circulating plasma levels of the compound, compound toxicities, and/or the progression of the disease, etc.

For administration, compounds may be administered at a rate determined by factors that may include, but are not limited to, the LD50 of the compound, the pharmacokinetic profile of the compound, contraindicated drugs, and the side-effects of the compound at various concentrations, as applied to the mass and overall health of the subject. Administration may be accomplished via single or divided doses.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds may also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols, and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which may be prepared by mixing the compounds with suitable non-irritating carriers or carriers such as cocoa butter, polyethylene glycol, or a suppository wax which are solid at room temperature but liquid at body temperature and therefore melt in the rectum or vaginal cavity and release the active compound.

Compounds may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes may be used. The present compositions in liposome form may contain, in addition to a compound of the invention, stabilizers, preservatives, excipients, and the like. Examples of lipids include, but are not limited to, natural and synthetic phospholipids, and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments, and inhalants. The active compound may be mixed under sterile conditions with a pharmaceutically acceptable carrier and any needed preservatives, buffers or propellants which may be required. Ophthalmic formulations, eye ointments, powders and solutions are also contemplated as being within the scope of this invention.

A compound of the invention may also be administered in sustained release forms or from sustained release drug delivery systems.

Methods of Use

The compounds and compositions using any amount and any route of administration may be administered to a subject for the treatment or prevention of cystic fibrosis, pancreatic insufficiency, Sjögren's Syndrome (SS), chronic obstructive lung disease (COLD), or chronic obstructive airway disease (COAD).

The term "administering" refers to the method of contacting a compound with a subject. Thus, the compounds may be administered by injection, that is, intravenously, intramuscularly, intracutaneously, subcutaneously, intraduodenally, parentally, or intraperitoneally. Also, the compounds described herein may be administered by inhalation, for example, intranasally. Additionally, the compounds may be administered transdermally, topically, via implantation, transdermally, topically, and via implantation. In certain embodiments, the compounds and compositions thereof may be delivered orally. The compounds may also be delivered rectally, buccally, intravaginally, ocularly, or by insufflation. CFTR-modulated disorders and conditions may be treated prophylactically, acutely, and chronically using compounds and compositions thereof, depending on the nature of the disorder or condition. Typically, the host or subject in each of these methods is human, although other mammals may also benefit from the administration of compounds and compositions thereof as set forth hereinabove.

Compounds of the invention are useful as modulators of CFTR. Thus, the compounds and compositions are particularly useful for treating or lessening the severity or progression of a disease, disorder, or a condition where hyperactivity or inactivity of CFTR is involved. Accordingly, the invention provides a method for treating cystic fibrosis, pancreatic insufficiency, Sjögren's Syndrome (SS), chronic obstructive lung disease (COLD), or chronic obstructive airway disease (COAD) in a subject, wherein the method comprises the step of administering to said subject a therapeutically effective amount of a compound of Formula I, I-a, or I-b or a preferred embodiment thereof as set forth above, with or without a pharmaceutically acceptable carrier. Particularly, the method is for the treatment or prevention of cystic fibrosis. In a more particular embodiment, the cystic fibrosis is caused by a Class I, II, III, IV, V, and/or VI mutation.

In another embodiment, the present invention provides compounds of the invention, or pharmaceutical compositions comprising a compound of the invention for use in medicine. In a particular embodiment, the present invention provides compounds of the invention, or a pharmaceutically acceptable salt thereof, or a pharmaceutical composition comprising a compound of the invention, for use in medicine. In a particular embodiment, the present invention provides compounds of the invention or pharmaceutical compositions comprising a compound of the invention, for use in the treatment of cystic fibrosis, pancreatic insufficiency, Sjögren's Syndrome (SS), chronic obstructive lung disease (COLD) or chronic obstructive airway disease (COAD). In a more particular embodiment, the present invention provides compounds of the invention or pharmaceutical compositions comprising a compound of the invention, for use in the treatment of cystic fibrosis. In a more particular embodiment, the cystic fibrosis is caused by a Class I, II, III, IV, V, and/or VI mutation.

One embodiment is directed to the use of a compound according to Formula I, I-a or I-b, or a pharmaceutically acceptable salt thereof, in the preparation of a medicament. The medicament optionally can comprise one or more additional therapeutic agents. In some embodiments, the medicament is for use in the treatment of cystic fibrosis, pancreatic insufficiency, Sjögren's Syndrome (SS), chronic obstructive lung disease (COLD) or chronic obstructive airway disease (COAD). In a particular embodiment, the medicament is for use in the treatment of cystic fibrosis. In a more particular embodiment, the cystic fibrosis is caused by a Class I, II, III, IV, V, and/or VI mutation.

This invention also is directed to the use of a compound according to Formula I, I-a or I-b, or a pharmaceutically acceptable salt thereof, in the manufacture of a medicament for the treatment of cystic fibrosis, Sjögren's syndrome, pancreatic insufficiency, chronic obstructive lung disease, and chronic obstructive airway disease. The medicament optionally can comprise one or more additional therapeutic agents. In a particular embodiment, the invention is directed to the use of a compound according to Formula I, or a pharmaceutically acceptable salt thereof, in the manufacture of a medicament for the treatment of cystic fibrosis. In a more particular embodiment, the cystic fibrosis is caused by a Class I, II, III, IV, V, and/or VI mutation.

In one embodiment, the present invention provides pharmaceutical compositions comprising a compound of the invention, or a pharmaceutically acceptable salt thereof, and one or more additional therapeutic agents. In another embodiment, the present invention provides pharmaceutical compositions comprising a compound of the invention, or a pharmaceutically acceptable salt thereof, and one or more additional therapeutic agents wherein the additional therapeutic agents are selected from the group consisting of CFTR modulators and CFTR amplifiers. In another embodiment, the present invention provides pharmaceutical compositions comprising a compound of the invention, or a pharmaceutically acceptable salt thereof, and one or more additional therapeutic agents wherein the additional therapeutic agents are CFTR modulators.

In one embodiment, the present invention provides pharmaceutical compositions comprising a compound of the invention, or a pharmaceutically acceptable salt thereof, and one or more additional therapeutic agents. In one embodiment, the present invention provides pharmaceutical compositions comprising a compound of the invention, or a pharmaceutically acceptable salt thereof, and one or more correctors. In one embodiment, the present invention provides pharmaceutical compositions comprising a compound of the invention, and another therapeutic agent. In a particular embodiment, the other therapeutic agent is a cystic fibrosis treatment agent. In one embodiment, the present invention provides a method for treating cystic fibrosis in a subject comprising administering a therapeutically effective amount of a compound of the invention, or a pharmaceutically acceptable salt thereof. In one embodiment, the present invention provides a method for treating cystic fibrosis in a subject comprising administering a compound of the invention, or a pharmaceutically acceptable salt thereof, and one or more additional therapeutic agents. In another embodiment, the present invention provides a method for treating cystic fibrosis in a subject comprising administering a compound of the invention, or a pharmaceutically acceptable salt thereof, and one or more additional therapeutic agents wherein the additional therapeutic agents are selected from the group consisting of CFTR modulators and CFTR amplifiers. In one embodiment, the present invention provides a method for treating cystic fibrosis in a subject comprising administering a compound of the invention, or a pharmaceutically acceptable salt thereof, and one or more additional therapeutic agents wherein the additional therapeutic agents are CFTR modulators. In one embodiment, the present invention provides a method for treating cystic fibrosis in a subject comprising administering a compound of the invention, or a pharmaceutically acceptable salt thereof, and, and another therapeutic agent. In a particular embodiment, the other therapeutic agent is a cystic fibrosis treatment agent. In a particular embodiment, the additional therapeutic agent(s) is selected from the group consisting of CFTR modulators and CFTR amplifiers. In a particular embodiment, the additional therapeutic agent(s) are one or more correctors. In another embodiment, the other therapeutic agent(s) is a CFTR modulator. In a more particular embodiment, the cystic fibrosis is caused by a Class I, II, III, IV, V and/or VI mutation.

The present compounds or pharmaceutically acceptable salts thereof may be administered as the sole active agent or it may be co-administered with other therapeutic agents, including other compounds or a pharmaceutically acceptable salt thereof that demonstrate the same or a similar therapeutic activity and that are determined to be safe and efficacious for such combined administration. The present compounds may be co-administered to a subject. The term "co-administered" means the administration of two or more different therapeutic agents to a subject in a single pharmaceutical composition or in separate pharmaceutical compositions. Thus co-administration involves administration at the same time of a single pharmaceutical composition comprising two or more therapeutic agents or administration of two or more different compositions to the same subject at the same or different times.

The compounds of the invention or pharmaceutically acceptable salts thereof may be co-administered with a therapeutically effective amount of one or more additional therapeutic agents to treat a CFTR mediated disease, where examples of the therapeutic agents include, but are not limited to antibiotics (for example, aminoglycosides, colistin, aztreonam, ciprofloxacin, and azithromycin), expectorants (for example, hypertonic saline, acetylcysteine, dornase alfa, and denufosol), pancreatic enzyme supplements (for example, pancreatin, and pancrelipase), epithelial sodium channel blocker (ENaC) inhibitors, CFTR modulators (for example, CFTR potentiators, CFTR correctors), and CFTR amplifiers. In one embodiment, the CFTR mediated disease is cystic fibrosis, chronic obstructive pulmonary disease (COPD), dry eye disease, pancreatic insufficiency, or Sjögren's syndrome. In one embodiment, the CFTR mediated disease is cystic fibrosis.

In one embodiment, the compounds of the invention or pharmaceutically acceptable salts thereof may be co-administered with one or two CFTR modulators and one CFTR amplifier. In one embodiment, the compounds of the invention or pharmaceutically acceptable salts thereof may be co-administered with one potentiator, one or more correctors, and one CFTR amplifier. In one embodiment, the compounds of the invention or pharmaceutically acceptable salts thereof may be co-administered with one or more CFTR modulators. In one embodiment, the compounds of the invention or pharmaceutically acceptable salts thereof may be co-administered with one CFTR modulator. In one embodiment, the compounds of the invention or pharmaceutically acceptable salts thereof may be co-administered with two CFTR modulators. In one embodiment, the compounds of the invention or pharmaceutically acceptable salts thereof may be co-administered with three CFTR modulators. In one embodiment, the compounds of the invention or pharmaceutically acceptable salts thereof may be co-administered with one potentiator and one or more correctors. In one embodiment, the compounds of the invention or pharmaceutically acceptable salts thereof may be co-administered with one potentiator and two correctors. In one embodiment, the compounds of the invention or pharmaceutically acceptable salts thereof may be co-administered with one potentiator. In one embodiment, the compounds of the invention or pharmaceutically acceptable salts thereof may be co-administered with one or more correctors. In one embodiment, the compounds of the invention or pharmaceutically acceptable salts thereof may be co-administered with one corrector. In one embodiment, the compounds of the invention or pharmaceutically acceptable salts thereof may be co-administered two correctors. In one embodiment, the compounds of the invention or pharmaceutically acceptable salts thereof may be co-administered with one or more correctors, and one amplifier. In one embodiment, the compounds of the invention or pharmaceutically acceptable salts thereof may be co-administered with one corrector, and one amplifier. In one embodiment, the compounds of the invention or pharmaceutically acceptable salts thereof may be co-administered with two correctors, and one amplifier. In one embodiment, the compounds of the invention or pharmaceutically acceptable salts thereof may be co-administered with one corrector. In one embodiment, the compounds of the invention or pharmaceutically acceptable salts thereof may be co-administered with two correctors.

Examples of CFTR potentiators include, but are not limited to, Ivacaftor (VX-770), CTP-656, NVS-QBW251, FD1860293, PTI-808, N-(3-carbamoyl-5,5,7,7-tetramethyl-5,7-dihydro-4H-thieno[2,3-c]pyran-2-yl)-1H-pyrazole-5-carboxamide, and 3-amino-N-[(2S)-2-hydroxypropyl]-5-{[4-(trifluoromethoxy)phenyl]sulfonyl}pyridine-2-carboxamide. Examples of potentiators are also disclosed in publications: WO2005120497, WO2008147952, WO2009076593, WO2010048573, WO2006002421, WO2008147952, WO2011072241, WO2011113894, WO2013038373, WO2013038378, WO2013038381, WO2013038386, and WO2013038390; and U.S. application Ser. Nos. 14/271,080, 14/451,619 and 15/164,317.

In one embodiment, the potentiator can be selected from the group consisting of

Ivacaftor (VX-770, N-(2,4-di-tert-butyl-5-hydroxyphenyl)-4-oxo-1,4-dihydroquinoline-3-carboxamide);
CTP-656;
NVS-QBW251;
FD1860293;
PTI-808;
2-(2-fluorobenzamido)-5,5,7,7-tetramethyl-5,7-dihydro-4H-thieno[2,3-c]pyran-3-carboxamide;
N-(3-carbamoyl-5,5,7,7-tetramethyl-5,7-dihydro-4H-thieno[2,3-c]pyran-2-yl)-1H-pyrazole-5-carboxamide;
2-(2-hydroxybenzamido)-5,5,7,7-tetramethyl-5,7-dihydro-4H-thieno[2,3-c]pyran-3-carboxamide;
2-(1-hydroxycyclopropanecarboxamido)-5,5,7,7-tetramethyl-5,7-dihydro-4H-thieno[2,3-c]pyran-3-carboxamide;
5,5,7,7-tetramethyl-2-(2-(trifluoromethyl)benzamido)-5,7-dihydro-4H-thieno[2,3-c]pyran-3-carboxamide;
2-(2-hydroxy-2-methylpropanamido)-5,5,7,7-tetramethyl-5,7-dihydro-4H-thieno[2,3-c]pyran-3-carboxamide;
2-(1-(hydroxymethyl)cyclopropanecarboxamido)-5,5,7,7-tetramethyl-5,7-dihydro-4H-thieno[2,3-c]pyran-3-carboxamide;
2-(3-hydroxy-2,2-dimethylpropanamido)-5,5,7,7-tetramethyl-5,7-dihydro-4H-thieno[2,3-c]pyran-3-carboxamide;
N-(3-carbamoyl-5,5,7,7-tetramethyl-5,7-dihydro-4H-thieno[2,3-c]pyran-2-yl)-5-methyl-1H-pyrazole-3-carboxamide;
N-(3-carbamoyl-5,5,7,7-tetramethyl-5,7-dihydro-4H-thieno[2,3-c]pyran-2-yl)-5-cyclopropyl-1H-pyrazole-3-carboxamide;
N-(3-carbamoyl-5,5,7,7-tetramethyl-5,7-dihydro-4H-thieno[2,3-c]pyran-2-yl)-5-isopropyl-1H-pyrazole-3-carboxamide;
N-(3-carbamoyl-5,5,7,7-tetramethyl-5,7-dihydro-4H-thieno[2,3-c]pyran-2-yl)-5-(trifluoromethyl)-1H-pyrazole-3-carboxamide;
5-tert-butyl-N-(3-carbamoyl-5,5,7,7-tetramethyl-5,7-dihydro-4H-thieno[2,3-c]pyran-2-yl)-1H-pyrazole-3-carboxamide;
N-(3-carbamoyl-5,5,7,7-tetramethyl-5,7-dihydro-4H-thieno[2,3-c]pyran-2-yl)-5-ethyl-1H-pyrazole-3-carboxamide;
N-(3-carbamoyl-5,5,7,7-tetramethyl-5,7-dihydro-4H-thieno[2,3-c]pyran-2-yl)-3-ethyl-4-methyl-1H-pyrazole-5-carboxamide;
2-(2-hydroxypropanamido)-5,5,7,7-tetramethyl-5,7-dihydro-4H-thieno[2,3-c]pyran-3-carboxamide;
N-(3-carbamoyl-5,5,7,7-tetramethyl-5,7-dihydro-4H-thieno[2,3-c]pyran-2-yl)-4-chloro-1H-pyrazole-3-carboxamide;
N-(3-carbamoyl-5,5,7,7-tetramethyl-5,7-dihydro-4H-thieno[2,3-c]pyran-2-yl)-1,4,6,7-tetrahydropyrano[4,3-c]pyrazole-3-carboxamide;
4-bromo-N-(3-carbamoyl-5,5,7,7-tetramethyl-5,7-dihydro-4H-thieno[2,3-c]pyran-2-yl)-1H-pyrazole-3-carboxamide;
N-(3-carbamoyl-5,5,7,7-tetramethyl-5,7-dihydro-4H-thieno[2,3-c]pyran-2-yl)-4-chloro-5-methyl-1H-pyrazole-3-carboxamide;
N-(3-carbamoyl-5,5,7,7-tetramethyl-5,7-dihydro-4H-thieno[2,3-c]pyran-2-yl)-4-methyl-1H-pyrazole-3-carboxamide;
2-(2-hydroxy-3,3-dimethylbutanamido)-5,5,7,7-tetramethyl-5,7-dihydro-4H-thieno[2,3-c]pyran-3-carboxamide;
2-[(2-hydroxy-4-methyl-pentanoyl)amino]-5,5,7,7-tetramethyl-4H-thieno[2,3-c]pyran-3-carboxamide;
5-(2-methoxy-ethoxy)-1H-pyrazole-3-carboxylic acid (3-carbamoyl-5,5,7,7-tetramethyl-4,7-dihydro-5H-thieno[2,3-c]pyran-2-yl)-amide;
N-(3-carbamoyl-5,5,7,7-tetramethyl-4H-thieno[2,3-c]pyran-2-yl)-4-(3-methoxypropyl)-1H-pyrazole-3-carboxamide;
N-(3-carbamoyl-5,5,7,7-tetramethyl-4H-thieno[2,3-c]pyran-2-yl)-4-(2-ethoxyethyl)-1H-pyrazole-3-carboxamide;
2-[[(2S)-2-hydroxy-3,3-dimethyl-butanoyl]amino]-5,5,7,7-tetramethyl-4H-thieno[2,3-c]pyran-3-carboxamide;
2-[[(2R)-2-hydroxy-3,3-dimethyl-butanoyl]amino]-5,5,7,7-tetramethyl-4H-thieno[2,3-c]pyran-3-carboxamide;

2-[(2-hydroxy-2,3,3-trimethyl-butanoyl)amino]-5,5,7,7-tetramethyl-4H-thieno[2,3-c]pyran-3-carboxamide;
[5-[(3-carbamoyl-5,5,7,7-tetramethyl-4H-thieno[2,3-c]pyran-2-yl)carbamoyl]pyrazol-1-yl]methyl dihydrogen phosphate;
[3-[(3-carbamoyl-5,5,7,7-tetramethyl-4H-thieno[2,3-c]pyran-2-yl)carbamoyl]pyrazol-1-yl]methyl dihydrogen phosphate;
N-(3-carbamoyl-5,5,7,7-tetramethyl-4H-thieno[2,3-c]pyran-2-yl)-4-(1,4-dioxan-2-yl)-1H-pyrazole-3-carboxamide;
5,5, 7,7-tetramethyl-2-[[(2S)-3,3,3-trifluoro-2-hydroxy-2-methyl-propanoyl]amino]-4H-thieno[2,3-c]pyran-3-carboxamide;
2-[[(2S)-2-hydroxypropanoyl]amino]-5, 5,7, 7-tetramethyl-4H-thieno[2, 3-c]pyran-3-carboxamide;
3-amino-N-(2-hydroxy-2-methylpropyl)-5-{[4-(trifluoromethoxy)phenyl]sulfonyl}pyridine-2-carboxamide;
3-amino-N-[(4-hydroxy-1-methylpiperidin-4-yl)methyl]-5-{[4-(trifluoromethoxy)phenyl]sulfonyl}pyridine-2-carboxamide;
3-amino-N-(3-hydroxy-2,2-dimethylpropyl)-5-{[4-(trifluoromethoxy)phenyl]sulfonyl}pyridine-2-carboxamide;
3-amino-5-[(4-fluorophenyl)sulfonyl]-N-[(1-hydroxycyclopropyl)methyl]pyridine-2-carboxamide;
3-amino-5-[(4-fluorophenyl)sulfonyl]-N-[(2R)-3,3,3-trifluoro-2-hydroxypropyl]pyridine-2-carboxamide;
3-amino-5-[(3-fluorophenyl)sulfonyl]-N-(2-hydroxy-2-methylpropyl)pyridine-2-carboxamide;
3-amino-N-[2-(cyclopropylamino)-2-oxoethyl]-5-{[4-(trifluoromethoxy)phenyl]sulfonyl}pyridine-2-carboxamide;
(3-amino-5-{[4-(trifluoromethoxy)phenyl]sulfonyl}pyridin-2-yl)(azetidin-1-yl)methanone;
(3-amino-5-{[4-(trifluoromethoxy)phenyl]sulfonyl}pyridin-2-yl)[3-(hydroxymethyl)azetidin-1-yl]methanone;
(3-amino-5-{[4-(trifluoromethoxy)phenyl]sulfonyl}pyridin-2-yl)(3-fluoroazetidin-1-yl)methanone;
3-amino-N-[(2R)-2-hydroxy-3-methoxypropyl]-5-{[4-(trifluoromethyl)phenyl]sulfonyl}pyridine-2-carboxamide;
(3-amino-5-{[2-fluoro-4-(trifluoromethoxy)phenyl]sulfonyl}pyridin-2-yl)(3-hydroxyazetidin-1-yl)methanone;
(3-amino-5-{[2-(trifluoromethoxy)phenyl]sulfonyl}pyridin-2-yl)(3,3-difluoroazetidin-1-yl)methanone;
rac-3-amino-N-[(3R,4S)-4-hydroxytetrahydro-2H-pyran-3-yl]-5-{[2-(trifluoromethoxy)phenyl]sulfonyl}pyridine-2-carboxamide;
3-amino-5-[(4,4-difluoropiperidin-1-yl)sulfonyl]-N-(3,3,3-trifluoro-2-hydroxypropyl)pyridine-2-carboxamide;
(3-amino-5-{[2-(trifluoromethoxy)phenyl]sulfonyl}pyridin-2-yl)[3-hydroxy-3-(trifluoromethyl)azetidin-1-yl]methanone;
3-amino-N-(2-hydroxy-4-methylpentyl)-5-{[4-(trifluoromethoxy)phenyl]sulfonyl}pyridine-2-carboxamide;
(3-amino-5-{[4-(trifluoromethyl)phenyl]sulfonyl}pyridin-2-yl)(3-hydroxy-3-methylazetidin-1-yl)methanone;
3-amino-N-(3,3,3-trifluoro-2-hydroxypropyl)-5-{[4-(trifluoromethyl)piperidin-1-yl]sulfonyl}pyridine-2-carboxamide;
3-amino-N-[2-hydroxy-1-(4-methoxyphenyl)ethyl]-5-{[4-(trifluoromethoxy)phenyl]sulfonyl}pyridine-2-carboxamide;
3-amino-5-[(3,3-difluoroazetidin-1-yl)sulfonyl]-N-(3,3,3-trifluoro-2-hydroxypropyl)pyridine-2-carboxamide;

3-amino-5-{[2-fluoro-4-(trifluoromethyl)phenyl]sulfonyl}-N-[(2S)-2-hydroxypropyl]pyridine-2-carboxamide;
3-amino-5-{[2-fluoro-4-(trifluoromethyl)phenyl]sulfonyl}-N-[(2R)-2-hydroxy-3-methoxypropyl]pyridine-2-carboxamide;
3-amino-N-[2-oxo-2-(propan-2-ylamino)ethyl]-5-{[4-(trifluoromethyl)phenyl]sulfonyl}pyridine-2-carboxamide;
(3-amino-5-{[4-(trifluoromethyl)phenyl]sulfonyl}pyridin-2-yl)[3-hydroxy-3-(trifluoromethyl)azetidin-1-yl]methanone;
3-amino-5-{[2-fluoro-4-(trifluoromethyl)phenyl]sulfonyl}-N-[(3R)-tetrahydrofuran-3-ylmethyl]pyridine-2-carboxamide;
(3-amino-5-{[2-fluoro-4-(trifluoromethyl)phenyl]sulfonyl}pyridin-2-yl)[3-hydroxy-3-(trifluoromethyl)azetidin-1-yl]methanone;
3-amino-5-{[2-fluoro-4-(trifluoromethyl)phenyl]sulfonyl}-N-[(3S)-tetrahydrofuran-3-ylmethyl]pyridine-2-carboxamide;
3-amino-5-{[2-fluoro-4-(trifluoromethoxy)phenyl]sulfonyl}-N-[(3S)-tetrahydrofuran-3-ylmethyl]pyridine-2-carboxamide;
3-amino-N-[2-hydroxy-3-(2,2,2-trifluoroethoxy)propyl]-5-{[4-(trifluoromethyl)phenyl]sulfonyl}pyridine-2-carboxamide;
3-amino-N-(3-tert-butoxy-2-hydroxypropyl)-5-{[2-fluoro-4-(trifluoromethyl)phenyl]sulfonyl}pyridine-2-carboxamide;
[3-amino-5-(phenylsulfonyl)pyridin-2-yl][3-hydroxy-3-(trifluoromethyl)azetidin-1-yl]methanone;
{3-amino-5-[(3-fluorophenyl)sulfonyl]pyridin-2-yl}[3-hydroxy-3-(trifluoromethyl)azetidin-1-yl]methanone; and
3-amino-N-[(2S)-2-hydroxypropyl]-5-{[4-(trifluoromethoxy)phenyl]sulfonyl}pyridine-2-carboxamide.

Non-limiting examples of correctors include Lumacaftor (VX-809), 1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropanecarboxamide (VX-661), VX-983, GLPG2222, GLPG2665, GLPG2737, GLPG2851, GLPG3221, PTI-801, VX-152, VX-440, VX-659, VX-445, FDL169, FDL304, FD2052160, and FD2035659. Examples of correctors are also disclosed in U.S. application Ser. Nos. 14/925,649, 14/926,727, 15/205, 512, 15/496,094, 15/287,922 and 15/287,911.

In one embodiment, the corrector(s) can be selected from the group consisting of
Lumacaftor (VX-809);
1-(2,2-difluoro-1,3-benzodioxol-5-yl)-N-{1-[(2R)-2,3-dihydroxypropyl]-6-fluoro-2-(1-hydroxy-2-methylpropan-2-yl)-1H-indol-5-yl}cyclopropanecarboxamide (VX-661);
VX-983;
GLPG2665;
GLPG2737;
GLPG3221;
PTI-801;
VX-152;
VX-440;
VX-659;
VX-445
FDL169
FDL304;
FD2052160;
FD2035659;
3-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-6-methyl-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-6-methoxy-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]cyclohexanecarboxylic acid;

3-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-methoxy-3,4-dihydro-2H-chromen-2-yl]cyclohexanecarboxylic acid;

3-[(2R,4R)-4-({[1-(2,2-difluoro-1,3-benzodioxol-5-yl)cyclopropyl]carbonyl}amino)-7-fluoro-3,4-dihydro-2H-chromen-2-yl]benzoic acid;

3-({3-[(2R,4R)-4-({[1-(2,2-difluoro-1,3-benzodioxol-5-yl)cyclopropyl]carbonyl}amino)-7-methyl-3,4-dihydro-2H-chromen-2-yl]benzoyl}amino)-1-methylcyclopentanecarboxylic acid;

3-[(2R,4R)-4-({[1-(2,2-difluoro-1,3-benzodioxol-5-yl)cyclopropyl]carbonyl}amino)-7-methyl-3,4-dihydro-2H-chromen-2-yl]-N-[(2R)-2,3-dihydroxypropyl]benzamide;

3-[(2R,4R)-4-({[1-(2,2-difluoro-1,3-benzodioxol-5-yl)cyclopropyl]carbonyl}amino)-7-(2-methoxyethoxy)-3,4-dihydro-2H-chromen-2-yl]benzoic acid;

3-[(2R,4R)-7-(benzyloxy)-4-({[1-(2,2-difluoro-1,3-benzodioxol-5-yl)cyclopropyl]carbonyl}amino)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-(2-fluoroethoxy)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-7-(trifluoromethyl)-3,4-dihydro-2H-chromen-2-yl]cyclohexanecarboxylic acid;

4-[(2R,4R)-4-({[1-(2,2-difluoro-1,3-benzodioxol-5-yl)cyclopropyl]carbonyl}amino)-7-methoxy-3,4-dihydro-2H-chromen-2-yl]benzoic acid;

3-[(2R,4R)-4-({[1-(2,2-difluoro-1,3-benzodioxol-5-yl)cyclopropyl]carbonyl}amino)-8-fluoro-3,4-dihydro-2H-chromen-2-yl]benzoic acid;

4-[(2R,4R)-4-({[1-(2,2-difluoro-1,3-benzodioxol-5-yl)cyclopropyl]carbonyl}amino)-3,4-dihydro-2H-chromen-2-yl]benzoic acid;

4-[(2R,4R)-4-({[1-(2,2-difluoro-1,3-benzodioxol-5-yl)cyclopropyl]carbonyl}amino)-7-(difluoromethoxy)-3,4-dihydro-2H-chromen-2-yl]benzoic acid;

rac-3-[(2R,4S)-4-({[1-(2,2-difluoro-1,3-benzodioxol-5-yl)cyclopropyl]carbonyl}amino)tetrahydro-2H-pyran-2-yl]benzoic acid;

rac-4-[(2R,4S)-4-({[1-(2,2-difluoro-1,3-benzodioxol-5-yl)cyclopropyl]carbonyl}amino)tetrahydro-2H-pyran-2-yl]benzoic acid;

3-[(2S,4R)-4-({[1-(2,2-difluoro-1,3-benzodioxol-5-yl)cyclopropyl]carbonyl}amino)tetrahydro-2H-pyran-2-yl]benzoic acid;

3-[(2R,4S)-4-({[1-(2,2-difluoro-1,3-benzodioxol-5-yl)cyclopropyl]carbonyl}amino)tetrahydro-2H-pyran-2-yl]benzoic acid;

rac-3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid;

3-[(2S,4R,6R)-4-({[1-(2,2-difluoro-1,3-benzodioxol-5-yl)cyclopropyl]carbonyl}amino)-6-phenyltetrahydro-2H-pyran-2-yl]benzoic acid;

3-[(2R,4S,6S)-4-({[1-(2,2-difluoro-1,3-benzodioxol-5-yl)cyclopropyl]carbonyl}amino)-6-phenyltetrahydro-2H-pyran-2-yl]benzoic acid;

4-[(2R,4S)-4-({[1-(2,2-difluoro-1,3-benzodioxol-5-yl)cyclopropyl]carbonyl}amino)tetrahydro-2H-pyran-2-yl]benzoic acid;

4-[6-(4-cyanopiperidin-1-yl)pyridin-3-yl]-3-cyclobutyl-N-(methanesulfonyl)-1-phenyl-1H-pyrazolo[3,4-b]pyridine-6-carboxamide;

3-cyclobutyl-N-(methanesulfonyl)-4-[4-(methoxymethyl)piperidin-1-yl]-1-phenyl-1H-pyrazolo[3,4-b]pyridine-6-carboxamide;

4-[6-(4-cyanopiperidin-1-yl)pyridin-3-yl]-3-cyclobutyl-N-(methanesulfonyl)-1-[2-(morpholin-4-yl)pyridin-4-yl]-1H-pyrazolo[3,4-b]pyridine-6-carboxamid;

N-(methanesulfonyl)-4-[4-(methoxymethyl)piperidin-1-yl]-1-[2-(morpholin-4-yl)pyridin-4-yl]-3-(propan-2-yl)-1H-pyrazolo[3,4-b]pyridine-6-carboxamide;

3-cyclobutyl-4-[4-(methoxymethyl)piperidin-1-yl]-N-[2-(morpholin-4-yl)ethanesulfonyl]-1-phenyl-1H-pyrazolo[3,4-b]pyridine-6-carboxamide;

3-cyclobutyl-N-[2-(dimethylamino)ethanesulfonyl]-4-[4-(methoxymethyl)piperidin-1-yl]-1-phenyl-1H-pyrazolo[3,4-b]pyridine-6-carboxamide;

1-(4-fluorophenyl)-N-(methanesulfonyl)-4-(1'-methyl[4,4'-bipiperidin]-1-yl)-3-(propan-2-yl)-1H-pyrazolo[3,4-b]pyridine-6-carboxamide;

3-cyclobutyl-N-(methanesulfonyl)-4-{4-[2-(morpholin-4-yl)ethyl]piperidin-1-yl}-1-phenyl-1H-pyrazolo[3,4-b]pyridine-6-carboxamide;

3-cyclobutyl-4-[4-(methoxymethyl)piperidin-1-yl]-N-(oxolane-3-sulfonyl)-1-phenyl-1H-pyrazolo[3,4-b]pyridine-6-carboxamide;

3-cyclobutyl-N-(dimethylsulfamoyl)-1-(4-fluorophenyl)-4-(4-methoxy[1,4'-bipiperidin]-1'-yl)-1H-pyrazolo[3,4-b]pyridine-6-carboxamide;

3-cyclobutyl-N-(morpholine-4-sulfonyl)-4-[4-(morpholin-4-yl)piperidin-1-yl]-1-phenyl-1H-pyrazolo[3,4-b]pyridine-6-carboxamide;

3-cyclobutyl-N-(morpholine-4-sulfonyl)-1-phenyl-4-{4-[(pyrrolidin-1-yl)methyl]piperidin-1-yl}-1H-pyrazolo[3,4-b]pyridine-6-carboxamide;

3-cyclobutyl-N-(methanesulfonyl)-4-[4-(morpholin-4-yl)piperidin-1-yl]-1-phenyl-1H-pyrazolo[3,4-b]pyridine-6-carboxamide;

3-cyclobutyl-4-[4-(morpholin-4-yl)piperidin-1-yl]-1-phenyl-1H-pyrazolo[3,4-b]pyridine-6-carboxylic acid;

3-cyclobutyl-1-phenyl-4-{4-[(pyrrolidin-1-yl)methyl]piperidin-1-yl}-1H-pyrazolo[3,4-b]pyridine-6-carboxylic acid;

5-[(2R,4R)-4-{[(7R)-2,2-difluoro-7-methyl-6,7-dihydro-2H-furo[2,3-f][1,3]benzodioxole-7-carbonyl]amino}-7-methoxy-3,4-dihydro-2H-1-benzopyran-2-yl]pyrazine-2-carboxylic acid;

6-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]pyridine-3-carboxylic acid;

trans-4-[(2S,4S)-4-{[(7R)-2,2-difluoro-7-methyl-6, 7-dihydro-2H-furo[2,3-f][1,3]benzodioxole-7-carbonyl]amino}-7-(trifluoromethoxy)-3,4-dihydro-2H-1-benzopyran-2-yl]cyclohexane-1-carboxylic acid;

6-[(2R,4R)-7-(difluoromethoxy)-4-{[(7R)-2,2-difluoro-7-methyl-6, 7-dihydro-2H-furo[2,3-f][1,3]benzodioxole-7-carbonyl]amino}-3,4-dihydro-2H-1-benzopyran-2-yl]pyridine-3-carboxylic acid;

trans-4-[(2S,4S)-4-{[(7R)-2,2-difluoro-7-methyl-6, 7-dihydro-2H-furo[2,3-f][1,3]benzodioxole-7-carbonyl]amino}-7-methoxy-3,4-dihydro-2H-1-benzopyran-2-yl]cyclohexane-1-carboxylic acid;

ethyl trans-4-[(2S,4S)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylate;

cis-4-[(2R,4R)-4-{[(7R)-2,2-difluoro-7-methyl-6, 7-dihydro-2H-furo[2,3 f][1,3]benzodioxole-7-carbonyl]amino}-7-(trifluoromethoxy)-3,4-dihydro-2H-1-benzopyran-2-yl]cyclohexane-1-carboxylic acid;

trans-4-[(2S,4S)-7-(difluoromethoxy)-4-{[(7R)-2,2-difluoro-7-methyl-6,7-dihydro-2H-furo[2,3-f][1,3]benzodioxole-7-carbonyl]amino}-3,4-dihydro-2H-1-benzopyran-2-yl]cyclohexane-1-carboxylic acid;

1-[(2R,4R)-4-{[(7R)-2,2-difluoro-7-methyl-6,7-dihydro-2H-furo[2,3-f][1,3]benzodioxole-7-carbonyl]amino}-7-(trifluoromethoxy)-3,4-dihydro-2H-1-benzopyran-2-yl]cyclopropane-1-carboxylic acid;

trans-4-[(2R,4R)-4-{[(5S)-2,2-difluoro-5-methyl-6,7-dihydro-2H, 5H-indeno[5,6-d][1,3]dioxole-5-carbonyl]amino}-7-(trifluoromethoxy)-3,4-dihydro-2H-1-benzopyran-2-yl]cyclohexane-1-carboxylic acid;

trans-4-[(2R,4R)-4-{[(5S)-2,2-difluoro-5-methyl-6,7-dihydro-2H, 5H-indeno[5,6-d][1,3]dioxole-5-carbonyl]amino}-7-methoxy-3,4-dihydro-2H-1-benzopyran-2-yl]cyclohexane-1-carboxylic acid;

trans-4-[(2R,4R)-4-{[(7R)-2,2-difluoro-7-methyl-6,7-dihydro-2H-furo[2,3-j][1,3]benzodioxole-7-carbonyl]amino}-7-methoxy-3,4-dihydro-2H-1-benzopyran-2-yl]cyclohexane-1-carboxylic acid;

trans-4-[(2R,4R)-7-(difluoromethoxy)-4-{[(7R)-2,2-difluoro-7-methyl-6,7-dihydro-2H-furo[2,3-j][1,3]benzodioxole-7-carbonyl]amino}-3,4-dihydro-2H-1-benzopyran-2-yl]cyclohexane-1-carboxylic acid;

trans-4-[(2R,4R)-4-{[(7R)-2,2-difluoro-7-methyl-6,7-dihydro-2H-furo[2,3-j][1,3]benzodioxole-7-carbonyl]amino}-7-(trifluoromethoxy)-3,4-dihydro-2H-1-benzopyran-2-yl]cyclohexane-1-carboxylic acid;

4-{(2R,4R)-4-[2-(2,2-difluoro-2H-1,3-benzodioxol-5-yl)-2-methylpropanamido]-7-methoxy-3,4-dihydro-2H-1-benzopyran-2-yl}benzoic acid;

4-[(2R,4R)-4-{[1-(3,4-dichlorophenyl)cyclopropane-1-carbonyl]amino}-7-methoxy-3,4-dihydro-2H-1-benzopyran-2-yl]benzoic acid;

4-[(2R,4R)-4-{[1-(4-bromophenyl)cyclopropane-1-carbonyl]amino}-7-methoxy-3,4-dihydro-2H-1-benzopyran-2-yl]benzoic acid;

4-[(2R,4R)-7-methoxy-4-({1-[4-(trifluoromethyl)phenyl]cyclopropane-1-carbonyl}amino)-3,4-dihydro-2H-1-benzopyran-2-yl]benzoic acid;

4-[(2R,4R)-7-methoxy-4-{1-(4-methylphenyl)cyclopropane-1-carbonyl]amino}-3,4-dihydro-2H-1-benzopyran-2-yl]benzoic acid;

4-{(2R,4R)-4-[(1,5-dimethyl-2,3-dihydro-1H-indene-1-carbonyl)amino]-7-methoxy-3,4-dihydro-2H-1-benzopyran-2-yl}benzoic acid;

3-[(2R,4R)-4-{[(1S)-1,5-dimethyl-2,3-dihydro-1H-indene-1-carbonyl]amino}-7-methoxy-3,4-dihydro-2H-1-benzopyran-2-yl]benzoic acid;

4-[(2R,4R)-4-{[(1S)-1,5-dimethyl-2,3-dihydro-1H-indene-1-carbonyl]amino}-7-methoxy-3,4-dihydro-2H-1-benzopyran-2-yl]benzoic acid;

trans-4-[(2R,4R)-4-{[1-(2,2-difluoro-2H-1,3-benzodioxol-5-yl)cyclopropane-1-carbonyl]amino}-7-methoxy-3,4-dihydro-2H-1-benzopyran-2-yl]cyclohexane-1-carboxylic acid;

trans-4-[(2R,4R)-4-{[1-(2,2-difluoro-2H-1,3-benzodioxol-5-yl)cyclopropane-1-carbonyl]amino}-7-(trifluoromethoxy)-3,4-dihydro-2H-1-benzopyran-2-yl]cyclohexane-1-carboxylic acid; and 4-[(2R,4R)-4-{[1-(2,2-difluoro-2H-1,3-benzodioxol-5-yl)cyclopropane-1-carbonyl]amino}-7-(difluoromethoxy)-3,4-dihydro-2H-1-benzopyran-2-yl]cyclohexane-1-carboxylic acid.

In one embodiment, the additional therapeutic agent is a CFTR amplifier. CFTR amplifiers enhance the effect of known CFTR modulators, such as potentiators and correctors. Examples of CFTR amplifiers include PTI130 and PTI-428. Examples of amplifiers are also disclosed in International Patent Publication Nos.: WO2015138909 and WO2015138934.

In one embodiment, the additional therapeutic agent is a CFTR stabilizer. CFTR stabilizers enhance the stability of corrected CFTR that has been treated with a corrector, corrector/potentiator or other CFTR modulator combination(s). An example of a CFTR stabilizer is cavosonstat (N91115). Examples of stabilizers are also disclosed in International Patent Publication No.: WO2012048181.

In one embodiment, the additional therapeutic agent is an agent that reduces the activity of the epithelial sodium channel blocker (ENaC) either directly by blocking the channel or indirectly by modulation of proteases that lead to an increase in ENaC activity (e.g., serine proteases, channel-activating proteases). Exemplary of such agents include camostat (a trypsin-like protease inhibitor), QAU145, 552-02, GS-9411, INO-4995, Aerolytic, amiloride, and VX-371. Additional agents that reduce the activity of the epithelial sodium channel blocker (ENaC) can be found, for example, in International Patent Publication Nos.: WO2009074575 and WO2013043720; and U.S. Pat. No. 8,999,976.

In one embodiment, the ENaC inhibitor is VX-371.

In one embodiment, the ENaC inhibitor is SPX-101 (S18).

This invention also is directed to kits that comprise one or more compounds and/or salts of the invention, and, optionally, one or more additional therapeutic agents.

This invention also is directed to methods of use of the compounds, salts, compositions, and/or kits of the invention to, for example, modulate the Cystic Fibrosis Transmembrane Conductance Regulator (CFTR) protein, and treat a disease treatable by modulating the Cystic Fibrosis Transmembrane Conductance Regulator (CFTR) protein (including cystic fibrosis, Sjögren's syndrome, pancreatic insufficiency, chronic obstructive lung disease, and chronic obstructive airway disease).

General Synthesis

The compounds of the present disclosure can be better understood in connection with the following synthetic schemes and methods which illustrate a means by which the compounds can be prepared.

The compounds of this disclosure can be prepared by a variety of synthetic procedures. Representative procedures are shown in, but are not limited to, Schemes 1-3. In Schemes 1-3, the variables $X^1$, $X^2$, $R^1$, and $R^3$ are is as described in the Summary, or they represent a moiety that can be converted to one of said groups using chemical transformations known to one of skill in the art.

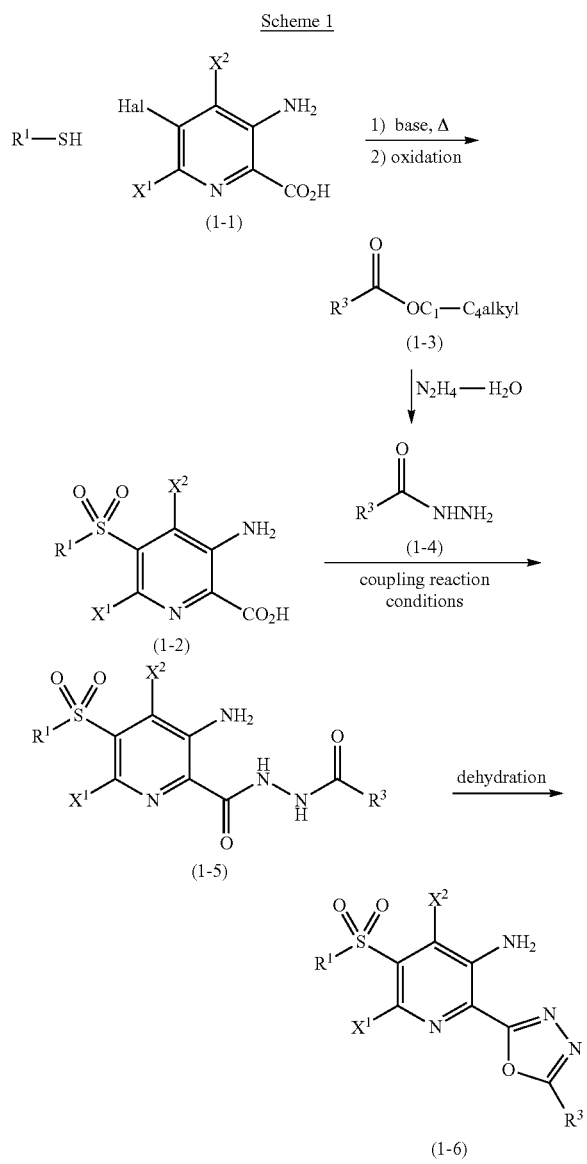

As shown in Scheme 1, compounds of formula (1-6) can be prepared from compounds of formula (1-1). Compounds of formula (1-1), wherein Hal is a halogen, can be reacted first with thiols ($R^1$—SH) in the presence of a base such as 1,8-diazabicyclo[5.4.0]undec-7-ene or potassium carbonate in a solvent such as but not limited to N,N-dimethylacetamide heated either conventionally or with microwave irradiation to give intermediate thioethers. The intermediate thioethers can be oxidized in a second step with hydrogen peroxide in a solvent such as cooled trifluoroacetic acid to give compounds of formula (1-2). Carboxylic acids of formula (1-2) can be coupled with acylhydrazines of formula (1-4) to give compounds of formula (1-5). Examples of conditions known to generate compounds of formula (1-5) from a mixture of a carboxylic acid and an acylhydrazine include, but are not limited to, adding a coupling reagent such as, but not limited to, N-(3-dimethylaminopropyl)-N'-ethylcarbodiimide or 1-(3-dimethylaminopropyl)-3-ethylcarbodiimide (EDC, EDAC or EDCI) or the corresponding hydrochloride salt, 1,3-dicyclohexylcarbodiimide (DCC), bis(2-oxo-3-oxazolidinyl)phosphinic chloride (BOPCl), N-[(dimethylamino)-1H-1,2,3-triazolo-[4,5-b]pyridin-1-yl-methylene]-N-methylmethanaminium hexafluorophosphate N-oxide or 2-(7-azabenzotriazol-1-yl)-N,N,N',N'-tetramethyluronium hexafluorophosphate or 1-[bis(dimethylamino)methylene]-1H-1,2,3-triazolo[4,5-b]pyridinium 3-oxid hexafluorophosphate (HATU), O-(benzotriazol-1-yl)-N,N,N',N'-tetramethyluronium tetrafluoroborate (TBTU), 2-(1H-benzo[d][1,2,3]triazol-1-yl)-1, 1,3,3-tetramethylisouronium hexafluorophosphate(V) (HBTU), and 2,4,6-tripropyl-1,3,5,2,4,6-trioxatriphosphinane 2,4,6-trioxide (T3P®). The coupling reagents may be added as a solid, a solution, or as the reagent bound to a solid support resin. In addition to the coupling reagents, auxiliary-coupling reagents may facilitate the coupling reaction. Auxiliary coupling reagents that are often used in the coupling reactions include but are not limited to 4-(dimethylamino) pyridine (DMAP), 1-hydroxy-7-azabenzotriazole (HOAT) and 1-hydroxybenzotriazole (HOBT). The reaction may be carried out optionally in the presence of a base such as, but not limited to, triethylamine, N,N-diisopropylethylamine or pyridine. The coupling reaction may be carried out in solvents such as, but not limited to, tetrahydrofuran, N,N-dimethylformamide, N,N-dimethylacetamide, dimethyl sulfoxide, dichloromethane, and ethyl acetate. The reactions may be carried out at ambient temperature or heated. The heating can be accomplished either conventionally or with microwave irradiation. Acylhydrazines of formula (1-4) are either commercially available or prepared from esters of formula (1-3). Esters of formula (1-3) can be treated with hydrazine hydrate in a solvent such as but not limited to heated tetrahydrofuran. Compounds of formula (1-5) can be dehydrated by treatment with p-toluenesulfonyl chloride and a base such as triethylamine in a solvent such as but not limited to dichloromethane to give compounds of formula (1-6). The $R^3$ substituent may be further manipulated under reaction conditions known to one of skill in the art to give $R^3$ substituents as described in the Summary. Compounds of formula (1-6) are representative of compounds of formula (I).

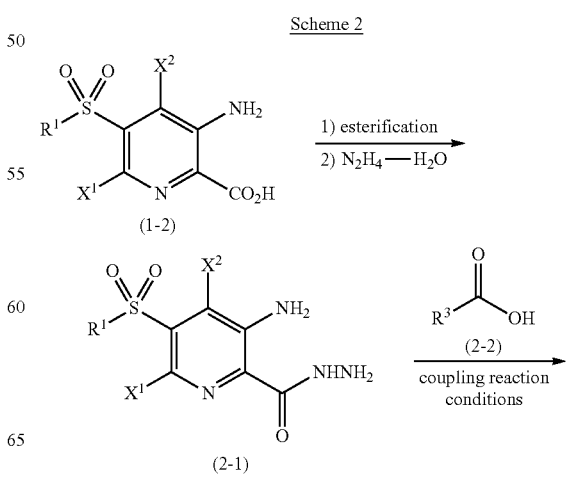

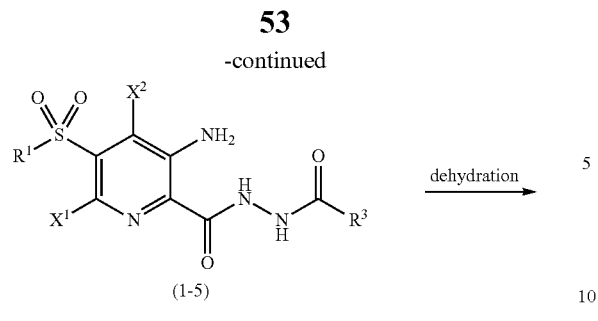

(1-5)

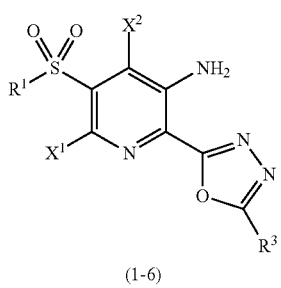

(1-6)

As shown in Scheme 2, compounds of formula (1-6) can be prepared from compounds of formula (1-2) in an alternative to the sequence shown in Scheme 1. Compounds of formula (1-2) can be converted to compounds of formula (2-1) in a two-step process. In the first step, compounds of formula (1-2) can be esterified by combining compounds of formula (1-2) with methanol or ethanol in the presence of an acid catalyst such as but not limited to sulfuric acid. Heating the mixture provides intermediate esters. Said intermediate esters can be treated in a second step with hydrazine hydrate in a heated solvent such as tetrahydrofuran to give compounds of formula (2-1). Compounds of formula (2-1) can be coupled to compounds of formula (2-2) using the conditions described in Scheme 1 to couple a carboxylic acid to an acylhydrazine to give compounds of formula (1-5). Compounds of formula (1-5) can be dehydrated as described in Scheme 1 to give compounds of formula (1-6). Compounds of formula (1-6) are representative of compounds of formula (I).

(3-2)

As shown in Scheme 3, compounds of formula (3-3) can be prepared from compounds of formula (1-2). Compounds of formula (1-2) can be converted to compounds of formula (3-1) in a two-step process. Compounds of formula (1-2) can also be coupled with ammonia using the coupling conditions described in Scheme 1 to couple a carboxylic acid and an acylhydrazine to give intermediate primary amides. Said primary amides can be reacted with phosphorus pentasulfide in the presence of an acid such as 1 M hydrochloric acid in a heated mixture of solvent such as but not limited to tetrahydrofuran and toluene to give thioamides of formula (3-1). Thioamides of formula (3-1) can be reacted with α-bromoaldehydes of formula (3-2) in the presence of a base such as but not limited to pyridine in a heated solvent such as but not limited to 2-methyltetrahydrofuran to give compounds of formula (3-3). Compounds of formula (3-3) are representative of compounds of formula (I).

Scheme 4

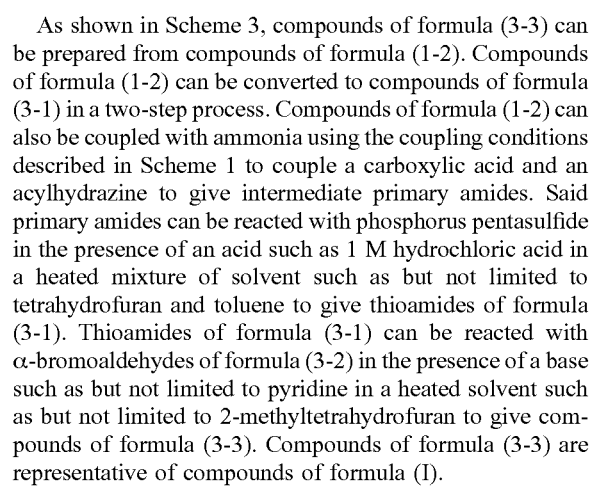

Scheme 3

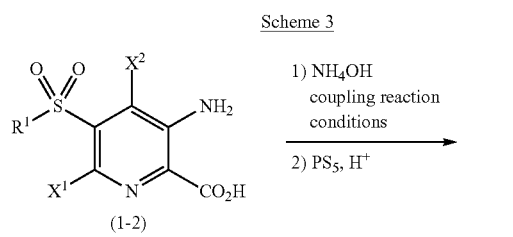

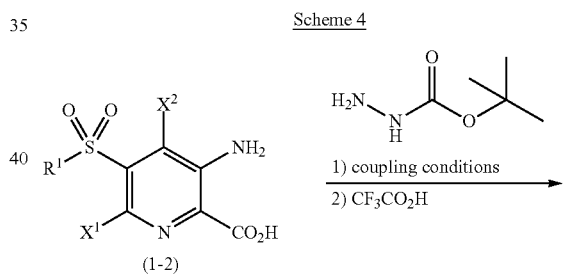

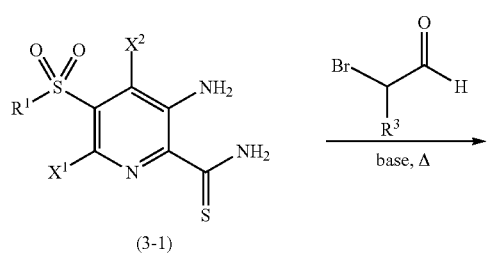

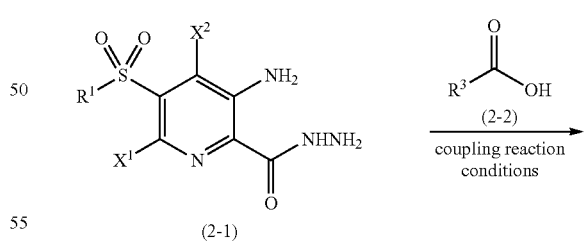

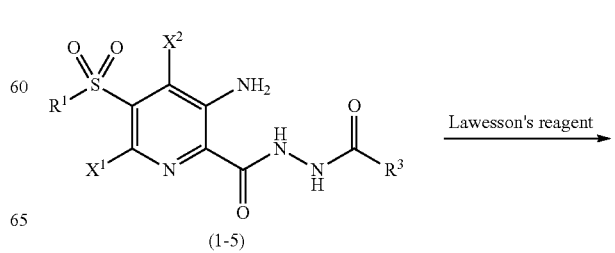

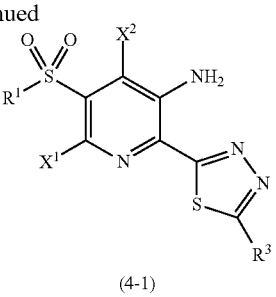

(4-1)

As shown in Scheme 4, compounds of formula (4-1) can be prepared from compounds of formula (1-2) in sequence similar to the one shown in Scheme 2. Compounds of formula (1-2) can be converted to compounds of formula (2-1) in a two-step process. In the first step, compounds of formula (1-2) are coupled to tert-butyl hydrazinecarboxylate using standard peptide coupling conditions known to those skilled in the art, and widely available in the literature. The Boc-protected substrate can be treated with an acid, such as but not limited to TFA (trifluoroacetic acid), to provide compounds of formula (2-1). Compounds of formula (2-1) can be coupled to compounds of formula (2-2) using the conditions described in Scheme 1 to couple a carboxylic acid to an acylhydrazine to give compounds of formula (1-5). Compounds of formula (1-5) can be treated with Lawesson's reagent to give compounds of formula (4-1). The reaction is typically performed at an elevated temperature in a solvent such as, but not limited to, toluene. Compounds of formula (4-1) are representative of compounds of formula (I).

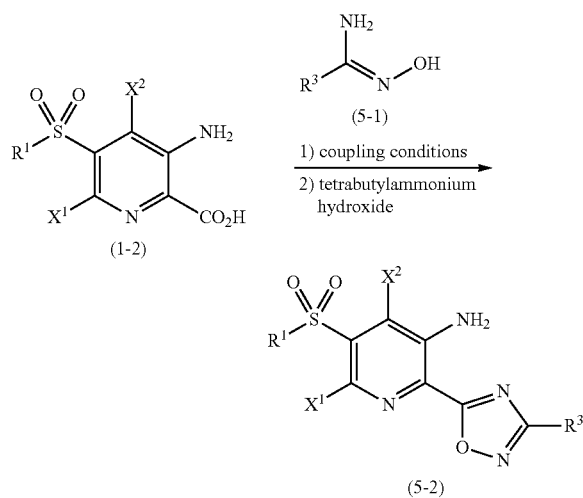

As shown in Scheme 5, compounds of formula (5-2) can be prepared from compounds of formula (1-2). Compounds of formula (1-2) can be reacted with compounds of formula (5-1), wherein $R^3$ is as described herein, using coupling conditions, such as in the presence of 2-(3H-[1,2,3]triazolo[4,5-b]pyridin-3-yl)-1, 1,3,3-tetramethylisouronium hexafluorophosphate(V) and N-ethyl-N-isopropylpropan-2-amine. The reaction is typically performed in a solvent, such as, but not limited to, N,N-dimethyl acetamide. The coupled intermediate can then be treated with tetrabutylammonium hydroxide to provide compounds of formula (5-2). The reaction is typically performed at ambient temperature in a solvent such as, but not limited to, tetrahydrofuran. Compounds of formula (5-2) are representative of compounds of formula (I).

Chemical Synthetic Procedures

List of abbreviations used in the examples section: min for minute; DBU for 1,8-diazabicyclo[5.4.0]undec-7-ene; DCI for desorption chemical ionization; DMSO for dimethyl sulfoxide; EDCI for 1-(3-dimethylaminopropyl)-3-ethylcarbodiimide hydrochloride; ESI for electrospray ionization; HATU for 1-[bis(dimethylamino)methylene]-1H-1,2,3-triazolo[4,5-b]pyridinium 3-oxid hexafluorophosphate; HPLC for high performance liquid chromatography; MS for mass spectrometry; NMR for nuclear magnetic resonance; wt for weight, and UPLC for ultra performance liquid chromatography.

The compounds of the invention can be prepared from readily available starting materials using the following general methods and procedures. It will be appreciated that where typical or preferred process conditions (i.e., reaction temperatures, times, mole ratios of reactants, solvents, pressures, etc.) were given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art (*Protective Groups in Organic Synthesis Third Edition*; Greene, T W and Wuts, P G M, Eds.; Wiley-Interscience: New York, 1991).

The following methods are presented with details as to the preparation of a compound of the invention as defined hereinabove and the comparative examples. A compound of the invention may be prepared from known or commercially available starting materials and reagents by one skilled in the art of organic synthesis.

All reagents were of commercial grade and were used as received without further purification, unless otherwise stated. Commercially available anhydrous solvents were used for reactions conducted under inert atmosphere. Reagent grade solvents were used in all other cases, unless otherwise specified. Column chromatography was performed on silica gel 60 (35-70 μm). Thin layer chromatography was carried out using pre-coated silica gel F-254 plates (thickness 0.25 mm). $^1$H NMR spectra were recorded on a Bruker Advance 300 NMR spectrometer (300 MHz), an Agilent 400 MHz NMR spectrometer, or a 500 MHz NMR. Chemical shifts (δ) for $^1$H NMR spectra were reported in parts per million (ppm) relative to tetramethylsilane (δ 0.00) or the appropriate residual solvent peak, i.e. CHCl$_3$ (δ 7.27), as internal reference. Multiplicities were given as singlet (s), doublet (d), doublet of quartets (dq), triplet (t), quartet (q), quintuplet (quin), multiplet (m) and broad (br). Electrospray MS spectra were obtained on a Waters platform LC/MS spectrometer or with Waters Acquity H-Class UPLC coupled to a Waters Mass detector 3100 spectrometer. Columns used: Waters Acquity UPLC BEH C18 1.7 μm, 2.1 mm ID×50 mm L, Waters Acquity UPLC BEH C18 1.7 μm, 2.1 mm ID×30 mm L, or Waters Xterra® MS 5 μm C18, 100×4.6 mm. The methods were using either CH$_3$CN/H$_2$O gradients (H$_2$O contains either 0.1% CF$_3$CO$_2$H or 0.1%

NH₃) or CH₃OH/H₂O gradients (H₂O contains 0.05% CF₃CO₂H). Microwave heating was performed with a Biotage® Initiator. Reverse Phase Purification Methods Trifluoroacetic Acid Method Samples were purified by preparative HPLC on a Phenomenex® Luna® C8(2) 5 μm 100 Å AXIA column (30 mm×75 mm). A gradient of acetonitrile (A) and 0.1% trifluoroacetic acid in water (B) was used, at a flow rate of 50 mL/min (0-1.0 min 5% A, 1.0-8.5 min linear gradient 5-100% A, 8.5-11.5 min 100% A, 11.5-12.0 min linear gradient 95-5% A).

Prep LC/MS Method TFA6

Samples were purified by reverse phase preparative HPLC on a Phenomenex® Luna® C8(2) 5 μm 100 Å AXIA column (50 mm×21.2 mm). A gradient of acetonitrile (A) and 0.1% trifluoroacetic acid in water (B) was used, at a flow rate of 40 mL/min (0-0.5 min 15% A, 0.5-8.0 min linear gradient 15-100% A, 8.0-9.0 min 100% A, 7.0-8.9 min 100% A, 9.0-9.1 min linear gradient 100-15% A, 9.1-10 min 15% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; and Thermo MSQ Plus mass spectrometer. The system was controlled through a combination of Thermo Xcalibur 2.0.7 software and a custom application written in-house using Microsoft Visual Basic 6.0.

Prep LC/MS Method TFA8

Samples were purified by reverse phase preparative HPLC on a Phenomenex® Luna® C8(2) 5 μm 100 Å AXIA column (50 mm×21.2 mm). A gradient of acetonitrile (A) and 0.1% trifluoroacetic acid in water (B) was used, at a flow rate of 40 mL/min (0-0.5 min 35% A, 0.5-8.0 min linear gradient 35-100% A, 8.0-9.0 min 100% A, 7.0-8.9 min 100% A, 9.0-9.1 min linear gradient 100-35% A, 9.1-10 min 35% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; and Thermo MSQ Plus mass spectrometer. The system was controlled through a combination of Thermo Xcalibur 2.0.7 software and a custom application written in-house using Microsoft Visual Basic 6.0.

Prep LC/MS Method TFA10

Samples were purified by reverse phase preparative HPLC on a Phenomenex® Luna® C8(2) 5 μm 100 Å AXIA column (50 mm×21.2 mm). A gradient of acetonitrile (A) and 0.1% trifluoroacetic acid in water (B) was used, at a flow rate of 30 mL/min (0-0.2 min 5% A, 0.2-3.0 min linear gradient 5-100% A, 4.1-4.5 min 100-5% A, 4.5-5.0 min 5% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; and Thermo MSQ Plus mass spectrometer. The system was controlled through a combination of Thermo Xcalibur 2.0.7 software and a custom application written in-house using Microsoft Visual Basic 6.0.

Prep LC/MS Method AA6

Samples were purified by reverse phase preparative HPLC on a Phenomenex® Luna® C8(2) 5 μm 100 Å AXIA column (50 mm×21.2 mm). A gradient of acetonitrile (A) and 0.1% ammonium acetate in water (B) was used, at a flow rate of 40 mL/min (0-0.5 min 15% A, 0.5-8.0 min linear gradient 15-100% A, 8.0-9.0 min 100% A, 7.0-8.9 min 100% A, 9.0-9.1 min linear gradient 100-15% A, 9.1-10 min 15% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; and Thermo MSQ Plus mass spectrometer. The system was controlled through a combination of Thermo Xcalibur 2.0.7 software and a custom application written in-house using Microsoft Visual Basic 6.0.

Prep LC/MS Method AA7

Samples were purified by reverse phase preparative HPLC on a Phenomenex® Luna® C8(2) 5 μm 100 Å AXIA column (50 mm×21.2 mm). A gradient of acetonitrile (A) and 0.1% ammonium acetate in water (B) was used, at a flow rate of 40 mL/min (0-0.5 min 25% A, 0.5-8.0 min linear gradient 25-100% A, 8.0-9.0 min 100% A, 7.0-8.9 min 100% A, 9.0-9.1 min linear gradient 100-25% A, 9.1-10 min 25% A). A custom purification system was used, consisting of the following modules: Gilson 305 and 306 pumps; Gilson 806 Manometric module; Gilson UV/Vis 155 detector; Gilson 506C interface box; Gilson FC204 fraction collector; Agilent G1968D Active Splitter; and Thermo MSQ Plus mass spectrometer. The system was controlled through a combination of Thermo Xcalibur 2.0.7 software and a custom application written in-house using Microsoft Visual Basic 6.0.

EXAMPLE 1

(5-{3-amino-5-[4-(trifluoromethoxy)benzene-1-sulfonyl]pyridin-2-yl}-1,3,4-oxadiazol-2-yl)methanol Step 1: 3-Amino-5-(4-trifluoromethoxy-phenylsulfanyl)-pyridine-2-carboxylic acid A solution of 3-amino-5-bromo-pyridine-2-carboxylic acid (CAS: 870997-85-6, 3.26 g, 15 mmol), 4-(trifluoromethoxy)benzene-1-thiol (CAS: 169685-29-4, 3.5 g, 18 mmol) and 1,8-diazabicyclo[5.4.0]undec-7-ene (DBU, 2.22 mL, 15 mmol) was prepared in N,N-dimethylacetamide (15 mL). This mixture was heated at 140° C. for 45 minutes in a microwave reactor. Next, the mixture was diluted with a mixture of 1% acetic acid in water. A suspension was obtained that was subsequently filtered. This collected solid was washed with a 1% acetic acid/water mixture followed by washing with petroleum ether. After drying in a vacuum oven, the titled compound was obtained. ¹H NMR (400 MHz, DMSO-d₆) δ ppm 7.68 (d, J=2.0 Hz, 1H), 7.64-7.60 (m, 2H), 7.48-7.44 (m, 2H), 6.99 (d, J=2.0 Hz, 1H).

Step 2: 3-Amino-5-(4-trifluoromethoxy-benzenesulfonyl)-pyridine-2-carboxylic acid 3-Amino-5-(4-trifluoromethoxy-phenylsulfanyl)-pyridine-2-carboxylic acid (12.5 g, 40 mmol, Step 1) was dissolved in trifluoroacetic acid (80 mL), and the resulting mixture was cooled to 0° C. with an ice bath. Next, $H_2O_2$ (14 mL, 160 mmol) was added, and the mixture was stirred at 0° C. until the reaction was finished. For workup, the mixture was diluted with a mixture of 1% acetic acid in water. A suspension was obtained that was subsequently filtered. The collected solid was washed with a 1% acetic acid/water mixture followed by washing with petroleum ether. After drying in a vacuum oven, the titled compound was obtained. MS (ESI+) m/z 363 [M+H]+; $^1$H NMR (400 MHz, DMSO-$d_6$) δ ppm 8.26 (d, J=1.9 Hz, 1H), 8.14 (d, J=8.8 Hz, 2H), 7.79 (d, J=1.9 Hz, 1H), 7.65 (d, J=8.4 Hz, 2H).

Step 3: 3-amino-N'-(hydroxyacetyl)-5-[4-(trifluoromethoxy)benzene-1-sulfonyl]pyridine-2-carbohydrazide To a 40 mL vial was added 3-amino-5-(4-trifluoromethoxy-benzenesulfonyl)-pyridine-2-carboxylic acid (0.50 g, 1.311 mmol, Step 2) and N,N-dimethylformamide (3 mL). 1-[Bis(dimethylamino)methylene]-1H-1,2,3-triazolo[4,5-b]pyridinium 3-oxid hexafluorophosphate (HATU, 0.548 g, 1.442 mmol) was then added, and the resulting solution was stirred for 30 minutes at room temperature. This solution was then transferred via cannula into another 20 mL vial which contained 2-hydroxyacetohydrazide (0.154 g, 1.704 mmol) in N,N-dimethylformamide (3 mL). N,N-Dimethylformamide (1 mL) was added as a rinse. Hunig's base (0.458 mL, 2.62 mmol) was then added dropwise, and the mixture was stirred for 30 minutes at room temperature. Ethyl acetate (20 mL) and 5% $NaHCO_3$ (20 mL) were added, the resulting biphasic mixture was stirred for 5 minute, and the layers were separated. The aqueous layer was extracted with ethyl acetate (20 mL). The combined organic extracts were washed with water (2×20 mL) and brine (20 mL), dried over $Na_2SO_4$, filtered, and then concentrated in vacuo to give the titled compound, which was used without additional purification (470 mg). $^1$H NMR (501 MHz, DMSO-$d_6$) δ ppm 3.93 (d, J=5.9 Hz, 2H), 5.48 (t, J=6.0 Hz, 1H), 7.12-7.24 (m, 2H), 7.64 (dq, J=7.8, 1.1 Hz, 2H), 7.75 (d, J=2.0 Hz, 1H), 8.09-8.16 (m, 2H), 8.21 (d, J=2.1 Hz, 1H), 9.70 (s, 1H), 10.23 (s, 1H); MS (ESI−) m/z 433.1 [M−H]−.

Step 4: 3-amino-5-[4-(trifluoromethoxy)benzene-1-sulfonyl]-N'-({[tri(propan-2-yl)silyl]oxy}acetyl)pyridine-2-carbohydrazide 3-Amino-N'-(hydroxyacetyl)-5-[4-(trifluoromethoxy)benzene-1-sulfonyl]pyridine-2-carbohydrazide (0.5315 g, 1.224 mmol, Step 3) was suspended in 10 mL of dichloromethane in a 50-mL round-bottomed flask, and the flask was cooled to 0° C. in an ice bath. Triethylamine (0.341 mL, 2.447 mmol) was added, followed by dropwise addition of triisopropylsilyl trifluoromethanesulfonate (0.660 mL, 2.447 mmol). The reaction mixture was stirred at 0° C. for 15 minutes, at which point the flask was warmed to room temperature and stirred for an additional 2.5 hours. The reaction mixture was quenched by the addition of water. The organic layer was separated, dried over anhydrous sodium sulfate, filtered, and concentrated in vacuo. The residue was purified via flash chromatography, eluted with a gradient of 0-2.5% $CH_3OH$ in $CH_2Cl_2$ on a 40 g silica gel column to afford 720 mg of the titled compound. $^1$H NMR (400 MHz, DMSO-$d_6$) δ ppm 1.01 (d, J=7.1 Hz, 18H), 1.08-1.19 (m, 3H), 5.03 (s, 2H), 7.26 (s, 2H), 7.60-7.68 (m, 2H), 7.90 (d, J=2.0 Hz, 1H), 8.11-8.20 (m, 2H), 8.41 (d, J=2.0 Hz, 1H); MS (ESI+) m/z 591.1 [M+H]+.

Step 5: 5-[4-(trifluoromethoxy)benzene-1-sulfonyl]-2-[5-({[tri(propan-2-yl)silyl]oxy}methyl)-1,3,4-oxadiazol-2-yl]pyridin-3-amine To a solution of 3-amino-5-[4-(trifluoromethoxy)benzene-1-sulfonyl]-N'-({[tri(propan-2-yl)silyl]oxy}acetyl)pyridine-2-carbohydrazide (0.4638 g, 0.785 mmol, Step 4) and triethylamine (0.219 mL, 1.570 mmol) in dichloromethane (1.8 mL) was added p-toluenesulfonyl chloride (0.299 g, 1.570 mmol), and the reaction mixture was stirred at room temperature for 3 days. The reaction mixture was then washed with a saturated aqueous solution of $NaHCO_3$. The organic layer was separated, dried over anhydrous sodium sulfate, filtered, and concentrated in vacuo. The residue was purified via precipitation from 3 mL of dimethyl sulfoxide and 3 mL of methanol to give 268 mg of the titled compound. $^1$H NMR (400 MHz, DMSO-$d_6$) δ ppm 1.01 (d, J=7.1 Hz, 18H), 1.08-1.19 (m, 3H), 5.03 (s, 2H), 7.26 (s, 2H), 7.60-7.68 (m, 2H), 7.90 (d, J=2.0 Hz, 1H), 8.11-8.20 (m, 2H), 8.41 (d, J=2.0 Hz, 1H); MS (ESI+) m/z 573.1 [M+H]+.

Step 6: (5-{3-amino-5-[4-(trifluoromethoxy)benzene-1-sulfonyl]pyridin-2-yl}-1,3,4-oxadiazol-2-yl)methanol To a solution of 5-[4-(trifluoromethoxy)benzene-1-sulfonyl]-2-[5-({[tri(propan-2-yl)silyl]oxy}methyl)-1,3,4-oxadiazol-2-yl]pyridin-3-amine (0.2664 g, 0.465 mmol, Step 5) in tetrahydrofuran (3 mL) was added a solution of tetrabutylammonium fluoride in (1 M in tetrahydrofuran, 0.465 mL, 0.465 mmol) dropwise, and the reaction was stirred at room temperature for 1.5 hours. The reaction mixture was then partitioned between ethyl acetate and water. The combined organic extracts were dried over sodium sulfate, filtered, and concentrated in vacuo. The residue was then sonicated in dichloromethane to give a white solid, which was isolated via filtration and dried to constant weight to give 168 mg of the titled compound. $^1$H NMR (400 MHz, DMSO-$d_6$) δ ppm 4.71 (s, 2H), 5.98 (s, 1H), 7.23 (s, 2H), 7.63 (dq, J=8.9, 1.1 Hz, 2H), 7.87 (d, J=2.0 Hz, 1H), 8.07-8.20 (m, 2H), 8.39 (d, J=2.0 Hz, 1H); MS (ESI−) m/z 414.9 [M−H]−.

Alternative Preparation of 3-amino-5-[4-(trifluoromethoxy)benzene-1-sulfonyl]-N'-({[tri(propan-2-yl)silyl]oxy}acetyl)pyridine-2-carbohydrazide Step 1: methyl {[tri(propan-2-yl)silyl]oxy}acetate Methyl 2-hydroxyacetate (CAS: 96-35-5, 80 g, 888.9 mmol) was mixed with imidazole (CAS: 288-32-4, 182 g, 2.7 mol) in dry N,N-dimethylformamide (1 L). To this solution, triisopropylsilyl chloride (CAS:13154-24-0, 228 mL, 1.1 mol) was added. The resulting mixture was stirred at ambient temperature under a nitrogen atmosphere. After overnight stirring, the mixture was quenched with saturated $NaHCO_3$ (1.5 L) and subsequently extracted with diethyl ether. The combined organic fractions were washed with 2 M HCl (1.4 L, 2.8 mol), water (0.5 L) and brine (1 L). The organic layer was then dried over $Na_2SO_4$, filtered and concentrated to dryness to afford 199 g of title compound that was used as such.

Step 2: 2-{[tri(propan-2-yl)silyl]oxy}acetohydrazide

Methyl {[tri(propan-2-yl)silyl]oxy}acetate (199 g, 808.4 mmol) was dissolved in tetrahydrofuran (1 L). Aqueous hydrazine solution (35% w/w, 200 mL, 2.2 mol) was added, and the mixture was refluxed overnight. Next, the mixture was quenched with NaHCO$_3$ (1.5 L) followed by extraction with ether (4×500 mL). The combined organic fractions were dried over Na$_2$SO$_4$, filtered and concentrated to dryness to afford 191 g of crude material. The crude material was precipitated overnight from ethyl acetate/heptane (500 mL, 5/95) to afford 122 g of title compound.

Step 3: 3-amino-5-[4-(trifluoromethoxy)benzene-1-sulfonyl]-N'-({[tri(propan-2-yl)silyl]oxy}acetyl) pyridine-2-carbohydrazide 3-Amino-5-(4-trifluoromethoxy-benzenesulfonyl)-pyridine-2-carboxylic acid (107.3 g, 296.4 mmol) was mixed with 2-{[tri(propan-2-yl)silyl]oxy}acetohydrazide (87.5 g, 355.7 mmol), 1-(3-dimethylaminopropyl)-3-ethylcarbodiimide hydrochloride (EDCI, CAS: 1892-57-5, 68.3 g, 355.7 mmol) and 4-dimethylaminopyridine (CAS: 1122-58-3, 43.4 g, 355.7 mmol) in dichloromethane (2 L). The resulting mixture was stirred at ambient temperature overnight. Next, the reaction was quenched with 1 N HCl solution (1 L, 1 mol) and extracted with dichloromethane. The organic layer was washed with brine and H$_2$O, dried over Na$_2$SO$_4$, filtered and concentrated to dryness to afford 186.5 g of title compound which was used as such.

EXAMPLE 2

(5-{3-amino-5-[4-(trifluoromethoxy)benzene-1-sulfonyl]pyridin-2-yl}-1,3,4-oxadiazol-2-yl)methyl dihydrogen phosphate Step 1: (5-{3-amino-5-[4-(trifluoromethoxy)benzene-1-sulfonyl]pyridin-2-yl}-1,3,4-oxadiazol-2-yl) methyl di-tert-butyl phosphate 1H-Tetrazole (0.45 M in CH$_3$CN, 42.7 mL, 19.22 mmol) was diluted with N,N-dimethylacetamide (19.22 mL), and the CH$_3$CN was removed in vacuo at a bath temperature of 60° C. After cooling the flask to room temperature, (5-{3-amino-5-[4-(trifluoromethoxy)benzene-1-sulfonyl]pyridin-2-yl}-1,3,4-oxadiazol-2-yl)methanol (4 g, 9.61 mmol, Example 1) was added in one portion as a neat solid, followed by dropwise addition of di-tert-butyl N,N-diethylphosphoramidite (4.01 mL, 14.41 mmol). The reaction mixture was stirred for 1 hour at room temperature, at which point the reaction vessel was placed in a room temperature water bath, and dropwise addition of hydrogen peroxide (30% aqueous, 2.94 mL, 96 mmol) was performed. A delayed exotherm to a temperature of 40° C. was noted. After the flask had cooled to room temperature, the reaction mixture was stirred for 15 minutes, and the product began to precipitate out of solution. The reaction mixture was diluted with ethyl acetate, washed with water and brine, then dried over sodium sulfate, filtered, and concentrated in vacuo. The solid residue was precipitated from ethyl acetate/heptanes to give 5.255 g of the titled compound. $^1$H NMR (400 MHz, CDCl$_3$) δ ppm 8.49 (d, J=1.9 Hz, 1H), 8.05 (d, J=8.8 Hz, 2H), 7.75 (d, J=2.0 Hz, 1H), 7.45-7.33 (m, 2H), 6.39 (s, 2H), 5.27 (d, J=8.8 Hz, 2H), 1.53 (s, 18H); MS (ESI−) m/z 607.0 [M−H]$^−$.

Step 2: (5-{3-amino-5-[4-(trifluoromethoxy)benzene-1-sulfonyl]pyridin-2-yl}-1,3,4-oxadiazol-2-yl) methyl dihydrogen phosphate (5-{3-Amino-5-[4-(trifluoromethoxy)benzene-1-sulfonyl]pyridin-2-yl}-1,3,4-oxadiazol-2-yl)methyl di-tert-butyl phosphate (5.0 g, 8.22 mmol, Step 1) was dissolved in acetic acid (20.0 mL). HCl (1 M in acetic acid, 41.1 mL, 41.1 mmol) was added via syringe, and the resulting solution was stirred vigorously at room temperature. After approximately 1 minute, a solid began to precipitate out of solution. The resulting suspension was stirred for 30 minutes at room temperature, at which point the solids were collected with a fritted funnel. The filter cake was washed with 5 mL of acetic acid and 2×10 mL of heptanes, and then dried to constant weight in a vacuum oven for 16 hours at 35° C. to give the titled compound as a solid (3.7 g). $^1$H NMR (400 MHz, methanol-d$_4$) δ ppm 8.37 (d, J=2.0 Hz, 1H), 8.14 (d, J=8.9 Hz, 2H), 7.88 (d, J=2.0 Hz, 1H), 7.58-7.49 (m, 2H), 5.28 (d, J=9.1 Hz, 2H); MS (ESI−) m/z 495.0 [M−H]$^+$.

EXAMPLE 3

2-(5-{3-amino-5-[4-(trifluoromethoxy)benzene-1-sulfonyl]pyridin-2-yl}-1,3,4-oxadiazol-2-yl)-1,1,1-trifluoropropan-2-ol Step 1: methyl 3-amino-5-[4-(trifluoromethoxy) phenyl]sulfonyl-pyridine-2-carboxylate To a suspension of 3-amino-5-(4-trifluoromethoxy-benzenesulfonyl)-pyridine-2-carboxylic acid (1.08 g, 3 mmol, Example 1-Step 2) in CH$_3$OH (20 mL), a few drops of H$_2$SO$_4$ were added. The resulting mixture was stirred at 70° C. in a sealed vial for 72 hours. Next, the mixture was added to water, which was brought to pH=7 using a 1 M NaOH solution. The resulting precipitate was collected by filtration. The solid was washed with water and dried in the vacuum oven (50° C.) to give the titled compound (0.93 g) that was used without additional purification. MS (ESI+) m/z 377 [M+H]$^+$.

Step 2: 3-amino-5-[4-(trifluoromethoxy)phenyl] sulfonyl-pyridine-2-carbohydrazide Hydrazine hydrate (CAS: 7803-57-8, 80% in water, 4 mL) was added to a solution of methyl 3-amino-5-[4-(trifluoromethoxy)phenyl]sulfonyl-pyridine-2-carboxylate (0.92 g, 2.44 mmol, Step 1) in tetrahydrofuran (15 mL). The solution was heated at 55° C. in a sealed vial. After overnight stirring, the mixture was diluted in water, and the resulting suspension was filtered to give a solid that was washed with water. Subsequent drying in a vacuum oven (50° C.) gave the titled compound (0.7 g) that was used without additional purification. MS (ESI+) m/z 377 [M+H]$^+$.

Step 3: 3-amino-N'-(3,3,3-trifluoro-2-hydroxy-2-methylpropanoyl)-5-[4-(trifluoromethoxy)benzene-1-sulfonyl]pyridine-2-carbohydrazide To a 1-methyl-2-pyrrolidinone solution (4 mL) containing 3-amino-5-[4-(trifluoromethoxy)phenyl]sulfonyl-pyridine-2-carbohydrazide (188 mg, 0.5 mmol, 1 eq, Step 2), 1-[bis(dimethylamino)methylene]-1H-1,2,3-triazolo[4,5-b]pyridinium 3-oxid hexafluorophosphate (190 mg, 0.5 mmol, HATU, 1 eq) and triethylamine (139 μL, 1 mmol, 2 eq), 3,3,3-trifluoro-2-hydroxy-2-methylpropanoic acid (72 mg, 0.5 mmol, [CAS #114715-77-4], 1 eq) was added. The resulting mixture was stirred at room temperature until the reaction was finished. The titled compound was obtained after extraction with ethyl acetate and concentration of the combined organic fractions. MS (ESI+) m/z 517 [M+H]$^+$.

Step 4: 3-amino-5-[4-(trifluoromethoxy)benzene-1-sulfonyl]-N'-(3,3,3-tri fluoro-2-methyl-2-{[tri(propan-2-yl)silyl]oxy}propanoyl)pyridine-2-carbohydrazide To a suspension of 3-amino-N'-(3,3,3-trifluoro-2-hydroxy-2-methylpropanoyl)-5-[4-(trifluoromethoxy)benzene-1-sulfonyl]pyridine-2-carbohydrazide (258 mg, 0.5 mmol, 1 eq, Step 3) and triethylamine (28 µL, 1 mmol, 2 eq) in dichloromethane (15 mL) at 0° C., triisopropylsilyl trifluoromethanesulfonate (108 µL, 1 mmol CAS: 80522-42-5, 2 eq) was added dropwise. The resulting mixture was stirred at 0° C. for 15 minutes, after which it was allowed to reach room temperature. After complete reaction, the mixture was added to water and extracted with ethyl acetate. The combined organic fractions were dried with $Na_2SO_4$ and concentrated to give the titled compound that was used without additional purification. MS (ESI+) m/z 629 $[M-C_3H_7]^+$.

Step 5: 5-[4-(trifluoromethoxy)benzene-1-sulfonyl]-2-[5-(1,1,1-trifluoro-2-{[tri(propan-2-yl)silyl]oxy}propan-2-yl)-1,3,4-oxadiazol-2-yl]pyridin-3-amine To a solution of 3-amino-5-[4-(trifluoromethoxy)benzene-1-sulfonyl]-Y-(3,3,3-trifluoro-2-methyl-2-{[tri(propan-2-yl)silyl]oxy}propanoyl)pyridine-2-carbohydrazide (336 mg, 0.5 mmol, 1 eq, Step 4) and triethylamine (209 µL, 1.5 mmol, 3 eq) in dry dichloromethane (10 mL) was added p-toluenesulfonyl chloride (286 mg, 1.5 mmol, CAS: 98-59-9, 3 eq). The mixture was stirred at ambient temperature till completion. Next, the mixture was diluted with water and extracted with ethyl acetate. The combined organic fraction were washed with aqueous $NaHCO_3$, dried with $Na_2SO_4$, and concentrated. The residue was purified by column chromatography using petroleum ether/ethyl acetate (9/1) as eluent to give the titled compound. MS (ESI+) m/z 655 $[M+H]^+$.

Step 6: 2-(5-{3-amino-5-[4-(trifluoromethoxy)benzene-1-sulfonyl]pyridin-2-yl}-1,3,4-oxadiazol-2-yl)-1,1,1-trifluoropropan-2-ol To a tetrahydrofuran (5 mL) solution of 5-[4-(trifluoromethoxy)benzene-1-sulfonyl]-2-[5-(1,1,1-trifluoro-2-{[tri(propan-2-yl)silyl]oxy}propan-2-yl)-1,3,4-oxadiazol-2-yl]pyridin-3-amine (98 mg, 0.15 mmol, 1 eq, Step 5), a 1 M tetrabutylammonium fluoride solution in tetrahydrofuran (0.15 mL, 0.15 mmol, 1 eq) was added. The mixture was stirred at ambient temperature till completion. Next, the mixture was diluted with water and extracted with ethyl acetate. The combined organic fractions were dried and concentrated. The residue was purified by preparative chromatography (XSelect™ CSH Prep Guard Column, C18 19×10 mm 5 µm (Waters) with an XSelect™ CSH Prep OBD Column, C18 19×100 mm 5 µm (Waters) and a gradient of 0.1% formic acid in water (A) and acetonitrile (B) at a flow rate of 20 mL/minute is used. Alternatively, an XBridge™ Prep Guard Column, C18 19×10 mm 5 µm (Waters) with a XBridge™ Prep OBD Column, C18 19×100 mm 5 µm (Waters) and a gradient of 0.5% $NH_3$ in water (A) and acetonitrile (B) at a flow rate of 20 mL/minute). After elution, the solvent was removed under vacuum to give the titled compound. MS (ESI+) m/z 499 $[M+H]^+$; $^1H$ NMR (400 MHz, DMSO-$d_6$) δ ppm 8.46 (d, J=2 Hz, 1H), 8.16 (m, 2H), 7.93 (d, J=2 Hz, 1H), 7.67 (m, 1H), 7.67 (m, 2H), 7.27 (br. s, 2H), 1.84 (s, 3H).

EXAMPLE 4

1-(5-{3-amino-5-[4-(trifluoromethoxy)benzene-1-sulfonyl]pyridin-2-yl}-1,3,4-oxadiazol-2-yl)-2,2,2-trifluoroethan-1-ol The titled compound was prepared using the procedures described in the synthesis of Example 3 and substituting 3,3,3-trifluoro-2-hydroxypropanoic acid for 3,3,3-trifluoro-2-hydroxy-2-methylpropanoic acid in Step 3 and giving the following sequence of intermediates: 3-amino-N'-(3,3,3-trifluoro-2-hydroxypropanoyl)-5-[4-(trifluoromethoxy)benzene-1-sulfonyl]pyridine-2-carbohydrazide (MS (ESI+) m/z 503 $[M+H]^+$), 3-amino-5-[4-(trifluoromethoxy)benzene-1-sulfonyl]-N'-(3,3,3-trifluoro-2-{[tri(propan-2-yl)silyl]oxy}propanoyl)pyridine-2-carbohydrazide (MS (ESI+) m/z 615 $[M-C_3H_7]^+$, 643 $[M-CH_3]^+$), 5-[4-(trifluoromethoxy)benzene-1-sulfonyl]-2-[5-(2,2,2-trifluoro-1-{[tri(propan-2-yl)silyl]oxy}ethyl)-1,3,4-oxadiazol-2-yl]pyridin-3-amine (MS (ESI+) m/z 641 $[M+H]^+$). MS (ESI+) m/z 485 $[M+H]^+$; $^1H$ NMR (400 MHz, DMSO-$d_6$) δ ppm 8.43 (d, J=2 Hz, 1H), 8.15 (m, 2H), 7.90 (d, J=2 Hz, 1H), 7.67 (m, 2H), 7.29 (br s, 2H), 6.04 (t, J=6 Hz, 1H), 4.74 (d, J=6 Hz, 2H).

EXAMPLE 5

(2-{3-amino-5-[4-(trifluoromethoxy)benzene-1-sulfonyl]pyridin-2-yl}-1,3-thiazol-5-yl)methanol

Step 1: 3-amino-5-[4-(trifluoromethoxy)benzene-1-sulfonyl]pyridine-2-carboxamide A solution of 3-amino-5-(4-trifluoromethoxy-benzenesulfonyl)-pyridine-2-carboxylic acid (140 mg, 0.386 mmol, Example 1-Step 2) and 1-[bis(dimethylamino)methylene]-1H-1,2,3-triazolo[4,5-b]pyridinium 3-oxid hexafluorophosphate (294 mg, 0.773 mmol, HATU) in N,N-dimethylformamide (1.4 mL) was treated with triethylamine (108 µL, 0.773 mmol), stirred at room temperature for 20 minutes, treated with an excess of 37% aqueous ammonium hydroxide solution (407 µL, 3.86 mmol), and stirred overnight. The mixture was diluted with water (20 mL) and stirred for 15 minutes. The solid that formed was collected by filtration, washed with water and dried under vacuum to provide the titled compound (129 mg, 0.357 mmol, 92% yield). MS (DCI+) m/z 362 $[M+H]^+$, 379 $[M+NH_4]^+$; $^1H$ NMR (400 MHz, DMSO-$d_6$) δ ppm 8.17 (d, J=2.1 Hz, 1H), 8.13-8.09 (m, 2H), 8.02 (br s, 1H), 7.69 (d, J=2.1 Hz, 1H), 7.63 (d, J=8.1 Hz, 2H), 7.58 (br s, 1H), 7.25 (bs, 2H).

Step 2: 3-amino-5-[4-(trifluoromethoxy)benzene-1-sulfonyl]pyridine-2-carbothioamide A mixture 3-amino-5-[4-(trifluoromethoxy)benzene-1-sulfonyl]pyridine-2-carboxamide (80 mg, 0.221 mmol, Step 1) and phosphorus pentasulfide (49.2 mg, 0.221 mmol) in tetrahydrofuran (2 mL) was stirred at 55° C. for 45 minutes. The mixture was the treated with 1 M HCl (~10 mL) and toluene (20 mL). The mixture was stirred vigorously and heated to 95° C. for 2 hours, and then cooled to room temperature. The mixture was extracted with ethyl acetate. The ethyl acetate layer was washed with brine, dried (MgSO$_4$), filtered, concentrated, redissolved in ethyl acetate/$CH_2Cl_2$, treated with silica gel (~3 g) and concentrated to dryness. The silica gel suspension was transferred to a DASi™-12 cartridge atop a pre-equilibrated 25 g silica gel column. Chromatography via elution with a gradient of 20% to 50% ethyl acetate in heptanes provided the titled compound (36 mg, 0.095 mmol, 43.1% yield). $^1$H NMR (400 MHz, DMSO-$d_6$) δ ppm 9.93 (br s, 1H), 9.73 (br s, 1H), 8.20 (d, J=2.1 Hz, 1H), 8.16-8.11 (m, 2H), 7.81 (d, J=2.1 Hz, 1H), 7.71 (br s, 2H), 7.66 (d, J=8.1 Hz, 2H).

Step 3: 2-{3-amino-5-[4-(trifluoromethoxy)benzene-1-sulfonyl]pyridin-2-yl}-1,3-thiazole-5-carbaldehyde A mixture of 3-amino-5-[4-(trifluoromethoxy)benzene-1-sulfonyl]pyridine-2-carbothioamide (30 mg, 0.079 mmol, Step 2) and 2-bromomalonaldehyde (48.0 mg, 0.318 mmol) in 2-methyltetrahydrofuran was treated with pyridine (12.86 μL, 0.159 mmol), and the mixture was heated to 70° C. for 90 minutes. The mixture was cooled and partitioned between ethyl acetate (50 mL) and 0.1 M aqueous HCl (15 mL). The ethyl acetate layer was washed with brine, dried (MgSO$_4$), filtered, concentrated, redissolved in CH$_2$Cl$_2$/ethyl acetate, treated with silica gel (~1.5 g) and concentrated to dryness. The silica gel suspension was transferred to a DASi™-12 cartridge atop a pre-equilibrated 12 g silica gel column. Elution with a gradient of 15% to 50% ethyl acetate in heptanes provided the titled compound (7 mg, 0.016 mmol, 20.51% yield). MS (ESI+) m/z 462 (M+CH$_3$OH+H)$^+$; MS (ESI−) m/z 428 [M−H]$^−$; $^1$H NMR (400 MHz, CDCl$_3$) δ ppm 10.07 (s, 1H), 8.44 (s, 1H), 8.40 (d, J=1.9 Hz, 1H), 8.06-8.01 (m, 2H), 7.62 (d, J=1.9 Hz, 1H), 7.37 (d, J=8.1 Hz, 2H).

Step 4: (2-{3-amino-5-[4-(trifluoromethoxy)benzene-1-sulfonyl]pyridin-2-yl}-1,3-thiazol-5-yl)methanol A solution of 2-{3-amino-5-[4-(trifluoromethoxy)benzene-1-sulfonyl]pyridin-2-yl}-1,3-thiazole-5-carbaldehyde (7 mg, 0.016 mmol, Step 3) in methanol (1 mL) was treated with excess NaBH$_4$ (5 mg), stirred at room temperature for 15 minutes, treated with 1 M aqueous HCl (5 mL) and extracted with ethyl acetate (30 mL). The ethyl acetate layer was washed with brine, dried (MgSO$_4$), filtered and concentrated to dryness. The residue was dissolved in a mixture of CH$_2$Cl$_2$ and ethyl acetate, treated with silica gel (~1.5 g) and concentrated to dryness. The silica gel suspension was transferred to a DASi™-12 cartridge atop a pre-equilibrated 4 g silica gel column. Chromatography via elution with a gradient of 50% to 100% ethyl acetate in heptanes provided the titled compound (3 mg, 6.95 μmol, 42.7% yield). MS (ESI−) m/z 430 [M−H]$^−$; $^1$H NMR (400 MHz, CDCl$_3$) δ ppm 8.38 (d, J=1.7 Hz, 1H), 8.04-8.00 (m, 2H), 7.77 (s, 1H), 7.54 (d, J=1.7 Hz, 1H), 7.35 (d, J=8.0 Hz, 2H), 6.43 (s, 2H), 4.93 (d, J=5.9 Hz, 2H), 1.90 (d, J=5.9 Hz, 1H).

EXAMPLE 6

2-(1,3,4-oxadiazol-2-yl)-5-[4-(trifluoromethoxy)benzene-1-sulfonyl]pyridin-3-amine A solution of iodobenzene (696 mg, 2.162 mmol), (2,2,6,6-tetramethyl-piperidin-1-yl)oxyl (TEMPO, 45.0 mg, 0.288 mmol) and (5-(3-amino-5-((4-(trifluoromethoxy)phenyl)sulfonyl)pyridin-2-yl)-1,3,4-oxadiazol-2-yl)methanol (300 mg, 0.721 mmol, Example 1) in 1,4-dioxane (20 mL) and water (6.00 mL) was stirred at ambient temperature for 30 minutes. LC/MS analysis showed mainly desired product. The mixture was extracted with 60 mL of ethyl acetate and 20 mL of water. The organic layer was separated and the solvent was removed in vacuo. The crude material was stirred in 20 mL ethyl acetate, and filtered to give the titled compound (177 mg, 0.458 mmol, 63.6% yield). $^1$H NMR (400 MHz, DMSO-$d_6$) δ ppm 9.44 (s, 1H), 8.44 (d, J=2.0 Hz, 1H), 8.21-8.12 (m, 2H), 7.93 (d, J=2.1 Hz, 1H), 7.67 (dd, J=9.0, 1.2 Hz, 2H), 7.30 (s, 2H); MS (ESI+) m/z 387 (M+H)$^+$.

EXAMPLE 7

(5-{3-amino-5-[4-(trifluoromethyl)benzene-1-sulfonyl]pyridin-2-yl}-1,3,4-oxadiazol-2-yl)methanol Step 1: 3-amino-5-((4-(trifluoromethyl)phenyl)thio)picolinic acid A solution of 3-amino-5-bromopicolinic acid (15.00 g, 69.1 mmol) in N,N-dimethylformamide (150 mL) and 4-(trifluoromethyl)benzenethiol (11.37 mL, 83 mmol) was sparged with N$_2$ for 20 minutes. N-ethyl-N-isopropylpropan-2-amine (24.14 mL, 138 mmol) was added to the reaction mixture. The reaction mixture was heated to 100° C. under an atmosphere of N$_2$ for 4 hours. The reaction was slowly poured into a mixture of 150 mL water and 20 mL 1 M aqueous HCl solution, which had been cooled to 0° C. The formed solid in the flask containing the reaction mixture was washed with water (100 mL) and petroleum (30 mL×3), and then dried under reduced pressure to give the titled compound (19.5 g, 61.4 mmol, 89% yield). MS (ESI+) m/z 315.1 (M+H)$^+$.

Step 2: 3-amino-5-((4-(trifluoromethyl)phenyl)sulfonyl)picolinic acid

3-Amino-5-((4-(trifluoromethyl)phenyl)thio)picolinic acid (2.000 g, 6.36 mmol) was dissolved in trifluoroacetic acid (TFA, 15 mL) and the resulting mixture was cooled to 0° C. with an ice bath. Next, H$_2$O$_2$ (2.60 mL, 25.5 mmol, 30% in water) was added at 0° C., and the mixture was stirred at 0° C. for 1 hour. The mixture was allowed to warm to 20° C. and was stirred for 2 hours. The slurry was diluted with a mixture of 1% acetic acid in water. A suspension was obtained and the mixture was subsequently filtered. The collected solid was washed with a 1% acetic acid/water mixture and then dichloromethane/methanol (10/1, 20 mL). The solid was dried under reduced pressure to give the titled compound (1.96 g, 5.66 mmol, 89% yield). $^1$H NMR (400 MHz, DMSO-$d_6$) δ ppm 8.28 (d, J=2.0 Hz, 1H), 8.22 (d, J=8.3 Hz, 2H), 8.06 (d, J=8.4 Hz, 2H), 7.82 (d, J=2.0 Hz, 1H), 7.12 (brs, 2H); MS (ESI+) m/z 347 (M+H)$^+$.

Step 3: 3-amino-N'-(2-hydroxyacetyl)-5-((4-(trifluoromethyl)phenyl)sulfonyl)picolino hydrazide 3-Amino-5((4-(trifluoromethyl)phenyl)sulfonyl)picolinic acid (3.00 g, 8.66 mmol), 3H-[1,2,3]triazolo[4,5-b]pyridin-3-ol (0.059 g, 0.433 mmol), and 2-hydroxyacetohydrazide (0.858 g, 9.53 mmol) were added to N,N-dimethylformamide (20 mL). The mixture was stirred at 25° C. for 10 minutes. 1-(3-Dimethylaminopropyl)-3-ethylcarbodiimide hydrochloride (2.491 g, 13.00 mmol) was added all at once. The mixture was stirred at 45° C. for 2 hours. Water (20 mL) was added. The mixture was filtered, washed with ethyl acetate (3×10 mL), and dried under reduced pressure to give the titled compound (3.4 g, 7.96 mmol, 92% yield); MS (ESI+) m/z 419.7 (M+H)$^+$.

Step 4: 3-amino-5-((4-(trifluoromethyl)phenyl)sulfonyl)-N'-(2-((triisopropylsilyl)oxy)acetyl)picolinohydrazide To a mixture of 3-amino-N'-(2-hydroxyacetyl)-5-((4-(trifluoromethyl)phenyl)sulfonyl)picolinohydrazide (6.00 g, 14.34 mmol) in N,N-dimethyl formamide (50 mL) was added triethylamine (5.00 mL, 35.9 mmol). The mixture was cooled to 0° C., and trifluoromethyl triisopropylsilanesulfonate (5.03 mL, 18.64 mmol) was added. The reaction mixture was stirred at 20° C. for 3 hours. Water (100 mL) was added. The solid was filtered, washed with water (50 mL×2), washed with ethyl acetate (2×15 mL), and dried under reduced pressure to give the titled compound (7.2 g, 12.53 mmol, 87% yield). MS (ESI+) m/z 575.7 (M+H)+.

Step 5: 5-((4-(trifluoromethyl)phenyl)sulfonyl)-2-(5-(((triisopropylsilyl)oxy)methyl)-1,3,4-oxadiazol-2-yl)pyridin-3-amine A 250 mL three round bottom flask equipped with a stirring magnet was charged with 3-amino-5-((4-(trifluoromethyl)phenyl)sulfonyl)-N'-(2-((triisopropylsilyl)oxy)acetyl)picolinohydrazide (3.50 g, 6.09 mmol) and put under an atmosphere of $N_2$. N, N-Dimethylpyridin-4-amine (0.074 g, 0.609 mmol), 4-methylbenzene-1-sulfonyl chloride (1.742 g, 9.14 mmol), and acetonitrile (35 mL) were added, resulting in a slurry. The reaction mixture was heated to 50° C. N-Ethyl-N-isopropylpropan-2-amine (3.72 mL, 21.32 mmol) was added slowly via syringe (internal temperature increased to 50° C. during addition) causing the reaction mixture to become homogenous. The reaction mixture was stirred at 50° C. for 1 hour. The mixture was concentrated, and water (15 mL) was added. The mixture was filtered, and the solid was washed with water (15 mL×2) and methanol (2×10 mL). The solid was dried under reduced pressure to provide the titled compound (3.2 g, 5.12 mmol, 84% yield). MS (ESI+) m/z 557.2 (M+H)+.

Step 6: (5-{3-amino-5-[4-(trifluoromethyl)benzene-1-sulfonyl]pyridin-2-yl}-1,3,4-oxadiazol-2-yl)methanol A solution of 5-((4-(trifluoromethyl)phenyl)sulfonyl)-2-(5-(((triisopropylsilyl)oxy)methyl)-1,3,4-oxadiazol-2-yl)pyridin-3-amine (5.80 g, 10.42 mmol) in acetonitrile (50 mL) was mixed at room temperature for 5 minutes. tetra-N-Butylammonium fluoride (1.0 M TBAF, 10.94 mL, 10.94 mmol) in tetrahydrofuran was added. The reaction mixture was stirred at room temperature for 1 hour. After completion, the reaction was concentrated to about 10 mL. Water was added (30 mL). The solid was filtered, and washed with water (2×30 mL) and methanol (15 mL×3). The solid was dried under vacuum to provide the titled compound (3.57 g, 8.92 mmol, 86% yield). $^1$H NMR (400 MHz, DMSO-$d_6$) δ ppm 8.46 (d, J=1.8 Hz, 1H), 8.25 (d, J=8.2 Hz, 2H), 8.07 (d, J=8.3 Hz, 2H), 7.94 (d, J=1.8 Hz, 1H), 7.30 (s, 2H), 6.04 (s, 1H), 4.76 (d, J=6.3 Hz, 2H); MS (ESI+) m/z 401.0 (M+H)+.

EXAMPLE 8

5-{3-amino-5-[4-(trifluoromethoxy)benzene-1-sulfonyl]pyridin-2-yl}-1,3,4-oxadiazole-2-carboxamide

Step 1: 2-(2-(3-amino-5-((4-(trifluoromethoxy)phenyl)sulfonyl)picolinoyl)hydrazinyl)-2-oxoacetamide A 20 mL vial was charged with 3-amino-5-((4-(trifluoromethoxy)phenyl)sulfonyl)picolinic acid (0.5 g, 1.380 mmol, step 2 Example 1), 2-hydrazinyl-2-oxoacetamide (0.213 g, 2.070 mmol), 3H-[1,2,3]triazolo[4,5-b]pyridin-3-ol (9.39 mg, 0.069 mmol), and N,N-dimethylformamide (3 mL). The mixture was stirred at room temperature for 15 minutes. 1-(3-Dimethylaminopropyl)-3-ethylcarbodiimide hydrochloride (0.397 g, 2.070 mmol) was added all at once, and the mixture was heated at 45° C. for an hour. Water (8 mL) was added. The mixture was stirred for 30 minutes at room temperature and filtered to provide the titled compound (0.431 g, 0.963 mmol, 69.8% yield). $^1$H NMR (400 MHz, DMSO-$d_6$) δ ppm 10.53 (s, 1H), 10.46 (s, 1H), 8.23 (d, J=2.0 Hz, 1H), 8.18-8.13 (m, 3H), 7.87 (s, 1H), 7.78 (d, J=2.1 Hz, 1H), 7.66 (d, J=7.9 Hz, 1H), 7.21 (s, 2H); MS (APCI+) m/z 448 (M+H)+.

Step 2: 5-{3-amino-5-[4-(trifluoromethoxy)benzene-1-sulfonyl]pyridin-2-yl}-1,3,4-oxadiazole-2-carboxamide A 20 mL vial was charged with 2-(2-(3-amino-5-((4-(trifluoromethoxy)phenyl)sulfonyl)picolinoyl)hydrazinyl)-2-oxoacetamide (390 mg, 0.872 mmol, Step 1), 4-dimethylaminopyridine (10.65 mg, 0.087 mmol), p-toluenesulfonyl chloride (316 mg, 1.656 mmol), and acetonitrile (5.1 mL). The resulting slurry was heated at 45° C. Hunig's Base (N,N-diisopropylethylamine, 0.533 mL, 3.05 mmol) was added dropwise slowly and heating was continued at 45° C. for two hours. Water (8 mL) was added and the slurry was stirred for 30 minutes at room temperature. The solid was paper filtered using gravity. The solid was dissolved in 5 mL of DMSO with heat at 60° C., cooled, and filtered. The resulting solid was dried under vacuum for 16 hours to provide the pure titled compound (180 mg, 0.420 mmol, 48.1% yield). $^1$H NMR (400 MHz, DMSO-$d_6$) δ ppm 8.68 (s, 1H), 8.46 (d, J=2.1 Hz, 1H), 8.29 (s, 1H), 8.22-8.13 (m, 2H), 7.95 (d, J=2.1 Hz, 1H), 7.67 (dt, J=7.9, 1.1 Hz, 2H), 7.32 (s, 2H); MS (APCI+) m/z 430 (M+H)+.

EXAMPLE 9

{5-[3-amino-5-(4-fluorobenzene-1-sulfonyl)pyridin-2-yl]-1,3,4-oxadiazol-2-yl}methanol

Step 1: 3-amino-5-((4-fluorophenyl)thio)picolinic acid

3-Amino-5-bromopicolinic acid (5 g, 23.04 mmol) was stirred in N,N-dimethylformamide (50 mL). 4-Fluorobenzenethiol (3.54 g, 27.6 mmol) and N,N-diisopropylethylamine (8.05 mL, 46.1 mmol) were added. The reaction mixture was heated at 100° C. for 5 hours. The mixture was cooled to room temperature. The reaction mixture was slowly poured into ice water, and the pH was adjusted to 5 with 1N aqueous HCl solution. The solid was filtered and washed with cold water, followed by petroleum ether, to give the titled compound (5.6 g, 20.77 mmol, 90% yield); MS (ESI+) m/z 265.7 (M+H)+.

Step 2: 3-amino-5-((4-fluorophenyl)sulfonyl)picolinic acid

3-Amino-5((4-fluorophenyl)thio)picolinic acid (3 g, 11.35 mmol) was dissolved in trifluoroacetic acid (21 mL) and the resulting mixture was cooled to 0° C. with an ice bath. Hydrogen peroxide (4.64 mL, 45.4 mmol, 30% in water) was added at 0° C., and the mixture was stirred at 0° C. for 1 hour. The mixture was allowed to warm to 20° C.

and was stirred for 1 hour. The reaction mixture was diluted with a mixture of 1% acetic acid in water (150 mL). A suspension was obtained that was subsequently filtered. The collected solid was washed with ice water (200 mL), and dried under reduced pressure to provide the titled compound (3.0 g, 10.02 mmol, 88% yield). $^1$H NMR (400 MHz, DMSO-$d_6$) δ ppm 8.25 (s, 1H), 8.11-8.07 (m, 2H), 8.06 (d, J=8.4 Hz, 2H), 7.78 (s, 1H), 7.53 (t, J=8.8 Hz, 2H), 7.12 (brs, 2H); MS (ESI+) m/z 297.7 (M+H)$^+$.

Step 3: 3-amino-5-((4-fluorophenyl)sulfonyl)-N'-(2-hydroxyacetyl)picolinohydrazide 3-Amino-5-((4-fluorophenyl)sulfonyl)picolinic acid (5 g, 16.88 mmol), 1-hydroxy-7-azabenzotriazole (0.115 g, 0.844 mmol) and 2-hydroxyacetohydrazide (1.672 g, 18.56 mmol) in dimethyl formamide (30 mL) was stirred at 25° C. for 10 minutes. 1-(3-Dimethylaminopropyl)-3-ethylcarbodiimide hydrochloride (4.85 g, 25.3 mmol) was added all at once at the internal temperature of 25° C. The solution was stirred at 25° C. for 10 minutes, and heated to 45° C. for 1 hour. The reaction mixture was added to ice water and was stirred for 3 hours. The solid was collected by filtration and washed with ice water to provide the titled compound (5.7 g, 14.70 mmol, 87% yield). MS (ESI+) m/z 369.7 (M+H)$^+$.

Step 4: 3-amino-5-((4-fluorophenyl)sulfonyl)-N'-(2 ((triisopropylsilyl)oxy)acetyl)picolinohydrazide A solution of 3-amino-54(4-fluorophenyl)sulfonyl)-N'-(2-hydroxyacetyl)picolinohydrazide (6.2 g, 16.83 mmol) was stirred in N,N-dimethyl formamide (45 mL) at 0° C. Triethylamine (7.04 mL, 50.5 mmol) was added, and triisopropylsilyl trifluoromethanesulfonate (8.77 g, 28.6 mmol) was added slowly. The reaction mixture was stirred at 20° C. for 16 hours. The reaction mixture was added to ice water and was stirred for 2 hours. The solid was collected by filtration and was washed with ice water to provide the titled compound (8.5 g, 15.39 mmol, 91% yield). MS (ESI+) m/z 525.7 (M+H)$^+$.

Step 5: 5-((4-fluorophenyl)sulfonyl)-2-(5-(((triisopropylsilyl)oxy)methyl)-1,3,4-oxadiazol-2-yl)pyridin-3-amine A solution of 3-amino-54(4-fluorophenyl)sulfonyl)-N'-(2-((triisopropylsilyl)oxy)acetyl)picolinohydrazide (4 g, 7.62 mmol), N,N-dimethylpyridin-4-amine (0.931 g, 7.62 mmol) and 4-methylbenzene-1-sulfonyl chloride (1.453 g, 7.62 mmol) was stirred in acetonitrile (40 mL). The reaction mixture was heated to 45° C. N-Ethyl-N-isopropylpropan-2-amine (0.985 g, 7.62 mmol) was added slowly. The reaction mixture was heated at 45° C. for 2 hours, and then was cooled to room temperature. Water was added and the mixture was stirred for 1 hour. The mixture was filtered, and the solid was washed with water to provide the titled compound (3.8 g, 7.13 mmol, 93% yield). MS (ESI+) m/z 507.7 (M+H)$^+$.

Step 6: (5-(3-amino-5-((4-fluorophenyl)sulfonyl) pyridin-2-yl)-1,3,4-oxadiazol-2-yl)methanol A mixture of 5-(4-fluorophenyl)sulfonyl)-2-(5-(((triisopropylsilyl)oxy)methyl)-1,3,4-oxadiazol-2-yl)pyridin-3-amine (8 g, 15.79 mmol) was stirred for 5 minutes in acetonitrile (120 mL). tetra-N-Butylammonium fluoride (18.95 mL, 18.95 mmol) was added. The reaction mixture was stirred at 20° C. for 2 hours. The reaction mixture was cooled to room temperature. A solution of 0.53 mL of 85% $H_3PO_4$ in 75 mL of water was added slowly to the reaction mixture. The resulting slurry was stirred at 20° C. for 3 hours. The solid was filtered and washed with 35 mL of a 1:5 (v/v) solution of $CH_3CN$/water, washed with 15 mL water, and dried under vacuum to provide the titled compound (5.06 g, 14.15 mmol, 90% yield). $^1$H NMR (400 MHz, DMSO-$d_6$) δ ppm 8.42 (d, J=2.0 Hz, 1H), 8.13-8.08 (m, 2H), 7.90 (d, J=2.0 Hz, 1H), 7.53 (t, J=10.4 Hz, 2H), 7.27 (s, 2H), 6. (t, J=6.2 Hz, 1H), 4.75 (d, J=6.4 Hz, 2H); MS (ESI+) m/z 351.7 (M+H)$^+$.

EXAMPLE 10

2-(5-cyclohexyl-1,3,4-oxadiazol-2-yl)-5-[4-(trifluoromethoxy)benzene-1-sulfonyl]pyridin-3-amine Step 1: tert-butyl 2-(3-amino-5-((4-(trifluoromethoxy)phenyl)sulfonyl)picolinoyl)hydrazinecarboxylate Into a 20 mL vial was added 3-amino-5-((4-(trifluoromethoxy)phenyl)sulfonyl)picolinic acid (100 mg, 0.276 mmol) in N,N-dimethylacetamide (4 mL). 2-(3H-[1,2,3] Triazolo[4,5-b]pyridin-3-yl)-1,1,3,3-tetramethylisouronium hexafluorophosphate(V) (115 mg, 0.304 mmol) and N-ethyl-N-isopropylpropan-2-amine (0.145 mL, 0.828 mmol) were added, followed by tert-butyl hydrazinecarboxylate (43.8 mg, 0.331 mmol). The reaction mixture was stirred at room temperature for 1 hour. The solvent was removed under a stream of nitrogen. The residue was diluted with 4 mL ethyl acetate and washed with water (1×5 mL). The organic layer was concentrated and purified using silica gel chromatography (using ethyl acetate in heptanes as the gradient, 5-100%, 4 g column) to provide the titled compound. $^1$H NMR (400 MHz, DMSO-$d_6$) δ ppm 10.16 (s, 1H), 8.82 (s, 1H), 8.18 (d, J=2.1 Hz, 1H), 8.17-8.04 (m, 2H), 7.74 (d, J=2.1 Hz, 1H), 7.68-7.56 (m, 2H), 7.18 (s, 2H), 1.39 (s, 9H).

Step 2: 3-amino-5-((4-(trifluoromethoxy)phenyl) sulfonyl)picolinohydrazide

Trifluoroacetic acid (1 mL, 12.98 mmol) was added to tert-butyl 2-(3-amino-5-((4-(trifluoromethoxy)phenyl)sulfonyl)picolinoyl)hydrazinecarboxylate, and the reaction mixture was stirred at room temperature for 1 hour. The solvent was removed under a stream of nitrogen. The crude material was suspended in 1 mL heptanes and stirred overnight. The resulting solid was collected via filtration to give the titled compound. $^1$H NMR (501 MHz, DMSO-$d_6$:$D_2O$=9:1 (v/v)) δ ppm 8.25 (d, J=2.1 Hz, 1H), 8.17-8.10 (m, 2H), 7.82 (d, J=2.0 Hz, 1H), 7.65 (dq, J=7.9, 1.1 Hz, 2H).

Step 3: 3-amino-N'-(cyclohexanecarbonyl)-5-((4-(trifluoromethoxy)phenyl)sulfonyl)picolinohydrazide Into a 4 mL vial was added cyclohexanecarboxylic acid (25.7 mg, 0.201 mmol), 2-(3H-[1,2,3]triazolo[4,5-b]pyridin-3-yl)-1,1,3,3-tetramethylisouronium hexafluorophosphate (V) (70.0 mg, 0.184 mmol) and N-ethyl-N-isopropylpropan-2-amine (0.088 mL, 0.502 mmol) in N,N-dimethylacetamide (1 mL). 3-Amino-5-((4-(trifluoromethoxy)phenyl)sulfonyl)picolinohydrazide (63 mg, 0.167 mmol) was added and the reaction mixture was stirred at room temperature for 1 hour. The reaction mixture was purified using the reverse phase TFA6 purification procedure to provide the titled compound (20 mg, 24.6% yield). $^1$H NMR (501 MHz, DMSO-d$_6$:D$_2$O=9:1 (v/v)) δ ppm 8.24 (d, J=2.0 Hz, 1H), 8.20-8.12 (m, 2H), 7.76 (d, J=2.0 Hz, 1H), 7.69-7.63 (m, 2H), 2.28-2.18 (m, 1H), 1.77-1.68 (m, 3H), 1.62 (d, J=12.6 Hz, 1H), 1.43-1.12 (m, 6H).

Step 4: 2-(5-cyclohexyl-1,3,4-oxadiazol-2-yl)-5-[4-(trifluoromethoxy)benzene-1-sulfonyl]pyridin-3-amine In a 4 mL vial, 3-amino-N'-(cyclohexanecarbonyl)-5-((4-(trifluoromethoxy)phenyl)sulfonyl)picolinohydrazide (20 mg, 0.041 mmol) was added to acetonitrile (1 mL). p-Toluenesulfonyl chloride (15.68 mg, 0.082 mmol) and N-ethyl-N-isopropylpropan-2-amine (0.022 mL, 0.123 mmol) were added and the reaction mixture was stirred at room temperature overnight. The reaction mixture was only 50% complete by HPLC, so the reaction mixture was heated to 65° C. over the weekend. The mixture was directly purified using preparative HPLC/MS method TFA6 to provide the titled compound (5.2 mg, 27% yield). $^1$H NMR (400 MHz, DMSO-d$_6$:D$_2$O=9:1 (v/v)) δ ppm 8.43 (d, J=2.0 Hz, 1H), 8.17 (d, J=8.9 Hz, 2H), 7.89 (d, J=2.1 Hz, 1H), 7.66 (dd, J=8.8, 1.2 Hz, 2H), 3.17-2.99 (m, 1H), 2.05 (d, J=12.0 Hz, 2H), 1.83-1.20 (m, 8H); MS (APCI+) m/z 469.0 (M+H)$^+$.

Example 11

2-{5-[(S)-methoxy(phenyl)methyl]-1,3,4-oxadiazol-2-yl}-5-[4-(trifluoromethoxy)benzene-1-sulfonyl]pyridin-3-amine The titled compound was prepared according to the procedure described in Example 10, substituting (S)-2-methoxy-2-phenylacetic acid for cyclohexanecarboxylic acid. $^1$H NMR (400 MHz, DMSO-d$_6$:D$_2$O=9:1 (v/v)) δ ppm 8.42 (d, J=2.0 Hz, 1H), 8.16 (d, J=8.9 Hz, 2H), 7.90 (d, J=2.1 Hz, 1H), 7.70-7.61 (m, 2H), 7.52-7.36 (m, 5H), 5.89 (s, 1H), 3.41 (s, 3H); MS (APCI+) m/z 506.9 (M+H)$^+$.

Example 12

2-{5-[(cyclopropylmethoxy)methyl]-1,3,4-oxadiazol-2-yl}-5-[4-(trifluoromethoxy)benzene-1-sulfonyl]pyridin-3-amine The title compound was prepared according to the procedure described in Example 10, substituting 2-(cyclopropylmethoxy)acetic acid for cyclohexanecarboxylic acid. $^1$H NMR (400 MHz, DMSO-d$_6$:D$_2$O=9:1 (v/v)) δ ppm 8.45 (d, J=2.1 Hz, 1H), 8.19 (d, J=8.9 Hz, 2H), 7.92 (d, J=2.0 Hz, 1H), 7.70-7.64 (m, 2H), 4.82 (s, 2H), 3.39 (d, J=7.0 Hz, 2H), 1.09-0.94 (m, 1H), 0.56-0.40 (m, 2H), 0.24-0.15 (m, 2H); MS (APCI+) m/z 471.0 (M+H)$^+$.

Example 13

2-[5-(phenoxymethyl)-1,3,4-oxadiazol-2-yl]-5-[4-(trifluoromethoxy)benzene-1-sulfonyl]pyridin-3-amine The titled compound was prepared according to the procedure described in Example 10, substituting 2-phenoxyacetic acid for cyclohexanecarboxylic acid. $^1$H NMR (500 MHz, DMSO-d$_6$:D$_2$O=9:1 (v/v)) δ ppm 8.44 (d, J=2.0 Hz, 1H), 8.18 (d, J=9.0 Hz, 2H), 7.92 (d, J=2.0 Hz, 1H), 7.66 (d, J=8.4 Hz, 2H), 7.34 (dd, J=8.8, 7.3 Hz, 2H), 7.09 (d, J=1.1 Hz, 2H), 7.03 (t, J=7.4 Hz, 1H), 5.51 (s, 2H); MS (APCI+) m/z 492.9 (M+H)$^+$.

Example 14

2-{5-[(cyclopentyloxy)methyl]-1,3,4-oxadiazol-2-yl}-5-[4-(trifluoromethoxy)benzene-1-sulfonyl]pyridin-3-amine The title compound was prepared according to the procedure described in Example 10, substituting 2-(cyclopentyloxy)acetic acid for cyclohexanecarboxylic acid. $^1$H NMR (400 MHz, DMSO-d$_6$:D$_2$O=9:1 (v/v)) δ ppm 8.45 (d, J=2.0 Hz, 1H), 8.18 (d, J=8.9 Hz, 2H), 7.92 (d, J=2.0 Hz, 1H), 7.71-7.62 (m, 2H), 4.75 (s, 2H), 4.13-4.03 (m, 1H), 1.83-1.39 (m, 8H); MS (APCI+) m/z 485.0 (M+H)$^+$.

Example 15

5-[4-(trifluoromethoxy)benzene-1-sulfonyl]-2-{5-[(trifluoromethoxy)methyl]-1,3,4-oxadiazol-2-yl}pyridin-3-amine The titled compound was prepared according to the procedure described in Example 10, substituting 2-(trifluoromethoxy)acetic acid for cyclohexanecarboxylic acid. $^1$H NMR (400 MHz, DMSO-d$_6$:D$_2$O=9:1 (v/v)) δ ppm 8.46 (d, J=2.0 Hz, 1H), 8.19 (d, J=8.9 Hz, 2H), 7.94 (d, J=2.0 Hz, 1H), 7.77-7.62 (m, 2H), 5.62 (s, 2H); MS (APCI+) m/z 484.9 (M+H)$^+$.

Example 16

2-(5-{[(oxolan-3-yl)oxy]methyl}-1,3,4-oxadiazol-2-yl)-5-[4-(trifluoromethoxy)benzene-1-sulfonyl]pyridin-3-amine The titled compound was prepared according to the procedure described in Example 10, substituting 2-((tetrahydrofuran-3-yl)oxy)acetic acid for cyclohexanecarboxylic acid. $^1$H NMR (400 MHz, DMSO-d$_6$:D$_2$O=9:1 (v/v)) δ ppm 8.45 (d, J=2.1 Hz, 1H), 8.19 (d, J=9.0 Hz, 2H), 7.92 (d, J=2.0 Hz, 1H), 7.72-7.56 (m, 2H), 4.83 (s, 2H), 4.39-4.30 (m, 1H), 3.79-3.59 (m, 4H), 2.14-1.76 (m, 2H); MS (APCI+) m/z 486.9 (M+H)$^+$.

Example 17

2-{5-[(2-methoxyethoxy)methyl]-1,3,4-thiadiazol-2-yl}-5-[4-(trifluoromethoxy)benzene-1-sulfonyl]pyridin-3-amine Step 1: 3-amino-N'-(2-(2-methoxyethoxy)acetyl)-5-((4-(trifluoromethoxy)phenyl)sulfonyl)picolinohydrazide Into a 4 mL vial was added 2-(2-methoxyethoxy)acetic acid (0.4 M in N,N-dimethylacetamide, 199 µL, 0.08 mmol, 1.5 eq) and 2-(3H-[1,2,3]triazolo[4,5-b]pyridin-3-yl)-1,1,3,3-tetramethylisouronium hexafluorophosphate(V) (0.12 M in N,N-dimethylacetamide, 500 µL, 0.063 mmol, 1.2 eq). 3-Amino-5-((4-(trifluoromethoxy)phenyl)sulfonyl)picolinohydrazide from Step 2 in Example 10 (0.10 M in N,N-dimethylacetamide, 500 µL, 0.053 mmol, 1.0 eq) was added, followed by N-ethyl-N-isopropylpropan-2-amine (27 µL, 0.16 mmol, 3.0 eq) and the reaction mixture was stirred at room temperature for 1 hour. The reaction mixture was purified using reverse phase procedure TFA6 to provide the titled compound.

Step 2: 2-{5-[(2-methoxyethoxy)methyl]-1,3,4-thiadiazol-2-yl}-5-[4-(trifluoromethoxy)benzene-1-sulfonyl]pyridin-3-amine The compound from Step 1 was transferred to a 4 mL vial and toluene (500 µL) was added. Lawesson's reagent (32 mg, 0.08 mmol, 1.5 eq) was added neat to the vial and the reaction was heated to 110° C. for 1 hour. The solvent was removed under a stream of nitrogen. Water and dichloromethane were added and the mixture was vortexed. The organic phase was removed, dried under a stream of nitrogen, and reconstituted in DMSO/CH₃OH. The crude material was purified using reverse phase HPLC/MS method AA7 to provide the titled compound (6.4 mg, 25% yield). $^1$H NMR (400 MHz, DMSO-$d_6$:$D_2O$=9:1 (v/v)) δ ppm 8.40 (d, J=2.0 Hz, 1H), 8.19 (d, J=8.9 Hz, 2H), 7.91 (d, J=2.0 Hz, 1H), 7.72-7.62 (m, 2H), 4.96 (s, 2H), 3.74-3.68 (m, 2H), 3.55-3.48 (m, 2H), 3.27 (s, 3H); MS (APCI+) m/z 490.9 (M+H)⁺.

Example 18

N-[(5-{3-amino-5-[4-(trifluoromethoxy)benzene-1-sulfonyl]pyridin-2-yl}-1,3,4-thiadiazol-2-yl)methyl]cyclopropanecarbothioamide The titled compound was prepared according to the procedure described in Example 17, substituting 2-(cyclopropanecarboxamido)acetic acid for 2-(2-methoxyethoxy)acetic acid. $^1$H NMR (400 MHz, DMSO-$d_6$:$D_2O$=9:1 (v/v)) δ ppm 8.38 (d, J=2.0 Hz, 1H), 8.18 (d, J=8.9 Hz, 2H), 7.89 (d, J=2.0 Hz, 1H), 7.75-7.60 (m, 2H), 5.22 (s, 2H), 2.21-2.04 (m, 1H), 1.12-0.99 (m, 2H), 0.99-0.84 (m, 2H); MS (APCI+) m/z 515.8 (M+H)⁺.

Example 19

2-{5-[(S)-methoxy(phenyl)methyl]-1,3,4-thiadiazol-2-yl}-5-[4-(trifluoromethoxy)benzene-1-sulfonyl]pyridin-3-amine The titled compound was prepared according to the procedure described in Example 17, substituting (S)-methoxy-phenyl-acetic acid for 2-(2-methoxyethoxy)acetic acid. $^1$H NMR (400 MHz, DMSO-$d_6$:$D_2O$=9:1 (v/v)) δ ppm 8.38 (d, J=2.0 Hz, 1H), 8.17 (d, J=8.9 Hz, 2H), 7.88 (d, J=2.0 Hz, 1H), 7.70-7.62 (m, 2H), 7.52-7.31 (m, 5H), 5.89 (s, 1H), 3.41 (s, 3H); MS (APCI+) m/z 522.8 (M+H)⁺.

Example 20

(2S)-2-(5-{3-amino-5-[4-(trifluoromethoxy)benzene-1-sulfonyl]pyridin-2-yl}-1,3,4-thiadiazol-2-yl)-1,1,1-trifluoropropan-2-ol The titled compound was prepared according to the procedure described in Example 17, substituting (R)-3,3,3-trifluoro-2-hydroxy-2-methylpropanoic acid for 2-(2-methoxyethoxy)acetic acid. $^1$H NMR (400 MHz, DMSO-$d_6$:$D_2O$=9:1 (v/v)) δ ppm 8.40 (d, J=2.0 Hz, 1H), 8.19 (d, J=8.9 Hz, 2H), 7.92 (d, J=2.0 Hz, 1H), 7.70-7.64 (m, 3H), 1.86 (s, 3H); MS (APCI+) m/z 514.7 (M+H)⁺.

Example 21

2-{5-[(1R)-1-methoxyethyl]-1,3,4-thiadiazol-2-yl}-5-[4-(trifluoromethoxy)benzene-1-sulfonyl]pyridin-3-amine The titled compound was prepared according to the procedure described in Example 17, substituting (R)-2-methoxypropanoic acid for 2-(2-methoxyethoxy)acetic acid. $^1$H NMR (400 MHz, DMSO-$d_6$:$D_2O$=9:1 (v/v)) δ ppm 8.40 (d, J=2.0 Hz, 1H), 8.26-8.14 (m, 2H), 7.90 (d, J=2.0 Hz, 1H), 7.73-7.60 (m, 2H), 4.88 (q, J=6.5 Hz, 1H), 3.35 (s, 3H), 1.55 (d, J=6.5 Hz, 3H); MS (APCI+) m/z 460.9 (M+H)⁺.

Example 22

2-[5-(1-methoxyethyl)-1,3,4-thiadiazol-2-yl]-5-[4-(trifluoromethoxy)benzene-1-sulfonyl]pyridin-3-amine The titled compound was prepared according to the procedure described in Example 17, substituting 2-methoxypropanoic acid for 2-(2-methoxyethoxy)acetic acid. $^1$H NMR (400 MHz, DMSO-$d_6$:$D_2O$=9:1 (v/v)) δ ppm 8.40 (d, J=2.0 Hz, 1H), 8.19 (d, J=8.9 Hz, 2H), 7.90 (d, J=2.0 Hz, 1H), 7.75-7.62 (m, 2H), 4.88 (q, J=6.5 Hz, 1H), 3.35 (s, 3H), 1.56 (d, J=6.5 Hz, 3H); MS (APCI+) m/z 460.9 (M+H)⁺.

Example 23

2-{5-[(1S)-1-methoxyethyl]-1,3,4-thiadiazol-2-yl}-5-[4-(trifluoromethoxy)benzene-1-sulfonyl]pyridin-3-amine The titled compound was prepared according to the procedure described in Example 17, substituting (S)-2-methoxypropanoic acid for 2-(2-methoxyethoxy)acetic acid. $^1$H NMR (400 MHz, DMSO-$d_6$:$D_2O$=9:1 (v/v)) δ ppm 8.40 (d, J=2.0 Hz, 1H), 8.19 (d, J=8.9 Hz, 2H), 7.90 (d, J=2.0 Hz, 1H), 7.75-7.62 (m, 2H), 4.88 (q, J=6.5 Hz, 1H), 3.35 (s, 3H), 1.56 (d, J=6.5 Hz, 3H); MS (APCI+) m/z 460.9 (M+H)⁺.

Example 24

2-{5-[(cyclopropylmethoxy)methyl]-1,3,4-thiadiazol-2-yl}-5-[4-(trifluoromethoxy)benzene-1-sulfonyl]pyridin-3-amine The titled compound was prepared according to the procedure described in Example 17, substituting 2-(cyclopropylmethoxy)acetic acid for 2-(2-methoxyethoxy)acetic acid. $^1$H NMR (400 MHz, DMSO-$d_6$:$D_2O$=9:1 (v/v)) δ ppm 8.40 (d, J=2.0 Hz, 1H), 8.18 (d, J=8.9 Hz, 2H), 7.90 (d, J=2.0 Hz, 1H), 7.78-7.55 (m, 2H), 4.95 (s, 2H), 3.42 (d, J=6.9 Hz, 2H), 1.13-0.86 (m, 1H), 0.58-0.43 (m, 2H), 0.29-0.11 (m, 2H); MS (APCI+) m/z 486.9 (M+H)⁺.

Example 25

2-[5-(ethoxymethyl)-1,3,4-thiadiazol-2-yl]-5-[4-(trifluoromethoxy)benzene-1-sulfonyl]pyridin-3-amine The titled compound was prepared according to the procedure described in Example 17, substituting 2-ethoxyacetic acid for 2-(2-methoxyethoxy)acetic acid. $^1$H NMR (400 MHz, DMSO-$d_6$:$D_2O$=9:1 (v/v)) δ ppm 8.40 (d, J=2.0

Hz, 1H), 8.18 (d, J=8.9 Hz, 2H), 7.90 (d, J=2.0 Hz, 1H), 7.71-7.63 (m, 2H), 4.92 (s, 2H), 3.62 (q, J=7.0 Hz, 2H), 1.18 (t, J=7.0 Hz, 3H); MS (APCI+) m/z 460.9 (M+H)+.

Example 26

2-[5-(methoxymethyl)-1,3,4-thiadiazol-2-yl]-5-[4-(trifluoromethoxy)benzene-1-sulfonyl]pyridin-3-amine The titled compound was prepared according to the procedure described in Example 17, substituting 2-methoxyacetic acid for 2-(2-methoxyethoxy)acetic acid. $^1$H NMR (400 MHz, DMSO-d$_6$:D$_2$O=9:1 (v/v)) δ ppm 8.40 (d, J=2.0 Hz, 1H), 8.19 (d, J=8.9 Hz, 2H), 7.91 (d, J=2.0 Hz, 1H), 7.73-7.57 (m, 2H), 4.89 (s, 2H), 3.42 (s, 3H); MS (APCI+) m/z 446.8 (M+H)+.

Example 27

2-(5-{[(pyridin-3-yl)oxy]methyl}-1,3,4-thiadiazol-2-yl)-5-[4-(trifluoromethoxy)benzene-1-sulfonyl]pyridin-3-amine The titled compound was prepared according to the procedure described in Example 17, substituting 2-(pyridin-3-yloxy)acetic acid hydrochloride for 2-(2-methoxyethoxy)acetic acid. $^1$H NMR (400 MHz, DMSO-d$_6$:D$_2$O=9:1 (v/v)) δ ppm 8.61-8.54 (m, 1H), 8.40 (d, J=2.0 Hz, 1H), 8.37 (d, J=5.0 Hz, 1H), 8.18 (d, J=8.9 Hz, 2H), 7.92 (d, J=2.0 Hz, 1H), 7.87 (dd, J=8.6, 2.9 Hz, 1H), 7.72-7.56 (m, 3H), 5.79 (s, 2H); MS (APCI+) m/z 509.8 (M+H)+.

Example 28

5-[4-(trifluoromethoxy)benzene-1-sulfonyl]-2-{5-[(trifluoromethoxy)methyl]-1,3,4-thiadiazol-2-yl}pyridin-3-amine The titled compound was prepared according to the procedure described in Example 17, substituting 2-(trifluoromethoxy)acetic acid for 2-(2-methoxyethoxy)acetic acid. $^1$H NMR (400 MHz, DMSO-d$_6$:D$_2$O=9:1 (v/v)) δ ppm 8.41 (d, J=2.0 Hz, 1H), 8.19 (d, J=8.9 Hz, 2H), 7.93 (d, J=2.0 Hz, 1H), 7.73-7.61 (m, 2H), 5.70 (s, 2H); MS (APCI+) m/z 500.8 (M+H)+.

Example 29

2-(5-{[(oxolan-3-yl)oxy]methyl}-1,3,4-thiadiazol-2-yl)-5-[4-(trifluoromethoxy)benzene-1-sulfonyl]pyridin-3-amine The titled compound was prepared according to the procedure described in Example 17, substituting 2-((tetrahydrofuran-3-yl)oxy)acetic acid for 2-(2-methoxyethoxy)acetic acid. $^1$H NMR (400 MHz, DMSO-d$_6$:D$_2$O=9:1 (v/v)) δ ppm 8.40 (d, J=2.0 Hz, 1H), 8.23-8.13 (m, 2H), 7.90 (d, J=2.0 Hz, 1H), 7.70-7.65 (m, 2H), 4.95 (s, 2H), 4.40-4.33 (m, 1H), 3.84-3.76 (m, 2H), 3.72-3.63 (m, 2H), 2.04-1.93 (m, 2H); MS (APCI+) m/z 502.9 (M+H)+.

Example 30

2-{5-[(difluoromethoxy)methyl]-1,3,4-thiadiazol-2-yl}-5-[4-(trifluoromethoxy)benzene-1-sulfonyl]pyridin-3-amine The titled compound was prepared according to the procedure described in Example 17, substituting 2-(difluoromethoxy)acetic acid for 2-(2-methoxyethoxy)acetic acid. $^1$H NMR (400 MHz, DMSO-d$_6$:D$_2$O=9:1 (v/v)) δ ppm 8.41 (d, J=2.0 Hz, 1H), 8.19 (d, J=8.9 Hz, 2H), 7.92 (d, J=2.0 Hz, 1H), 7.67 (dd, J=8.9, 1.1 Hz, 2H), 6.88 (t, J=74.2 Hz, 1H), 5.43 (s, 2H); MS (APCI+) m/z 482.8 (M+H)+.

Example 31

2-(5-{[(2S)-oxolan-2-yl]methyl}-1,3,4-thiadiazol-2-yl)-5-[4-(trifluoromethoxy)benzene-1-sulfonyl]pyridin-3-amine The titled compound was prepared according to the procedure described in Example 17, substituting (S)-2-(tetrahydrofuran-2-yl)acetic acid for 2-(2-methoxyethoxy)acetic acid. $^1$H NMR (400 MHz, DMSO-d$_6$:D$_2$O=9:1 (v/v)) δ ppm 8.39 (d, J=2.0 Hz, 1H), 8.18 (d, J=8.9 Hz, 2H), 7.88 (d, J=2.1 Hz, 1H), 7.71-7.62 (m, 2H), 4.21-4.13 (m, 1H), 3.86-3.61 (m, 2H), 3.44-3.18 (m, 2H), 2.03 (dd, J=12.7, 6.3 Hz, 1H), 1.89-1.78 (m, 2H), 1.54 (dd, J=12.2, 7.6 Hz, 1H); MS (APCI+) m/z 486.9 (M+H)+.

Example 32

2-(5-{[(2R)-oxolan-2-yl]methyl}-1,3,4-thiadiazol-2-yl)-5-[4-(trifluoromethoxy)benzene-1-sulfonyl]pyridin-3-amine The titled compound was prepared according to the procedure described in Example 17, substituting (R)-2-(tetrahydrofuran-2-yl)acetic acid for 2-(2-methoxyethoxy)acetic acid. $^1$H NMR (400 MHz, DMSO-d$_6$:D$_2$O=9:1 (v/v)) δ ppm 8.39 (d, J=2.0 Hz, 1H), 8.18 (d, J=8.9 Hz, 2H), 7.88 (d, J=2.0 Hz, 1H), 7.70-7.58 (m, 2H), 4.24-4.11 (m, 1H), 3.85-3.58 (m, 2H), 3.42-3.18 (m, 2H), 2.03 (dq, J=13.1, 6.8 Hz, 1H), 1.90-1.75 (m, 2H), 1.62-1.45 (m, 1H); MS (APCI+) m/z 486.9 (M+H)+.

Example 33

2-{5-[(2-methoxyethoxy)methyl]-1,3,4-oxadiazol-2-yl}-5-[4-(trifluoromethoxy)benzene-1-sulfonyl]pyridin-3-amine The titled compound was prepared according to the procedure described in Example 10, substituting 2-(2-methoxyethoxy)acetic acid for cyclohexanecarboxylic acid. $^1$H NMR (500 MHz, DMSO-d$_6$:D$_2$O=9:1 (v/v)) δ ppm 8.44 (d, J=2.0 Hz, 1H), 8.18 (d, J=8.9 Hz, 2H), 7.92 (d, J=2.1 Hz, 1H), 7.70-7.62 (m, 2H), 4.84 (s, 2H), 3.70-3.66 (m, 2H), 3.50-3.47 (m, 2H), 3.23 (s, 3H); MS (APCI+) m/z 474.8 (M+H)+.

Example 34

2-{5-[(1R)-1-methoxyethyl]-1,3,4-oxadiazol-2-yl}-5-[4-(trifluoromethoxy)benzene-1-sulfonyl]pyridin-3-amine The titled compound was prepared according to the procedure described in Example 10, substituting (R)-2-methoxypropanoic acid for cyclohexanecarboxylic acid. $^1$H NMR (500 MHz, DMSO-d$_6$:D$_2$O=9:1 (v/v)) δ ppm 8.45 (d, J=2.0 Hz, 1H), 8.18 (d, J=9.0 Hz, 2H), 7.91 (d, J=2.0 Hz, 1H), 7.72-7.60 (m, 2H), 4.82 (q, J=6.6 Hz, 1H), 3.31 (s, 3H), 1.55 (d, J=6.6 Hz, 3H); MS (APCI+) m/z 444.8 (M+H)+.

Example 35

2-{5-[(1S)-1-methoxyethyl]-1,3,4-oxadiazol-2-yl}-5-[4-(trifluoromethoxy)benzene-1-sulfonyl]pyridin-3-amine The titled compound was prepared according to the procedure described in Example 10, substituting (S)-2-methoxypropanoic acid for cyclohexanecarboxylic acid. $^1$H NMR (500 MHz, DMSO-$d_6$:D$_2$O=9:1 (v/v)) δ ppm 8.45 (d, J=2.0 Hz, 1H), 8.18 (d, J=8.9 Hz, 2H), 7.91 (d, J=2.1 Hz, 1H), 7.67 (d, J=8.4 Hz, 3H), 4.81 (q, J=6.7 Hz, 1H), 3.31 (s, 3H), 1.55 (d, J=6.6 Hz, 3H); MS (APCI+) m/z 444.8 (M+H)$^+$.

Example 36

2-[5-(ethoxymethyl)-1,3,4-oxadiazol-2-yl]-5-[4-(trifluoromethoxy)benzene-1-sulfonyl]pyridin-3-amine The titled compound was prepared according to the procedure described in Example 10, substituting 2-ethoxyacetic acid for cyclohexanecarboxylic acid. $^1$H NMR (500 MHz, DMSO-$d_6$:D$_2$O=9:1 (v/v)) δ ppm 8.44 (d, J=2.0 Hz, 1H), 8.18 (d, J=8.9 Hz, 2H), 7.92 (d, J=2.1 Hz, 1H), 7.75-7.62 (m, 2H), 4.79 (s, 2H), 3.59 (q, J=7.0 Hz, 2H), 1.15 (t, J=7.0 Hz, 3H); MS (APCI+) m/z 444.9 (M+H)$^+$.

Example 37

2-[5-(methoxymethyl)-1,3,4-oxadiazol-2-yl]-5-[4-(trifluoromethoxy)benzene-1-sulfonyl]pyridin-3-amine The titled compound was prepared according to the procedure described in Example 10, substituting 2-methoxyacetic acid for cyclohexanecarboxylic acid. $^1$H NMR (500 MHz, DMSO-$d_6$:D$_2$O=9:1 (v/v)) δ ppm 8.44 (d, J=2.1 Hz, 1H), 8.18 (d, J=8.9 Hz, 2H), 7.92 (d, J=2.1 Hz, 1H), 7.74-7.64 (m, 2H), 4.77 (s, 2H), 3.38 (s, 3H); MS (APCI+) m/z 430.9 (M+H)$^+$.

Example 38

2-(5-{[(pyridin-3-yl)oxy]methyl}-1,3,4-oxadiazol-2-yl)-5-[4-(trifluoromethoxy)benzene-1-sulfonyl]pyridin-3-amine The titled compound was prepared according to the procedure described in Example 10, substituting 2-(pyridin-3-yloxy)acetic acid hydrochloride for cyclohexanecarboxylic acid. $^1$H NMR (500 MHz, DMSO-$d_6$:D$_2$O=9:1 (v/v)) δ ppm 8.52-8.38 (m, 3H), 8.31-8.24 (m, 1H), 8.18 (d, J=8.9 Hz, 2H), 7.92 (d, J=2.0 Hz, 1H), 7.72-7.57 (m, 3H), 7.46 (dd, J=8.5, 4.7 Hz, 2H), 5.64 (s, 2H); MS (APCI+) m/z 493.8 (M+H)$^+$.

Example 39

2-{5-[(difluoromethoxy)methyl]-1,3,4-oxadiazol-2-yl}-5-[4-(trifluoromethoxy)benzene-1-sulfonyl]pyridin-3-amine The titled compound was prepared according to the procedure described in Example 10, substituting 2-(difluoromethoxy)acetic acid for cyclohexanecarboxylic acid. $^1$H NMR (500 MHz, DMSO-$d_6$:D$_2$O=9:1 (v/v)) δ ppm 8.45 (d, J=2.0 Hz, 1H), 8.25-8.13 (m, 2H), 7.93 (d, J=2.0 Hz, 1H), 7.73-7.60 (m, 2H), 6.87 (t, J=73.9 Hz, 1H), 5.31 (s, 2H); MS (APCI+) m/z 466.9 (M+H)$^+$.

Example 40

2-(5-{[(2S)-oxolan-2-yl]methyl}-1,3,4-oxadiazol-2-yl)-5-[4-(trifluoromethoxy)benzene-1-sulfonyl]pyridin-3-amine The titled compound was prepared according to the procedure described in Example 10, substituting (S)-2-(tetrahydrofuran-2-yl)acetic acid for cyclohexanecarboxylic acid. $^1$H NMR (500 MHz, DMSO-$d_6$:D$_2$O=9:1 (v/v)) δ ppm 8.43 (d, J=2.0 Hz, 1H), 8.25-8.11 (m, 2H), 7.90 (d, J=2.1 Hz, 1H), 7.70-7.60 (m, 2H), 4.31-4.20 (m, 1H), 3.65-3.57 (m, 2H), 3.28-3.02 (m, 2H), 2.13-1.99 (m, 1H), 1.93-1.76 (m, 2H), 1.74-1.57 (m, 1H); MS (APCI+) m/z 470.9 (M+H)$^+$.

Example 41

2-(5-{[(2R)-oxolan-2-yl]methyl}-1,3,4-oxadiazol-2-yl)-5-[4-(trifluoromethoxy)benzene-1-sulfonyl]pyridin-3-amine The titled compound was prepared according to the procedure described in Example 10, substituting (R)-2-(tetrahydrofuran-2-yl)acetic acid for cyclohexanecarboxylic acid. $^1$H NMR (500 MHz, DMSO-$d_6$:D$_2$O=9:1 (v/v)) δ ppm 8.43 (d, J=2.1 Hz, 1H), 8.21-8.14 (m, 2H), 7.90 (d, J=2.1 Hz, 1H), 7.70-7.64 (m, 2H), 4.29-4.22 (m, 1H), 3.64 (s, 2H), 3.24-3.08 (m, 2H), 2.12-2.03 (m, 1H), 1.90-1.81 (m, 2H), 1.71-1.61 (m, 1H); MS (APCI+) m/z 470.9 (M+H)$^+$.

Example 42

1-(5-{3-amino-5-[4-(trifluoromethoxy)benzene-1-sulfonyl]pyridin-2-yl}-1,3,4-oxadiazol-2-yl)ethan-1-ol Step 1: (S)-3-amino-N'-(2-hydroxypropanoyl)-5-((4-(trifluoromethoxy)phenyl)sulfonyl)picolinohydrazide In a 4 mL vial was added (S)-2-hydroxypropanoic acid (10.8 mg, 0.12 mmol, 1.5 eq) and 2-(3H-[1,2,3]triazolo[4,5-b]pyridin-3-yl)-1,1,3,3-tetramethylisouronium hexafluorophosphate(V) (36.4 mg, 0.10 mmol, 1.2 eq) in N,N-dimethylacetamide (1.0 mL). 3-Amino-54(4-(trifluoromethoxy)phenyl)sulfonyl)picolinohydrazide from Example 10 Step 2 (30.0 mg, 0.08 mmol, 1.0 eq) was added, followed by N-ethyl-N-isopropylpropan-2-amine (42 μL, 0.24 mmol, 3.0 eq). The reaction was stirred at room temperature for 1 hour. The reaction was purified using reverse phase method TFA10 to provide the titled compound.

Step 2: (S)-3-amino-5-((4-(trifluoromethoxy)phenyl)sulfonyl)-N'-(2-((triisopropylsilyl)oxy)propanoyl)picolinohydrazide Purified material from Step 1 was suspended in 500 μL dichloromethane. Triethylamine (30 μL, 0.21 mmol, 2.5 eq) was added followed by TIPS Triflate (triisopropylsilyl trifluoromethanesulfonate, 50 μL, 0.21 mmol, 2.5 eq). The reaction mixture was stirred for 1 hour at room temperature. The reaction mixture was washed twice with water. The organic layer was separated, dried with Na$_2$SO$_4$, and filtered. The filtrate was concentrated to provide the titled compound.

Step 3: (5)-5-((4-(trifluoromethoxy)phenyl)sulfonyl)-2-(5-(1-((triisopropylsilyl)oxy)ethyl)-1,3,4-oxadiazol-2-yl)pyridin-3-amine The residue from Step 2 was dissolved in 500 μL CH$_3$CN. 4-(Dimethylamino)pyridine (0.007 M, 1 mL, 0.007 mmol, 0.1 eq) and p-toluenesulfonyl chloride (0.14 M, 1 mL, 0.14 mmol, 1.9 eq) stock solutions were added, followed by diisopropylethylamine (50 μL, 0.29 mmol, 4.0 eq). The reaction mixture was heated at 45° C. for 1 hour and then purified directly via reverse phase using method TFA8.

Step 4: 1-(5-{3-amino-5-[4-(trifluoromethoxy)benzene-1-sulfonyl]pyridin-2-yl}-1,3,4-oxadiazol-2-yl)ethan-1-ol The compound from Step 3 was dissolved in tetrahydrofuran (500 Tetrabutyl ammonium fluoride (1 M in tetrahydrofuran, 70 μL, 0.07 mmol, 1.0 eq) was added at room temperature and the reaction mixture was stirred until complete by LC. The reaction mixture was purified via preparative reverse phase HPLC/MS method TFA8. After purification, the sample still contained trace tetrabutylammonium salts and was repurified using the same method to provide the titled compound. $^1$H NMR (501 MHz, DMSO-d$_6$:D$_2$O=9:1 (v/v)) δ ppm 8.44 (d, J=2.1 Hz, 1H), 8.21-8.14 (m, 2H), 7.91 (d, J=2.1 Hz, 1H), 7.70-7.64 (m, 2H), 5.05 (q, J=6.6 Hz, 1H), 1.54 (d, J=6.7 Hz, 3H); MS (APCI+) m/z 430.9 (M+H)$^+$.

Example 43

2-(5-{3-amino-5-[4-(trifluoromethoxy)benzene-1-sulfonyl]pyridin-2-yl}-1,3,4-oxadiazol-2-yl)propan-2-ol The titled compound was prepared according to the procedure described in Example 42, substituting 2-hydroxy-2-methylpropanoic acid for (S)-2-hydroxypropanoic acid. $^1$H NMR (501 MHz, DMSO-d$_6$:D$_2$O=9:1 (v/v)) δ ppm 8.45 (d, J=2.0 Hz, 1H), 8.21-8.14 (m, 2H), 7.91 (d, J=2.0 Hz, 1H), 7.70-7.64 (m, 2H), 1.61 (s, 6H); MS (APCI+) m/z 444.9 (M+H)$^+$.

Example 44

(1S)-1-(5-{3-amino-5-[4-(trifluoromethoxy)benzene-1-sulfonyl]pyridin-2-yl}-1,3,4-oxadiazol-2-yl)-2-phenyl ethan-1-ol The titled compound was prepared according to the procedure described in Example 42, substituting (S)-2-hydroxy-3-phenylpropanoic acid for (S)-2-hydroxypropanoic acid. $^1$H NMR (400 MHz, DMSO-d$_6$:D$_2$O=9:1 (v/v)) δ ppm 8.46 (d, J=2.0 Hz, 1H), 8.23-8.14 (m, 2H), 7.91 (d, J=2.0 Hz, 1H), 7.68 (d, J=8.4 Hz, 2H), 7.31-7.17 (m, 5H), 5.12 (t, J=7.2 Hz, 1H), 3.20 (dd, J=7.1, 4.7 Hz, 2H); MS (APCI+) m/z 506.9 (M+H)$^+$.

Example 45

(S)-(5-{3-amino-5-[4-(trifluoromethoxy)benzene-1-sulfonyl]pyridin-2-yl}-1,3,4-oxadiazol-2-yl)(phenyl)methanol The titled compound was prepared according to the procedure described in Example 42, substituting (S)-2-hydroxy-2-phenylacetic acid for (S)-2-hydroxypropanoic acid. $^1$H NMR (400 MHz, DMSO-d$_6$:D$_2$O=9:1 (v/v)) δ ppm 8.40 (d, J=2.0 Hz, 1H), 8.19-8.10 (m, 2H), 7.88 (d, J=2.0 Hz, 1H), 7.68-7.60 (m, 2H), 7.51-7.44 (m, 2H), 7.44-7.29 (m, 3H), 6.11 (s, 1H); MS (APCI+) m/z 492.9 (M+H)$^+$.

Example 46

2-[3-(2-methoxypropan-2-yl)-1,2,4-oxadiazol-5-yl]-5-[4-(trifluoromethoxy)benzene-1-sulfonyl]pyridin-3-amine Into a 4 mL vial was added 3-amino-5-((4-(trifluoromethoxy)phenyl)sulfonyl)picolinic acid (60.4 mg, 0.167 mmol, 1.0 eq) in N,N-dimethyl acetamide (1 mL). 2-(3H-[1,2,3]Triazolo[4,5-b]pyridin-3-yl)-1,1,3,3-tetramethylisouronium hexafluorophosphate(V) (69.7 mg, 0.183 mmol, 1.1 eq) and N-ethyl-N-isopropylpropan-2-amine (0.087 mL, 0.500 mmol, 3.0 eq) were added, followed by (Z)—N'-hydroxy-2-methoxy-2-methylpropanimidamide (26.4 mg, 0.2 mmol, 1.2 eq). The reaction mixture was stirred at room temperature for 1 hour, at which point it was complete by LC/MS. The solvent was removed under a stream of nitrogen. The residue was diluted with 2 mL dichloromethane and washed with water (1×5 mL). The residue from the first step was diluted with 1 mL tetrahydrofuran. Tetrabutylammonium hydroxide (40% wt in water, 108 mg, 0.167 mmol) was added and the reaction mixture was stirred at room temperature for 3 hours. The solvent was removed under a stream of nitrogen. The residue was dissolved in 0.5 mL CH$_3$CN and was added to 4 mL stirring water for 30 minutes. The water was removed via pipette, and the solid was dissolved in DMSO and purified on reverse phase HPLC/MS using method TFA8. $^1$H NMR (400 MHz, DMSO-d$_6$:D$_2$O=9:1 (v/v)) δ ppm 8.47 (d, J=2.1 Hz, 1H), 8.26-8.15 (m, 2H), 7.99 (d, J=2.1 Hz, 1H), 7.74-7.67 (m, 2H), 3.12 (s, 3H), 1.63 (s, 6H); MS (APCI+) m/z 458.8 (M+H)$^+$.

Example 47

2-[3-(1-methoxyethyl)-1,2,4-oxadiazol-5-yl]-5-[4-(trifluoromethoxy)benzene-1-sulfonyl]pyridin-3-amine The titled compound was prepared according to the procedure described in Example 46, substituting N'-hydroxy-2-methoxy-propanamidine for (Z)—N'-hydroxy-2-methoxy-2-methylpropanimidamide and by purifying the sample after both the first and second steps. $^1$H NMR (400 MHz, DMSO-d$_6$:D$_2$O=9:1 (v/v)) δ ppm 8.44 (d, J=2.0 Hz, 1H), 8.23-8.14 (m, 2H), 7.96 (d, J=2.1 Hz, 1H), 7.72-7.63 (m, 2H), 4.69 (q, J=6.6 Hz, 1H), 3.28 (s, 3H), 1.53 (d, J=6.6 Hz, 3H); MS (APCI+) m/z 444.9 (M+H)$^+$.

Example 48

2-[3-(oxan-4-yl)-1,2,4-oxadiazol-5-yl]-5-[4-(trifluoromethoxy)benzene-1-sulfonyl]pyridin-3-amine The titled compound was prepared according to the procedure described in Example 46, substituting N'-hydroxytetrahydropyran-4-carboxamidine for (Z)—N'-hydroxy-2-methoxy-2-methylpropanimidamide and by purifying the sample after both the first and second steps. $^1$H NMR (400 MHz, DMSO-d$_6$:D$_2$O=9:1 (v/v)) δ ppm 8.43 (d, J=2.0 Hz, 1H), 8.23-8.14 (m, 2H), 7.94 (d, J=2.1 Hz, 1H), 7.71-

7.63 (m, 2H), 3.96-3.88 (m, 2H), 3.50 (td, J=11.5, 2.3 Hz, 2H), 3.27-3.14 (m, 1H), 2.01-1.93 (m, 2H), 1.87-1.72 (m, 2H); MS (APCI+) m/z 470.8 (M+H)+.

Example 49

2-{3-[(4-fluorophenoxy)methyl]-1,2,4-oxadiazol-5-yl}-5-[4-(trifluoromethoxy)benzene-1-sulfonyl]pyridin-3-amine The titled compound was prepared according to the procedure described in Example 46, substituting 2-(4-fluorophenoxy)-N'-hydroxy-acetamidine for (Z)—N'-hydroxy-2-methoxy-2-methylpropanimidamide and by purifying the sample after both the first and second steps. $^1$H NMR (400 MHz, DMSO-$d_6$:$D_2O$=9:1 (v/v)) δ ppm 8.44 (d, J=2.0 Hz, 1H), 8.23-8.14 (m, 2H), 7.94 (d, J=2.0 Hz, 1H), 7.71-7.63 (m, 2H), 7.20-7.06 (m, 4H), 5.38 (s, 2H); MS (APCI+) m/z 510.8 (M+H)+.

Example 50

2-[3-(cyclopropylmethyl)-1,2,4-oxadiazol-5-yl]-5-[4-(trifluoromethoxy)benzene-1-sulfonyl]pyridin-3-amine The titled compound was prepared according to the procedure described in Example 46, substituting 2-cyclopropyl-N'-hydroxy-acetamidine for (Z)—N'-hydroxy-2-methoxy-2-methylpropanimidamide and by purifying the sample after both the first and second steps. $^1$H NMR (400 MHz, DMSO-$d_6$:$D_2O$=9:1 (v/v)) δ ppm 8.43 (d, J=2.0 Hz, 1H), 8.23-8.14 (m, 2H), 7.94 (d, J=2.0 Hz, 1H), 7.71-7.63 (m, 2H), 2.75 (d, J=7.0 Hz, 2H), 1.19-1.14 (m, 1H), 0.58-0.49 (m, 2H), 0.32-0.24 (m, 2H); MS (APCI+) m/z 440.9 (M+H)+.

Example 51

2-{3-[(oxolan-2-yl)methyl]-1,2,4-oxadiazol-5-yl}-5-[4-(trifluoromethoxy)benzene-1-sulfonyl]pyridin-3-amine The titled compound was prepared according to the procedure described in Example 46, substituting N'-hydroxy-2-tetrahydrofuran-2-yl-acetamidine for (Z)—N'-hydroxy-2-methoxy-2-methylpropanimidamide and by purifying the sample after both the first and second steps. $^1$H NMR (400 MHz, DMSO-$d_6$:$D_2O$=9:1 (v/v)) δ ppm 8.43 (d, J=2.0 Hz, 1H), 8.23-8.14 (m, 2H), 7.94 (d, J=2.0 Hz, 1H), 7.71-7.63 (m, 2H), 4.29 (p, J=6.6 Hz, 1H), 3.80-3.74 (m, 1H), 3.65-3.56 (m, 1H), 3.00 (d, J=6.5 Hz, 2H), 2.11-1.98 (m, 1H), 1.94-1.77 (m, 2H), 1.71-1.57 (m, 1H); MS (APCI+) m/z 470.8 (M+H)+.

Example 52

2-(3-cyclopropyl-1,2,4-oxadiazol-5-yl)-5-[4-(trifluoromethoxy)benzene-1-sulfonyl]pyridin-3-amine The titled compound was prepared according to the procedure described in Example 46, substituting N'-hydroxycyclopropanecarboxamidine for (Z)—N'-hydroxy-2-methoxy-2-methylpropanimidamide and by purifying the sample after both the first and second steps. $^1$H NMR (400 MHz, DMSO-$d_6$:$D_2O$=9:1 (v/v)) δ ppm 8.41 (d, J=2.1 Hz, 1H), 8.22-8.13 (m, 2H), 7.93 (d, J=2.0 Hz, 1H), 7.71-7.63 (m, 2H), 2.28-2.17 (m, 1H), 1.19-1.09 (m, 2H), 1.10-1.01 (m, 2H); MS (APCI+) m/z 426.9 (M+H)+.

Example 53

2-[3-(oxolan-3-yl)-1,2,4-oxadiazol-5-yl]-5-[4-(trifluoromethoxy)benzene-1-sulfonyl]pyridin-3-amine The titled compound was prepared according to the procedure described in Example 46, substituting N'-hydroxytetrahydrofuran-3-carboxamidine for (Z)—N'-hydroxy-2-methoxy-2-methylpropanimidamide and by purifying the sample after both the first and second steps. $^1$H NMR (400 MHz, DMSO-$d_6$:$D_2O$=9:1 (v/v)) δ ppm 8.43 (d, J=2.1 Hz, 1H), 8.23-8.14 (m, 2H), 7.94 (d, J=2.1 Hz, 1H), 7.71-7.63 (m, 2H), 4.07 (dd, J=8.5, 7.6 Hz, 1H), 3.94-3.81 (m, 4H), 2.42-2.15 (m, 2H); MS (APCI+) m/z 456.9 (M+H)+.

Example 54

2-(3-tert-butyl-1,2,4-oxadiazol-5-yl)-5-[4-(trifluoromethoxy)benzene-1-sulfonyl]pyridin-3-amine The titled compound was prepared according to the procedure described in Example 46, substituting N'-hydroxy-2,2-dimethyl-propanamidine for (Z)—N'-hydroxy-2-methoxy-2-methylpropanimidamide and by purifying the sample after both the first and second steps. $^1$H NMR (400 MHz, DMSO-$d_6$:$D_2O$=9:1 (v/v)) δ ppm 8.42 (d, J=2.1 Hz, 1H), 8.22-8.14 (m, 2H), 7.95 (d, J=2.0 Hz, 1H), 7.71-7.63 (m, 2H), 1.39 (s, 9H); MS (APCI+) m/z 442.9 (M+H)+.

Example 55

2-[3-(2-methoxyethyl)-1,2,4-oxadiazol-5-yl]-5-[4-(trifluoromethoxy)benzene-1-sulfonyl]pyridin-3-amine The titled compound was prepared according to the procedure described in Example 46, substituting N'-hydroxy-3-methoxy-propanamidine for (Z)—N'-hydroxy-2-methoxy-2-methylpropanimidamide and by purifying the sample after both the first and second steps. $^1$H NMR (400 MHz, DMSO-$d_6$:$D_2O$=9:1 (v/v)) δ ppm 8.43 (d, J=2.1 Hz, 1H), 8.22-8.14 (m, 2H), 7.94 (d, J=2.0 Hz, 1H), 7.71-7.63 (m, 2H), 3.78 (t, J=6.2 Hz, 2H), 3.25 (s, 3H), 3.06 (t, J=6.3 Hz, 2H); MS (APCI+) m/z 444.9 (M+H)+.

Example 56

2-[3-(methoxymethyl)-1,2,4-oxadiazol-5-yl]-5-[4-(trifluoromethoxy)benzene-1-sulfonyl]pyridin-3-amine The titled compound was prepared according to the procedure described in Example 46, substituting N'-hydroxy-3-methoxy-acetamidine for (Z)—N'-hydroxy-2-methoxy-2-methylpropanimidamide and by purifying the sample after both the first and second steps. $^1$H NMR (400 MHz, DMSO-$d_6$:$D_2O$=9:1 (v/v)) δ ppm 8.47 (d, J=2.0 Hz, 1H), 8.27-8.18 (m, 2H), 7.98 (d, J=2.1 Hz, 1H), 7.74-7.66 (m, 2H), 7.41-7.35 (m, 2H), 4.70 (s, 2H), 3.42 (s, 3H); MS (APCI+) m/z 430.9 (M+H)+.

Example 57

(5-{3-amino-4-chloro-5-[4-(trifluoromethoxy)benzene-1-sulfonyl]pyridin-2-yl}-1,3,4-oxadiazol-2-yl)methanol {5-[3-Amino-5-(4-trifluoromethoxy-benzenesulfonyl)-pyridin-2-yl]-[1,3,4]oxadiazol-2-yl}-methanol (200 mg, 0.48 mmol) was dissolved in acetic acid (5 mL). N-Chlorosuccinimide was added (CAS: 128-09-6, 640 mg, 4.8 mmol) and the resulting mixture was stirred at room temperature for 18 hours. The reaction mixture was concentrated, water was added, and the resulting suspension was filtered to provide 250 mg of crude material. The crude material was purified by reverse phase preparative HPLC (97% 10 mM $NH_4HCO_3$/pH 10, 3% $CH_3CN$) to provide two regioisomers, Example 57 and Example 64. Example 57: $^1H$ NMR (600 MHz, DMSO-$d_6$) δ ppm 8.34 (s, 1H), 8.09-8.14 (m, 2H), 7.64-7.68 (m, 2H), 7.45 (br. s., 2H), 6.03 (t, J=6.4 Hz, 1H), 4.74 (d, J=6.4 Hz, 2H), MS (ESI+) m/z 451 [M+H]$^+$. Example 64: $^1H$ NMR (600 MHz, DMSO-$d_6$) δ ppm 8.68 (s, 1H), 8.16-8.20 (m, 2H), 7.65 (m, 2H), 7.40 (s, 2H), 6.07 (t, J=6.3 Hz, 1H), 4.78 (d, J=6.2 Hz, 2H), MS (ESI+) m/z 451 [M+H]$^+$.

Example 58

(5-{3-amino-5-[3-(trifluoromethoxy)benzene-1-sulfonyl]pyridin-2-yl}-1,3,4-oxadiazol-2-yl)methanol

Step 1: methyl 2-triisopropylsilyloxyacetate

Tri-isopropylchloride (CAS: 13154-24-0, 228 mL, 1067 mmol) was added to a solution of methyl-glycolate (CAS: 96-35-5, 80 g, 889 mmol) and imidazole (CAS: 288-32-4, 182 g, 1067 mmol) in dry N,N-dimethylformamide (1 L) under a N2 atmosphere. The resulting solution was stirred at room temperature. After stirring overnight, thin layer chromatography (ethyl acetate/petroleum ether, 35:65) showed full consumption of the starting material. The reaction mixture was quenched with 1.5 L of saturated aqueous $NaHCO_3$ solution. The resulting mixture was extracted with diethyl ether. The organic layer was subsequently washed with 1.4 L of 2N aqueous HCl (2.8 mol), 0.5 L of $H_2O$, and 1 L of brine. The organic layer was dried over $Na_2SO_4$, filtered and concentrated to dryness to give the crude titled compound which was used as such in the next step.

Step 2: 2-triisopropylsilyloxyacetohydrazide

Methyl 2-triisopropylsilyloxyacetate (199 g, 889 mmol) was dissolved in tetrahydrofuran (1 L). Hydrazine monohydrate (CAS: 7803-57-8, 35% w/w, 203 mL, 2.222 mol) was added, and the mixture was refluxed. After stirring overnight at reflux, thin layer chromatography (ethyl acetate/petroleum ether, 5:95) showed full consumption of the starting material. The reaction mixture was cooled and quenched with saturated aqueous $NaHCO_3$ solution (1.5 L). The resulting solution was extracted with diethyl ether (4×500 mL). The organic layer was dried over $Na_2SO_4$, filtered, and concentrated to dryness to provide 191 g of crude material as a waxy solid. Precipitation from ethyl acetate/heptane (5%, 500 mL), provided 122 g of the titled compound. $^1H$ NMR (400 MHz, $CDCl_3$) δ ppm 7.76 (s, 1H), 7.26 (s, 1H), 4.28 (s, 2H), 3.87 (d, J=4.3 Hz, 2H), 1.19-1.05 (m, 21H).

Step 3: 3-amino-5-(3-trifluoromethoxy-phenylsulfanyl)-pyridine-2-carboxylic acid A solution of 3-amino-5-bromo-pyridine-2-carboxylic acid (CAS: 870997-85-6, 500 mg, 2.3 mmol), 3-(trifluoromethoxy) benzenethiol (CAS: 220239-66-7, 534 mg, 2.76 mmol) and 1,8-diazabicyclo[5.4.0]undec-7-ene (0.344 mL, 2.3 mmol) was prepared in N,N-dimethylacetamide (2 mL). The mixture was heated at 150° C. for 45 minutes in a microwave reactor (Biotage, SW version 2.2). Water was added and the mixture was extracted with ethyl acetate. The organic layer was washed with saturated aqueous $NaHCO_3$, dried ($Na_2SO_4$), filtered, and concentrated to provide 783 mg of the titled compound.

Step 4: 3-amino-5-(3-trifluoromethoxy-benzenesulfonyl)-pyridine-2-carboxylic acid 3-Amino-5-(3-trifluoromethoxy-phenylsulfanyl)-pyridine-2-carboxylic acid (783 mg, 2.37 mmol) was dissolved in trifluoroacetic acid (5 mL), and the resulting mixture was cooled to 0° C. with an ice bath. Next, $H_2O_2$ (30% in water, 0.968 mL, 9.48 mmol) was added and the mixture was stirred at room temperature for 2 hours. The mixture was diluted with 1% acetic acid in water (10 mL). A suspension was obtained that was subsequently filtered. The collected solid was washed with 1% acetic acid followed by petroleum ether to provide 652 mg of the titled compound.

Step 5: 3-amino-5-(3-trifluoromethoxy-benzenesulfonyl)-pyridine-2-carboxylic acid N-(2-triisopropylsilanyloxy-acetyl)-hydrazide To a dichloromethane solution (10 mL) containing 3-amino-5-(3-trifluoromethoxy-benzenesulfonyl)-pyridine-2-carboxylic acid (336 mg, 0.93 mmol), was added diisopropylethylamine (0.323 mL, 1.86 mmol), N-[(dimethylamino)-1H-1,2,3-triazolo-[4,5-b]pyridin-1-ylmethylene]-N-methylmethanaminium hexafluorophosphate N-oxide (354 mg, 0.93 mmol) and 2-triisopropylsilyloxyacetohydrazide (231 mg, 0.93 mmol). The resulting mixture was stirred at room temperature until the reaction was complete. The mixture was diluted with water and extracted with dichloromethane. The organic layer was washed with $NaHCO_3$, dried ($Na_2SO_4$), filtered, and concentrated to provide 540 mg of the titled compound.

Step 6: 5-(3-trifluoromethoxy-benzenesulfonyl)-2-(5-triisopropylsilanyloxymethyl-[1,3,4]oxadiazol-2-yl)-pyridin-3-ylamine 3-Amino-5-(3-trifluoromethoxy-benzenesulfonyl)-pyridine-2-carboxylic acid N'-(2-triisopropylsilanyl oxy-acetyl)-hydrazide (540 mg, 0.91 mmol) was mixed with tosyl chloride (522 mg, 2.74 mmol) and triethylamine (381 μL, 2.74 mmol) in dichloromethane under an argon atmosphere. The reaction mixture was stirred at ambient temperature for 18 hours. The reaction mixture was quenched with 1N aqueous NaOH and subsequently extracted with dichloromethane. The organic layer was washed with water, dried over $Na_2SO_4$, filtered and concentrated to dryness to provide 670 mg of crude material. The crude material was purified by column chromatography (using dichloromethane as the eluent) to provide 68 mg of the titled compound.

Step 7: {5-[3-amino-5-(3-trifluoromethoxy-benzene-sulfonyl)-pyridin-2-yl]-[1,3,4]oxadiazol-2-yl}-methanol 5-(3-Trifluoromethoxy-benzenesulfonyl)-2-(5-triisopropylsilanyloxymethyl-[1,3,4]oxadiazol-2-yl)-pyridin-3-ylamine (68 mg, 0.12 mmol) was dissolved in tetrahydrofuran (2 mL). A solution of tetrabutyl ammonium fluoride (CAS: 429-41-4, 1M in tetrahydrofuran, 0.12 mL, 0.12 mmol) was added and the resulting mixture was stirred at room temperature for 10 minutes. The mixture was concentrated. The crude material was quenched with $H_2O$, extracted with ethyl acetate, dried ($Na_2SO_4$), filtered, and concentrated to provide 56 mg of crude material. After trituration in dichloromethane, 14 mg of the titled compound was obtained. $^1H$ NMR (500 MHz, DMSO-$d_6$) δ ppm 8.47 (d, J=2.1 Hz, 1H), 8.06 (m, 1H), 8.00 (s, 1H), 7.93 (d, J=1.8 Hz, 1H), 7.82-7.87 (m, 1H), 7.78-7.82 (m, 1H), 7.27 (s, 2H), 6.02 (t, J=6.4 Hz, 1H), 4.75 (d, J=6.4 Hz, 2H), MS (ESI+) m/z 417 [M+H]$^+$.

Example 59

(5-{3-amino-5-[2-(trifluoromethoxy)benzene-1-sulfonyl]pyridin-2-yl}-1,3,4-oxadiazol-2-yl)methanol The titled compound was prepared as described in Example 58, substituting 2-(trifluoromethoxy)-benzenethiol (CAS: 175278-01-0) for 3-(trifluoromethoxy) benzenethiol). $^1H$ NMR (500 MHz, DMSO-$d_6$) δ ppm 8.31 (d, J=2.1 Hz, 1H), 8.27 (m, 1H), 7.90-7.95 (m, 1H), 7.87 (d, J=1.8 Hz, 1H), 7.73 (m, 1H), 7.61 (d, J=8.2 Hz, 1H), 7.32 (s, 2H), 6.02 (t, J=6.4 Hz, 1H), 4.75 (d, J=6.4 Hz, 2H), MS (ESI+) m/z 417 [M+H]$^+$.

Example 60

5-amino-N-benzyl-6-[5-(hydroxymethyl)-1,3,4-oxadiazol-2-yl]-N-methylpyridine-3-sulfonamide Step 1: 3-amino-5-bromo-pyridine-2-carboxylic acid N-(2-triisopropylsilanyloxy-acetyl)-hydrazide To a dichloromethane solution (200 mL) containing 3-amino-5-bromo-pyridine-2-carboxylic acid (CAS: 870997-85-6, 10 g, 46 mmol) was added diisopropylethylamine (16 mL, 92 mmol), N-[(dimethylamino)-1H-1,2,3-triazolo-[4,5-b]pyridin-1-ylmethylene]-N-methylmethanaminium hexafluorophosphate N-oxide (17.49 g, 46 mmol) and 2-triisopropylsilyloxyacetohydrazide (11.35 g, 46 mmol). The resulting solution was stirred at room temperature for 18 hours. The mixture was diluted with water and extracted with dichloromethane. The organic layer was washed with saturated aqueous $NaHCO_3$, dried with $Na_2SO_4$, filtered, and concentrated to provide 25.37 g of the titled compound.

Step 2: 3-amino-5-(4-methoxy-benzylsulfanyl)-pyridine-2-carboxylic acid N'-(2-triisopropylsilanyloxy acetyl)-hydrazide A vessel filled with a mixture of 3-amino-5-bromo-pyridine-2-carboxylic acid, N'-(2-triisopropyl silanyloxy-acetyl)-hydrazide (1 g, 2.2 mmol), diisopropylethylamine (0.768 mL, 4.4 mmol) and toluene (10 mL) was evacuated and the reaction vessel was filled with argon. Next, s(dibenzylideneacetone)dipalladium(0)-chloroform adduct (68 mg, 007 mmol), Xantphos (4,5-bis(diphenylphosphino)-9,9-dimethylxanthene, 76 mg, 0.13 mmol) and (4-methoxy-phenyl)-methanethiol (432 mg, 2.8 mmol)) were added. The reaction vessel was filled with argon once more and the reaction mixture was stirred at 110° C. for 18 hours. The reaction mixture was filtered through a plug of silica (using ethyl acetate as the eluent) and concentrated to provide 759 mg of the titled compound.

Step 3: 5-(4-methoxy-benzylsulfanyl)-2-(5-triisopropylsilanyloxymethyl-[1,3,4]oxadiazol-2-yl)-pyridin-3-ylamine 3-Amino-5-(4-methoxy-benzylsulfanyl)-pyridine-2-carboxylic acid N'-(2-triisopropylsilanyloxy acetyl)-hydrazide (160 mg, 0.29 mmol) was mixed with tosyl chloride (166 mg, 0.87 mmol) and triethylamine (0.121 mL, 0.87 mmol) in dichloromethane (10 mL) under an argon atmosphere. The reaction mixture was stirred at ambient temperature for 2 days. The mixture was quenched with 1N aqueous NaOH and subsequently extracted with dichloromethane. The organic layer was washed with water, dried over $Na_2SO_4$, filtered and concentrated to dryness to provide 360 mg of crude material. The crude material was further purified by flash chromatography ($SiO_2$, 5 g column, eluted with dichloromethane) to provide 69 mg of the titled compound.

Step 4: 5-amino-6-(5-triisopropylsilanyloxymethyl-[1,3,4]oxadiazol-2-yl)-pyridine-3-sulfonyl chloride An mixture of 5-(4-methoxy-benzylsulfanyl)-2-(5-triisopropylsilanyloxymethyl[1,3,4]oxadiazol-2-yl)-pyridin-3-ylamine (69 mg, 0.14 mmol) in 2 mL of a mixture of $CH_3CN$/acetic acid/$H_2O$=7: 0.37: 0.18 was cooled in an ice bath and treated portionwise with 1,3-dichloro-5,5-dimethylhydantoin (CAS: 118-52-5, 54 mg, 0.28 mmol). When the addition was complete, the resulting suspension was stirred at 0° C. for 90 minutes and then at room temperature for 6 hours. The mixture was diluted with ethyl acetate and washed with water. The organic phase was dried over $Na_2SO_4$, filtered and concentrated to give 98 mg of the titled compound.

Step 5: 5-amino-6-(5-triisopropylsilanyloxymethyl-[1,3,4]oxadiazol-2-yl)-pyridine-3-sulfonic acid benzyl-methyl-amide A suspension of 5-amino-6-(5-triisopropylsilanyloxymethyl-[1,3,4]oxadiazol-2-yl)-pyridine-3-sulfonyl chloride (98 mg, 0.21 mmol) in dichloromethane (2 mL) was treated with pyridine (0.051 mL, 0.63 mmol) and N-methyl-benzylamine (CAS: 103-67-3, 0.037 mL, 0.28 mmol). The reaction mixture was stirred at room temperature for 18 hours. The reaction mixture was purified by column chromatography ($SiO_2$, 2 g column, dichloromethane as eluent) to provide 36 mg of the titled compound.

Step 6: 5-amino-N-benzyl-6-[5-(hydroxymethyl)-1,3,4-oxadiazol-2-yl]-N-methyl-pyridine-3-sulfonamide 5-Amino-6-(5-triisopropylsilanyloxymethyl-[1,3,4]oxadiazol-2-yl)-pyridine-3-sulfonic acid benzyl-methyl-amide (36 mg, 0.07 mmol) was dissolved in tetrahydrofuran (1 mL). A solution of tetrabutyl ammonium fluoride (TBAF, CAS: 429-41-4, 1 M in tetrahydrofuran, 0.02 mL, 0.02 mmol) was added and the resulting mixture was stirred at room temperature for 10 minutes. The mixture was concentrated to remove most of the tetrahydrofuran. The reaction mixture was quenched with H$_2$O, extracted with ethyl acetate, dried (with Na$_2$SO$_4$), filtered, and concentrated to provide 18 mg of crude product. The resulting crude material was triturated with dichloromethane to provide 3 mg of the titled compound. $^1$H NMR (500 MHz, DMSO-d$_6$) δ 8.31 (d, J=1.8 Hz, 1H), 7.82 (d, J=1.8 Hz, 1H), 7.36-7.42 (m, 3H), 7.33 (d, J=7.3 Hz, 2H), 7.23 (s, 2H), 6.04 (t, J=6.1 Hz, 1H), 4.77 (d, J=5.5 Hz, 2H), 4.23 (s, 2H), 2.63 (s, 3H), MS (ESI+) m/z 376 [M+H]$^+$.

Example 61

{5-[3-amino-5-(benzenesulfonyl)pyridin-2-yl]-1,3,4-oxadiazol-2-yl}methanol

The titled compound was prepared as described in Example 58 substituting 3-benzenethiol (CAS: 108-98-5) for 3-(trifluoromethoxy) benzenethiol. $^1$H NMR (500 MHz, DMSO-d$_6$) δ ppm 8.40 (d, J=1.8 Hz, 1H), 7.97-8.04 (m, 2H), 7.90 (d, J=2.1 Hz, 1H), 7.74-7.80 (m, 1H), 7.66-7.71 (m, 2H), 7.26 (br. s, 2H), 6.01 (t, J=6.4 Hz, 1H), 4.74 (d, J=6.4 Hz, 2H), MS (ESI+) m/z 333 [M+H]$^+$.

Example 62

(5-{3-amino-5-[4-(trifluoromethyl)benzene-1-sulfonyl]pyridin-2-yl}-1,3,4-thiadiazol-2-yl)methanol Step 1: 5-[4-(trifluoromethyl)phenyl]sulfonyl-2-[5-(triisopropylsilyloxymethyl)-1,3,4-thiadiazol-2-yl]pyridin-3-amine To a suspension of 3-amino-5-[4-(trifluoromethoxy)phenyl]sulfonyl-N'-(2-triisopropylsilyloxyacetyl) pyridine-2-carbohydrazide (200 mg, 0.35 mmol) in dry toluene (8 mL) was added Lawesson's reagent (CAS Number 19172-47-5, 155 mg, 0.38 mmol) and the solution was refluxed for 1 hour. Water was added and mixture was extracted with ethyl acetate, dried (with Na$_2$SO$_4$), filtered, and concentrated to provide 178 mg crude material. The crude material was purified by column chromatography (SiO$_2$, 2 g column, eluent was dichloromethane) to provide 107 mg of the titled compound.

Step 2: [5-[3-amino-5-[4-(trifluoromethyl)phenyl]sulfonyl-2-pyridyl]-1,3,4-thiadiazol-2-yl]methanol 5-[4-(Trifluoromethyl)phenyl]sulfonyl-2-[5-(triisopropylsilyloxymethyl)-1,3,4-thiadiazol-2-yl]pyridin-3-amine (107 mg, 0.18 mmol) was dissolved in tetrahydrofuran (3 mL). A solution of tetrabutyl ammonium fluoride (TBAF, CAS: 429-41-4, 1M in tetrahydrofuran, 0.18 mL, 0.18 mmol) was added and the resulting mixture was stirred at room temperature for 10 minutes. The mixture was concentrated to remove most of the tetrahydrofuran. The reaction mixture was quenched with H$_2$O, extracted with ethyl acetate, dried (with Na$_2$SO$_4$), filtered, and concentrated to provide 140 mg of crude material. After trituration with dichloromethane, 36 mg of the titled compound was obtained. $^1$H NMR (500 MHz, DMSO-d$_6$) δ ppm 8.42 (d, J=1.8 Hz, 1H), 8.24 (d, J=8.2 Hz, 2H), 8.05 (d, J=8.2 Hz, 2H), 7.91 (d, J=1.8 Hz, 1H), 7.49 (s, 2H), 6.29 (br. s., 1H), 4.89 (br. s., 2H), MS (ESI+) m/z 417 [M+H]$^+$, MS (ESI+) m/z 417 [M+H]$^+$.

Example 63

(5-{3-amino-6-bromo-5-[4-(trifluoromethoxy)benzene-1-sulfonyl]pyridin-2-yl}-1,3,4-oxadiazol-2-yl)methanol {5-[3-Amino-5-(4-trifluoromethoxy-benzenesulfonyl)-pyridin-2-yl]-[1,3,4]oxadiazol-2-yl}-methanol (200 mg, 0.48 mmol) was dissolved in acetic acid (5 mL). N-Bromosuccinimide was added (NBS, 85 mg, 0.48 mmol) and the resulting mixture was stirred at room temperature for 18 hours. Additional NBS was added (170 mg, 0.41 mmol) and the mixture was stirred at room temperature for another 24 hours. Again, an additional quantity of NBS was added (340 mg, 0.82 mmol) and mixture was stirred at room temperature for 24 hours. The reaction mixture was concentrated, water was added and reaction mixture was extracted with ethyl acetate and washed with saturated aqueous NaHCO$_3$. The organic phases were combined, dried (with Na$_2$SO$_4$), filtered, and concentrated to provide 380 mg of crude material. The crude material was purified by reverse phase preparative HPLC (using a mixture of eluents, 97% 10 mM NH$_4$HCO$_3$/pH 10 3% CH$_3$CN) to provide the titled compound (Example 63) and Example 66. Example 63: $^1$H NMR (600 MHz, DMSO-d$_6$) δ ppm 8.34 (s, 1H), 8.09-8.14 (m, 2H), 7.64-7.68 (m, 2H), 7.45 (br. s., 2H), 6.03 (t, J=6.4 Hz, 1H), 4.74 (d, J=6.4 Hz, 2H), MS (ESI+) m/z 496 [M+H]$^+$. Example 66: $^1$H NMR (600 MHz, DMSO-d$_6$) δ ppm 8.68 (s, 1H), 8.16 (d, 2H), 7.64 (m, 2H), 6.07 (t, J=6.4 Hz, 1H), 7.36 (br. s., 2H), 4.78 (d, J=6.4 Hz, 2H), MS (ESI+) m/z 496 [M+H]$^+$.

Example 64

(5-{3-amino-6-chloro-5-[4-(trifluoromethoxy)benzene-1-sulfonyl]pyridin-2-yl}-1,3,4-oxadiazol-2-yl)methanol {5-[3-Amino-5-(4-trifluoromethoxy-benzenesulfonyl)-pyridin-2-yl]-[1,3,4]oxadiazol-2-yl}-methanol (200 mg, 0.48 mmol) was dissolved in acetic acid (5 mL). N-Chlorosuccinimide was added (CAS: 128-09-6, 640 mg, 4.8 mmol) and the resulting mixture was stirred at room temperature for 18 hours. The reaction mixture was concentrated, water was added and the resulting suspension was filtered to provide 250 mg of crude product. The crude material was purified by reverse phase preparative HPLC (using mixture of eluents 97% 10 mM NH$_4$HCO$_3$/pH 10 3% CH$_3$CN) to provide both regioisomers, Example 57 and the titled compound. Example 64: $^1$H NMR (600 MHz, DMSO-d$_6$) δ ppm 8.68 (s, 1H), 8.16-8.20 (m, 2H), 7.65 (m, 2H), 7.40 (s, 2H), 6.07 (t, J=6.3 Hz, 1H), 4.78 (d, J=6.2 Hz, 2H), MS (ESI+) m/z 451 [M+H]$^+$.

Example 65

(5-{3-amino-5-[2-(propan-2-yl)benzene-1-sulfonyl]pyridin-2-yl}-1,3,4-oxadiazol-2-yl)methanol The titled compound was prepared as described in Example 58 substituting 2-isopropyl-benzenethiol (CAS: 6262-87-9) for 3-(trifluoromethoxy) benzenethiol. $^1$H NMR (600 MHz, DMSO-d$_6$) δ ppm 8.24 (d, J=2.1 Hz, 1H), 8.12

(m, 1H), 7.81 (d, J=2.1 Hz, 1H), 7.76 (m, 1H), 7.66 (m, 1H), 7.55 (m, 1H), 7.27 (s, 2H), 6.01 (t, J=6.4 Hz, 1H), 4.75 (d, J=6.1 Hz, 2H), 3.64 (m, 1H), 1.01 (d, J=6.7 Hz, 6H), MS (ESI+) m/z 375 [M+H]$^+$.

Example 66

(5-{3-amino-4-bromo-5-[4-(trifluoromethoxy)benzene-1-sulfonyl]pyridin-2-yl}-1,3,4-oxadiazol-2-yl)methanol 5-[3-Amino-5-(4-trifluoromethoxy-benzenesulfonyl)-pyridin-2-yl]-[1,3,4]oxadiazol-2-yl}-methanol (200 mg, 0.48 mmol) was dissolved in acetic acid (5 mL). N-Bromosuccinimide was added (NBS, 85 mg, 0.48 mmol) and the resulting mixture was stirred at room temperature for 18 hours. Additional NBS was added (170 mg, 0.41 mmol) and mixture was stirred at room temperature for another 24 hours. An additional quantity of NBS was added (340 mg, 0.82 mmol) and the mixture was stirred at room temperature for 24 hours. The reaction mixture was concentrated, water was added, and the reaction mixture was extracted with ethyl acetate and washed with saturated aqueous NaHCO$_3$. The organic phases were combined, dried (with Na$_2$SO$_4$), filtered, and concentrated to provide 380 mg of crude material. The crude material was purified by reverse phase preparative HPLC (using eluents, 97% 10 mM NH$_4$HCO$_3$/pH 10 3% CH$_3$CN) to provide the titled compound and Example 63. Example 63: $^1$H NMR (600 MHz, DMSO-d$_6$) δ ppm 8.34 (s, 1H), 8.09-8.14 (m, 2H), 7.64-7.68 (m, 2H), 7.45 (br. s., 2H), 6.03 (t, J=6.4 Hz, 1H), 4.74 (d, J=6.4 Hz, 2H), MS (ESI+) m/z 496 [M+H]$^+$. Example 66: $^1$H NMR (600 MHz, DMSO-d$_6$) δ ppm 8.68 (s, 1H), 8.16 (d, 2H), 7.64 (m, 2H), 6.07 (t, J=6.4 Hz, 1H), 7.36 (br. s., 2H), 4.78 (d, J=6.4 Hz, 2H), MS (ESI+) m/z 496 [M+H]$^+$.

Example 67

2-(5-{3-amino-5-[4-(trifluoromethoxy)benzene-1-sulfonyl]pyridin-2-yl}-1,2,4-oxadiazol-3-yl)ethan-1-ol The title compound was prepared according to the procedure described in Example 46, substituting N',3-dihydroxypropanimidamide for (Z)—N'-hydroxy-2-methoxy-2-methylpropanimidamide and by purifying the sample after both the first and second steps. $^1$H NMR (400 MHz, DMSO-d$_6$) δ ppm 8.44 (d, J=2.1 Hz, 1H), 8.20-8.14 (m, 2H), 7.94 (d, J=2.1 Hz, 1H), 7.74-7.60 (m, 2H), 7.37 (s, 2H), 4.83 (t, J=5.5 Hz, 1H), 3.84 (q, J=6.2 Hz, 2H), 2.95 (t, J=6.4 Hz, 2H), MS (APCI+) m/z 431.0 (M+H)$^+$.

BIOLOGICAL EXAMPLES

List of abbreviations used in the biological examples section: cAMP for cyclic adenosine monophosphate; DMSO for dimethyl sulfoxide; D-PBS for Dulbecco's phosphate buffered saline; and PBS for phosphate buffered saline.
In Vitro Assays
YFP-Halide Influx Assay for the CFTR-ΔF508 Mutation The YFP halide influx assay measured the functionality of the cystic fibrosis Transmembrane Conductance regulator (CFTR) channels in the cystic fibrosis bronchial epithelium cell line CFBE41o-. The assay was used to evaluate the capacity of compounds to increase the open probability of existing CFTR channels in the membrane. It makes use of the observation that the yellow fluorescent protein (YFP) variant YFP H148Q, I152L, F47L has its fluorescence substantially quenched by halide ions like Cl$^-$ and I$^-$ (Galietta, L. J. V., Haggie, P. M., Verkman, A. S., 2001. Green fluorescent protein-based halide indicators with improved chloride and iodide affinities. FEBS Lett. 499, 220-224. doi:10.1016/S0014-5793(01)02561-3; Nagai, T., Ibata, K., Park, E. S., Kubota, M., Mikoshiba, K., Miyawaki, A., 2002. A variant of yellow fluorescent protein with fast and efficient maturation for cell-biological applications. Nat. Biotechnol. 20, 87-90. doi:10.1038/nbt0102-87).

For this purpose, CFBE410-cells were seeded in 384 well plates (3000 CFBE cells/well). One day after seeding, the CFBE cells were transduced with adenoviral vectors that direct the expression of the CFTR ΔF508 mutant and of the YFP reporter. Cells were incubated at 27° C., 5% CO$_2$ for 24 hours so as to allow for the proper folding and migration to the membrane of the CFTR channel or treated with a CFTR modulator during 24 hours at 37° C.

The next day the CFTR channels were activated by treatment with the cAMP inducer forskolin (10.67 µM) and test compound in 1×D-PBS in a total volume of 30 µL (from Gibco, Cat n#14090-041) for 10 minutes prior to addition of 30 µL of following iodide solution (375 mM NaI, 7.5 mM KI, 1.76 mM KH$_2$PO$_4$, 10.1 mM Na$_2$HPO$_4$, 13.75 mM glucose). The I-induced quenching of fluorescence was recorded on an immediately after injection of iodide for 2 minutes on an FDSS/µCell (Hamamatsu). The capacity of a compound to increase the channel opening was directly correlated with the decrease in fluorescence, and was expressed as (1-(fluorescence after 36 seconds (F)/fluorescence before injection (F0))) and an EC$_{50}$ was derived from a (1-F/F0) vs compound concentration plot.

TABLE I

Illustrative EC$_{50}$ measured by YFP-halide influx assay for the CFTR-ΔF508 of the compounds of the invention.

| Compound # | % Activation | EC$_{50}$ (nM) |
|---|---|---|
| 1 | 113.82 | 5.57 |
| 3 | 120.51 | 2.36 |
| 4 | 103.69 | 1.8 |
| 5 | 58.29 | >667 |
| 6 | 86.03 | 78.11 |
| 7 | 109.69 | 5.8 |
| 8 | 93.73 | 299.95 |
| 9 | 104.65 | 96.75 |
| 10 | 106.5 | 14.87 |
| 11 | 109.82 | 35.07 |
| 12 | 100.38 | 8.52 |
| 13 | 100.57 | 327.1 |
| 14 | 116.8 | 67.87 |
| 15 | 113.65 | 6.94 |
| 16 | 110.75 | 78.12 |
| 17 | 117.3 | 11.39 |
| 18 | 106.2 | 9.09 |
| 19 | 97.54 | 349.8 |
| 20 | 97.45 | 8.12 |
| 21 | 109.42 | 8.54 |
| 22 | 112.9 | 15.17 |
| 23 | 100.92 | 37.09 |
| 24 | 100.82 | 13.75 |
| 25 | 104.42 | 4.4 |
| 26 | 101.69 | 3.33 |
| 27 | 96.45 | 150.75 |
| 28 | 50.3 | 1660 |
| 29 | 102.9 | 16.04 |
| 30 | 94.98 | 3.61 |
| 31 | 102.85 | 36.92 |
| 32 | 105.02 | 36.55 |
| 33 | 103.5 | 39.84 |
| 34 | 102.19 | 21.34 |
| 35 | 98.52 | 20.83 |

TABLE I-continued

Illustrative $EC_{50}$ measured by YFP-halide influx assay for the CFTR-ΔF508 of the compounds of the invention.

| Compound # | % Activation | $EC_{50}$ (nM) |
|---|---|---|
| 36 | 102.93 | 12.27 |
| 37 | 119.85 | 28.66 |
| 38 | 109.05 | 223.95 |
| 39 | 119.45 | 9.88 |
| 40 | 106.65 | 36.75 |
| 41 | 96.97 | 41.3 |
| 42 | 109.65 | 1.57 |
| 43 | 110.8 | <0.77 |
| 44 | 105.25 | 1.63 |
| 45 | 109.25 | 1.13 |
| 46 | 82.3 | >1660 |
| 47 | 59.4 | >1660 |
| 48 | 6.28 | >4990 |
| 49 | 29.2 | >3325 |
| 50 | 45.59 | >1660 |
| 51 | 23.23 | >3325 |
| 52 | 3.42 | >4990 |
| 53 | 15.28 | >4990 |
| 54 | 12.02 | >4990 |
| 55 | 2.76 | >4990 |
| 57 | 93.64 | 2.41 |
| 58 | 104.91 | 3.51 |
| 59 | 106.56 | 4.25 |
| 60 | 122.9 | 15.31 |
| 61 | 97.36 | 97.4 |
| 62 | 113 | <0.44 |
| 63 | 109.95 | <0.39 |
| 64 | 122 | <0.46 |
| 65 | 106.55 | <1.05 |
| 66 | <1.18 | 100.47 |

YFP-Halide Influx Assay for the CFTR-G551D Mutation

The YFP halide influx assay measured the functionality of the cystic fibrosis Transmembrane Conductance regulator (CFTR) channels. The assay was used to evaluate the capacity of compounds to increase the channel opening of existing mutant CFTR channels in the membrane. It makes use of the observation that the yellow fluorescent protein (YFP) variant YFP H148Q, I152L, F47L has its fluorescence substantially quenched by halide ions like Cl⁻ and I⁻ (Galietta, L. J. V., Haggie, P. M., Verkman, A. S., 2001. Green fluorescent protein-based halide indicators with improved chloride and iodide affinities. FEBS Lett. 499, 220-224. doi:10.1016/S0014-5793(01)02561-3).

For this purpose, HEK293-cells were seeded in 96 well plates. During seeding, the cells were reverse-transfected with plasmid vectors that direct the expression of the CFTR G551D mutant and of the YFP reporter. Cells were incubated at 37° C., 5% $CO_2$ for 24 hours so as to allow for sufficient expression of the CFTR protein.

The next day the CFTR channels were activated by treatment with the cAMP inducer Forskolin (10.67 μM) and test compound in D-PBS (Gibco) for 10 minutes prior to addition of an I⁻ solution (137 mM NaI, 2.7 mM KI, 1.76 mM $KH_2PO_4$, 10.1 mM $Na_2HPO_4$, 5 mM glucose). The I⁻-induced quenching of fluorescence was recorded immediately after injection of I⁻ for 7 seconds. The capacity of a compound to increase the channel opening was directly correlated with the decrease in fluorescence, and was expressed as (1-(fluorescence after 7 seconds (F)/fluorescence before injection (F0))) and an $EC_{50}$ was derived from a (1-F/F0) vs compound concentration plot.

Similar YHA assays were developed for other channel gating defective or channel conductance defective CFTR mutants to determine effect of compound on channel activity. Examples of mutants are G178R, G1349D, S549N, R117H, R334W. This assay is also used for additional class I CFTR mutants, including G542X, W1282X; class II mutants including N1303K, and for class III mutants including S1251N; or wild-type CFTR.

TABLE II

Illustrative $EC_{50}$ measured by YFP-halide influx assay for the CFTR-G551D of the compounds of the invention.

| Compound # | % Activation | $EC_{50}$ (nM) |
|---|---|---|
| 1 | 37.7 | >10000 |
| 3 | 49.0 | 181 |
| 4 | 34.3 | >6768.2 |
| 5 | 0.3 | >10000 |

TABLE III

Illustrative $EC_{50}$ measured by YFP-halide influx assay for the CFTR-G178R of the compounds of the invention.

| Compound # | % Activation | $EC_{50}$ (nM) |
|---|---|---|
| 1 | 67.2 | 196 |
| 3 | 57.4 | 1440 |

TABLE IV

Illustrative $EC_{50}$ measured by YFP-halide influx assay for the CFTR-G1349D of the compounds of the invention.

| Compound # | % Activation | $EC_{50}$ (nM) |
|---|---|---|
| 1 | 72.8 | 137 |
| 3 | 58.6 | 44.9 |

TABLE V

Illustrative $EC_{50}$ measured by YFP-halide influx assay for the CFTR-S549N of the compounds of the invention.

| Compound # | % Activation | $EC_{50}$ (nM) |
|---|---|---|
| 1 | 75.4 | 275 |
| 3 | 56.3 | 55.9 |

TABLE VI

Illustrative $EC_{50}$ measured by YFP-halide influx assay for the CFTR-R117H of the compounds of the invention.

| Compound # | % Activation | $EC_{50}$ (nM) |
|---|---|---|
| 1 | 88.7 | 184 |
| 3 | 89.0 | 35.5 |

Cellular Assays

Electrophysiological measurements on primary human bronchial epithelial cell cultures are a useful preclinical surrogate of clinical efficacy (Rowe, S. M., Verkman, A. S., 2013. Cystic Fibrosis Transmembrane Regulator Correctors and Potentiators. Cold Spring Harb. Perspect. Med. 3, a009761. doi:10.1101/cshperspect.a009761), therefore compounds are evaluated in an Ussing chamber and/or TECC assay which are electrophysiological measurement assays.

Ussing Chambers Assay
Protocol

The Ussing chambers assay measures the functionality of the cystic fibrosis Transmembrane Conductance regulator (CFTR) by measuring the short circuit current ($I_{SC}$) generated over the basolateral and apical membrane of lung epithelial cells.

In order to measure the $I_{SC}$, the epithelium is short circuited by injecting a current that is adjusted by a feedback amplifier to keep the transepithelial potential ($V_t$) at 0 mV. The amount of current required is adjusted by a feedback circuit and continuously measured. Intermittently the voltage is clamped to values different from 0 mV thus enabling an estimate of the transepithelial resistance ($R_t$).

For this purpose, bronchial epithelial cells isolated from CF patients homozygous for the CFTR ΔF508 mutation (hAEC-CF, Epithelix) or heterozygous for CFTR G551D and ΔF508 mutations (University of North Carolina, Chapel Hill) are plated on type IV collagen-coated Snapwell™ supports (Corning-Costar). Human airway epithelia are generated by provision of an airliquid interface for 21 days to form well-differentiated polarized cultures that resemble in vivo pseudo-stratified ciliated epithelium (Fulcher, M. L., Gabriel, S., Burns, K. A., Yankaskas, J. R., Randell, S. H., 2005. Well-differentiated human airway epithelial cell cultures. Methods Mol. Med. 107, 183-206). In the case of the homozygous ΔF508 CFTR samples, the differentiated cells are treated with 3 µM VX809 (2626 South Loop West, Suite 225, Houston, Tex. 77054 USA, Cat n# S1565) to allow sufficient expression of properly folded CFTR protein on the membrane (48 hours basolateral treatment and 24 hours apical treatment), prior to electrophysiological recordings. For heterozygous G551D/ΔF508, differentiated cells are used as such for the recordings.

For electrophysiological recording, the human airway epithelia are mounted in Ussing chambers for measurement of short-circuit current ($I_{SC}$). The epithelia are bathed in a NaCl-Ringer solution (120 mM NaCl, 25 mM $NaHCO_3$, 1.2 mM $CaCl_2$, 1.2 mM $MgCl_2$, 0.8 mM $KH_2PO_4$, 0.8 mM $K_2HPO_4$, pH 7.4, 5 mM glucose) on the basolateral side and a glutamate-ringer solution (120 mM sodium glutamate, 25 mM $NaHCO_3$, 1.2 mM $CaCl_2$, 1.2 mM $MgCl_2$, 0.8 mM $KH_2PO_4$, 0.8 mM $K_2HPO_4$, pH 7.4, 5 mM glucose) on the apical side to generate a Cl⁻ gradient. Both chambers are gassed with 95% $O_2$, 5% $CO_2$, and maintained at 27° C. Apical amiloride is used to inhibit the endogenous ENaC currents while Forskolin is applied on both apical and basolateral side to stimulate CFTR. After Forskolin triggering, compounds are added on both side to test their potential for increasing CFTR gating. The increase in $I_{SC}$ is used as a measure for the increased CFTR activity, $EC_{50}$ values can be generated by measuring impact of different concentrations of compound on Short circuit current on primary cells, for this purpose the same Snapwell™ is used for the addition of increasing amounts of compound and the increase in $I_{sc}$ signal at each step is then transformed into a dose response curve. Inh-172, an inhibitor specific for CFTR, is used to test the specificity of the tested compounds.

TECC Assay
Primary Bronchial Epithelial Cells Protocol

The TECC (Transepithelial Clamp Circuit, EP-design) assay measures the functionality of the cystic fibrosis Transmembrane Conductance regulator (CFTR) by measuring the short circuit current ($I_{SC}$) generated over the basolateral and apical membrane of lung epithelial cells. In TECC the transepithelial potential PD and transepithelial resistance ($R_t$) are measured in an open circuit and transformed to $I_{SC}$ using Ohm's law. 24 Wells can be measured simultaneously allowing a higher throughput compared to Ussing chambers.

For this purpose, bronchial epithelial cells isolated from CF patients homozygous for the CFTR ΔF508 mutation (hAEC-CF, McGill, UNC) are plated on type IV collagen-coated Transwell® supports (Costar). Human airway epithelia are generated by provision of an air liquid interface for 21 days to form well-differentiated polarized cultures that resemble in vivo pseudo-stratified ciliated epithelium (Fulcher, M. L., Gabriel, S., Burns, K. A., Yankaskas, J. R., Randell, S. H., 2005. Well-differentiated human airway epithelial cell cultures. Methods Mol. Med. 107, 183-206). In the case of the homozygous ΔF508 CFTR samples, the differentiated cells are treated with 3 µM VX809 (2626 South Loop West, Suite 225, Houston, Tex. 77054 USA, Cat n# S1565) or 0.15 µM GLPG2222 to allow sufficient expression of properly folded CFTR protein on the membrane (48 hours basolateral treatment and 24 hours apical treatment), prior to electrophysiological recordings.

Information on the compounds can be retrieved on the homozygous ΔF508 CFTR samples looking at increased CFTR activity when compounds are added in an acute mode or in a chronic mode.

For the acute mode, for electrophysiological recording, the human airway epithelia are mounted in the TECC heating plate for electrophysiological measurement and kept at 37° C. The epithelia are bathed in a NaCl-Ringer solution (120 mM NaCl, 25 mM $NaHCO_3$, 1.2 mM $CaCl_2$, 1.2 mM $MgCl_2$, 0.8 mM $KH_2PO_4$, 0.8 mM $K_2HPO_4$, pH 7.4, 5 mM glucose) on both the basolateral and apical sides. Apical amiloride is used to inhibit the endogenous ENaC currents while Forskolin is applied on both apical and basolateral side to stimulate CFTR. After Forskolin triggering, compounds are added on both sides to test their potential for increasing CFTR gating. Measurements are done during a 20 minute timeframe with recordings every 2 minutes. The increase in $I_{SC}$ is used as a measure for the increased CFTR activity, $EC_{50}$ values can be generated by measuring impact of different concentrations of compound on $I_{SC}$ on primary cells, for this purpose each transwell is treated with a different compound concentration. Inh-172, an inhibitor specific for CFTR, is used to test the specificity of the tested compounds.

Similar TECC recordings are performed using primary cells for other channel gating defective or channel conductance defective CFTR mutants to determine effect of compound on channel activity. Examples of mutants include R117H, G178R. Similarly primary cells containing class I CFTR mutants, including G542X, W1282X; and additional class II mutants including N1303K can be used for electrophysiological recordings.

Results

When subjected to this protocol, the following values were obtained. The difference between ΔIsc measured as DMSO (baseline), and the ΔIsc measured with the compound tested.

CFTR ΔF508 TECC Assay $EC_{50}$ Measurements

TABLE VII

TECC assay in CFTR ΔF508 $EC_{50}$ for illustrative compounds of the invention.

| Compound # | $EC_{50}$ (nM) |
| --- | --- |
| 1 | 40 |
| 4 | 6 |

The data provided in the present application demonstrate that the compounds of the invention demonstrate activity in vitro, and may be useful in vivo in the treatment of cystic fibrosis.

Further benefits of Applicants' invention will be apparent to one skilled in the art from reading this patent application.

It is understood that the foregoing detailed description and accompanying examples are merely illustrative and are not to be taken as limitations upon the scope of the invention, which is defined solely by the appended claims and their equivalents. Various changes and modifications to the embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

What is claimed is:
1. A compound of Formula I, or a pharmaceutically acceptable salt thereof,

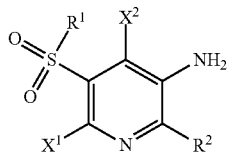

I wherein
$X^1$ and $X^2$ are independently selected
H;
halo;
$C_{1-4}$ alkyl optionally substituted with one or more independently selected halo;
$C_{1-4}$ alkoxy optionally substituted with one or more independently selected
—OH;
$C_{1-4}$ alkoxy; or
—NR$^{8A}$R$^{8B}$;
—NR$^{9A}$R$^{8B}$;
cyclopropyl optionally substituted with one or more independently selected $R^5$ groups;
phenoxy optionally substituted with one or more independently selected $R^5$ groups; or
phenyl optionally substituted with one or more independently selected $R^5$ groups;
$R^1$ is
$C_{1-4}$ alkyl optionally substituted with one or more independently selected
—OH;
$C_{1-4}$ alkoxy; or
4-6 membered monocyclic heterocycle comprising 1 or 2 heteroatoms independently selected from the group consisting of O, S, and N;
phenyl optionally substituted with one or more independently selected $R^4$ groups;
N-linked 4-6 membered monocyclic heterocycle comprising 1, 2, or 3 heteroatoms independently selected from the group consisting of N, O, and S, wherein the monocyclic heterocycle is optionally substituted with one or more independently selected $R^5$ groups;
N-linked 4-6 membered monocyclic heterocycle comprising 1, 2, or 3 heteroatoms independently selected from the group consisting of N, O, and S, fused to a phenyl, wherein the monocyclic heterocycle and the phenyl are optionally substituted with one or more independently selected $R^5$ groups;
$C_{3-7}$ cycloalkyl optionally substituted with one or more independently selected $R^5$ groups; or
—NR$^6$R$^7$;
$R^2$ is 5-6 membered monocyclic heteroaryl comprising 1, 2, or 3 heteroatoms independently selected from the group consisting of O, S, and N, wherein the monocyclic heteroaryl is optionally substituted with one or more independently selected $R^3$ groups;
each $R^3$ is independently selected from the group consisting of:
$C_{1-4}$ alkyl optionally substituted with one or more independently selected
$C_{3-7}$ cycloalkyl; wherein the $C_{3-7}$ cycloalkyl is optionally substituted with one or more independently selected $R^4$ groups;
4-6 membered monocyclic heterocycle comprising 1 or 2 heteroatoms independently selected from the group consisting of O, S, and N; wherein the monocyclic heterocycle is optionally substituted with one or more independently selected $R^4$ groups;
phenyl; wherein the phenyl is optionally substituted with one or more independently selected $R^4$ groups;
$C_{1-4}$ alkoxy optionally substituted with one or more independently selected C3-7 cycloalkyl, halo, or —OCH$_3$;
—OR$^{11}$
—OH;
halo;
—CN;
—OC(O)R$^{10}$;
—OS(O)$_2$OH;
—NHC(=S)R$^{11}$; or
—OP(O)(OH)(OH);
—C(O)NH$_2$;
phenyl; wherein the phenyl is optionally substituted with one or more independently selected $R^4$ groups;
5-6 membered monocyclic heteroaryl comprising 1, 2, or 3 heteroatoms independently selected from the group consisting of O, S, and N; wherein the monocyclic heteroaryl is optionally substituted with one or more independently selected $R^4$ groups;
$C_{3-7}$ cycloalkyl; wherein the $C_{3-7}$ cycloalkyl is optionally substituted with one or more independently selected $R^4$ groups; and
4-6 membered monocyclic heterocycle comprising 1 or 2 heteroatoms independently selected from the group consisting of O, S, and N; wherein the monocyclic heterocycle is optionally substituted with one or more independently selected $R^4$ groups;
each $R^4$ is independently selected from the group consisting of:
halo;
$C_{1-4}$ alkyl optionally substituted with one or more independently selected halo; and
$C_{1-4}$ alkoxy optionally substituted with one or more independently selected halo;
each $R^5$ is independently selected from the group consisting of:
—OH;
halo;
$C_{1-4}$ alkyl optionally substituted with one or more independently selected $C_{1-4}$ alkoxy, halo or —OH; and
$C_{1-4}$ alkoxy optionally substituted with one or more independently selected halo;

R⁶ is H, $C_{3-7}$ alkyl, or $C_{3-7}$ cycloalkyl wherein the $C_{3-7}$ cycloalkyl is optionally substituted with one or more independently selected R⁵ groups;

R⁷ is
  $C_{1-4}$ alkyl optionally substituted with one or more independently selected halo;
  phenyl optionally substituted with one or more independently selected halo;
    $C_{1-4}$ alkyl optionally substituted with one or more independently selected halo; or
    $C_{1-4}$ alkoxy optionally substituted with one or more independently selected halo;
  $C_{1-4}$ alkoxy optionally substituted with one or more independently selected halo; or
  4-6 membered monocyclic heterocycle comprising 1 or 2 heteroatoms independently selected from the group consisting of O, S, and N; wherein the monocyclic heterocycle is optionally substituted with one or more independently selected R⁵ groups;

each $R^{8a}$ and $R^{8b}$ is independently selected from the group consisting of
  H; and
  $C_{1-4}$ alkyl;

$R^{9a}$ and $R^{9b}$ are independently selected from the group consisting of
  H;
  $C_{1-4}$ alkyl; and
  $C_{3-7}$ cycloalkyl; and each $R^{10}$ is independently selected from the group consisting of
  $C_{1-6}$ alkyl; and
  phenyl; wherein phenyl is optionally substituted with one or more independently selected $R^A$ groups;

each $R^{11}$ is independently selected from the group consisting of
  4-6 membered monocyclic heterocycle comprising 1 or 2 heteroatoms independently selected from the group consisting of O, S, and N; wherein the monocyclic heterocycle is optionally substituted with one or more independently selected $R^A$ groups;
  5-6 membered monocyclic heteroaryl comprising 1, 2, or 3 heteroatoms independently selected from the group consisting of O, S, and N; wherein the monocyclic heteroaryl is optionally substituted with one or more independently selected $R^A$ groups;
  $C_{3-7}$ cycloalkyl; wherein the $C_{3-7}$ cycloalkyl is optionally substituted with one or more independently selected $R^A$ groups; and
  phenyl; wherein phenyl is optionally substituted with one or more independently selected $R^A$ groups; and each $R^A$ is independently selected from the group consisting of
  —CN,
  halo;
  $C_{1-4}$ alkyl optionally substituted with one or more independently selected halo; and
  $C_{1-4}$ alkoxy optionally substituted with one or more independently selected halo.

2. The compound of claim 1, or a pharmaceutically acceptable salt thereof, wherein
  R¹ is phenyl optionally substituted with one independently selected $R^A$ group.

3. The compound of claim 1, or a pharmaceutically acceptable salt thereof, wherein
  R¹ is phenyl substituted with one —OCF₃.

4. The compound of claim 1, or a pharmaceutically acceptable salt thereof, wherein X¹ and X² are each H.

5. The compound of claim 1, or a pharmaceutically acceptable salt thereof, wherein R² is 5-6 membered monocyclic heteroaryl comprising 1, 2, or 3 heteroatoms independently selected from the group consisting of O, S, and N, wherein the monocyclic heteroaryl is optionally substituted with one R³ group.

6. The compound of claim 1, or a pharmaceutically acceptable salt thereof, wherein R² is 1,3,4-oxadiazolyl, 1,2,4-oxadiazolyl, 1,3,4-thiadiazolyl, or thiazolyl wherein the 1,3,4-oxadiazolyl, 1,2,4-oxadiazolyl, 1,3,4-thiadiazolyl, and thiazolyl are substituted with one independently selected R³.

7. The compound of claim 5, or a pharmaceutically acceptable salt thereof, wherein R³ is $C_{1-4}$ alkyl optionally substituted with one or more independently selected
  —OH;
  halo; or
  —OP(O)(OH)(OH).

8. The compound of claim 6, or a pharmaceutically acceptable salt thereof, wherein R³ is $C_{1-4}$ alkyl optionally substituted with one or more independently selected
  —OH;
  halo; or
  —OP(O)(OH)(OH).

9. The compound of claim 1 of Formula I-a, or a pharmaceutically acceptable salt thereof,

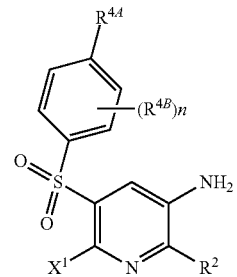

I-a wherein
  n is 0, 1, or 2;
  $R^{4A}$ is H, F, —CH₃,—CH(CH₃)₂, t-Bu, CF₃,—OCH₃, —OCH(CH₃)₂, or —OCF₃;
  each $R^{4B}$ is independently F or —OCF₃; and
  X¹ and R² are as set forth in claim 1.

10. The compound of claim 9, or a pharmaceutically acceptable salt thereof, wherein X¹ is H.

11. The compound of claim 9, or a pharmaceutically acceptable salt thereof, wherein
  n is 0; and
  $R^{4A}$ is —OCF₃.

12. The compound of claim 9, or a pharmaceutically acceptable salt thereof, wherein
  X¹ is H;
  n is 0;
  $R^{4A}$ is —OCF₃;
  R² is 1,3,4-oxadiazolyl or thiazolyl substituted with one R³; and
  R³ is $C_{1-4}$ alkyl optionally substituted with one or more independently selected
    —OH;
    halo; or
    —OP(O)(OH)(OH).

13. The compound of claim 1, or a pharmaceutically acceptable salt thereof, wherein the compound is selected from the group consisting of:

(5{3-amino-5-[4-(trifluoromethoxy)benzene-1-sulfonyl]pyridin-2-yl}-1,3,4-oxadiazol-2-yl)methanol;

(5{3-amino-5-[4-(trifluoromethoxy)benzene-1-sulfonyl]pyridin-2-yl}-1,3,4-oxadiazol-2-yl)methyldihydrogenphosphate;

2-(5-{3-amino-5-[4-(trifluoromethoxy)benzene-1-sulfonyl]pyridin-2-yl}-1,3,4-oxadiazol-2-yl)-1,1,1-trifluoropropan-2-ol;

1-(5-{3-amino-5-[4-(trifluoromethoxy)benzene-1-sulfonyl]pyridin-2-yl}-1,3,4-oxadiazol-2-yl)-2,2,2-trifluoroethan-1-ol;

(2-{3-amino-5-[4-(trifluoromethoxy)benzene-1-sulfonyl]pyridin-2-yl-}1,3-thiazol-5-yl)methanol;

2-(-1,3,4-oxadiazol-2-yl)-5-[4-(trifluoromethoxy)benzene-1-sulfonyl]pyridin-3-amine;

(5{3-amino-5-[4-(trifluoromethoxy)benzene-1-sulfonyl]pyridin-2-yl}-1,3,4-oxadiazol-2-yl)methanol;

(5{3-amino-5-[4-(trifluoromethoxy)benzene-1-sulfonyl]pyridin-2-yl}-1,3,4-oxadiazole-2-carboxamide;

{5[3-amino-5-(4-fluorobenzene-1-sulfonyl)pyridin-2-yl]-1,3,4-oxadiazol-2-yl}methanol;

2-(5-cyclohexyl-1,3,4-oxadiazol-2-yl)-5-[4(trifluoromethoxy)benzene-1-sulfonyl]pyridin-3-amine;

2-{5-[(S)-methoxy(phenyl)methyl]-1,3,4-oxadiazol-2-yl}-5-[4-(trifluoromethoxy)benzene-1-sulfonyl]pyridin-3-amine;

2-{5-[(cyclopropylmethoxy)methyl]-1,3,4-oxadiazol-2-yl}-5-[4-(trifluoromethoxy)benzene-1-sulfonyl]pyridin-3-amine;

2-[5-(phenoxymethyl)-1,3,4-oxadiazol-2-yl]-5-[4-(trifluoromethoxy)benzene-1-sulfonyl]pyridin-3-amine;

2-{5-[(cyclopentyloxy)methyl]-1,3,4-oxadiazol-2-yl}-5-[4-(trifluoromethoxy)benzene-1-sulfonyl]pyridin-3-amine;

5-[4-(trifluoromethoxy)benzene-1-sulfonyl]-2-{5-[(trifluoromethoxy)methyl]-1,3,4-oxadiazol-2-yl}pyridin-3-amine;

2-(5-{[(oxolan-3-yl)oxy]methyl}1,3,4-oxadiazol-2-yl)-5-[4-(trifluoromethoxy)benzene-1-sulfonyl]pyridin-3-amine;

2-{-[(2-methoxyethoxy)methyl]-1,3,4-thiadiazol-2-yl}-5-[4-(trifluoromethoxy)benzene-1-sulfonyl]pyridin-3-amine;

N-[(5-{3-amino-5-[4-(trifluoromethoxy)benzene-1-sulfonyl]pyridin-2-yl}-1,3,4-thiadiazol-2-yl)methyl]cyclopropanecarbothioamide;

2-{5-[(S)-methoxy(phenyl)methyl]-1,3,4-thiadiazol-2-yl}-5-[4-(trifluoromethoxy)benzene-1-sulfonyl]pyridin-3-amine;

(2S)-2-(5-{3-amino-5-[4-(trifluoromethoxy)benzene-1-sulfonyl]pyridin-2-yl}-1,3,4-thiadiazol-2-yl)-1,1,1-trifluoropropan-2-ol;

2-{5-[(1R)-1-methoxyethyl]-1,3,4-thiadiazol-2-yl}-5-[4-(trifluoromethoxy)benzene-1-sulfonyl]pyridin-3-amine;

2-[5-(1-methoxyethyl)-1,3,4-thiadiazol-2-yl]-5-[4-(trifluoromethoxy)benzene-1-sulfonyl]pyridin-3-amine;

2-{5-[(1S)-1-methoxyethyl]-1,3,4-thiadiazol-2-yl}-5-[4-(trifluoromethoxy)benzene-1-sulfonyl]pyridin-3-amine;

2-{5-[(cyclopropylmethoxy)methyl]-1,3,4-thiadiazol-2-yl}-5-[4-(trifluoromethoxy)benzene-1-sulfonyl]pyridin-3-amine;

2-[5-(ethoxymethyl)-1,3,4-thiadiazol-2-yl]-5-[4-(trifluoromethoxy)benzene-1-sulfonyl]pyridin-3-amine;

2-[5-(methoxymethyl)-1,3,4-thiadiazol-2-yl]-5-[4-(trifluoromethoxy)benzene-1-sulfonyl]pyridin-3-amine;

2-(5-{[(pyridin-3-yl)oxy]methyl}-1,3,4-thiadiazol-2-yl)-5-[4-(trifluoromethoxy)benzene-1-sulfonyl]pyridin-3-amine;

5-[4-(trifluoromethoxy)benzene-1-sulfonyl]-2-{5-[(trifluoromethoxy)methyl]-1,3,4-thiadiazol-2-yl}pyridin-3-amine;

2-(5-{[(oxolan-3-yl)oxy]methyl}-1,3,4-thiadiazol-2-yl)-5-[4-(trifluoromethoxy)benzene-1-sulfonyl]pyridin-3-amine;

2-{5-[(difluoromethoxy)methyl]-1,3,4-thiadiazol-2-yl}-5-[4-(trifluoromethoxy)benzene-1-sulfonyl]pyridin-3-amine;

2-(5-{[(2S)-oxolan-2-yl]methyl}-1,3,4-thiadiazol-2-yl)-5-[4-(trifluoromethoxy)benzene-1-sulfonyl]pyridin-3-amine;

2-(5-{[(2R)-oxolan-2-yl]methyl}-1,3,4-thiadiazol-2-yl)-5-[4-(trifluoromethoxy)benzene-1-sulfonyl]pyridin-3-amine;

2-{5-[(2-methoxyethoxy)methyl]-1,3,4-oxadiazol-2-yl}-5-[4-(trifluoromethoxy)benzene-1-sulfonyl]pyridin-3-amine;

2-{5-[(1R)-1-methoxyethyl]-1,3,4-oxadiazol-2-yl}-5-[4-(trifluoromethoxy)benzene-1-sulfonyl]pyridin-3-amine;

2-{5-[(1S)-1-methoxyethyl]-1,3,4-oxadiazol-2-yl}-5-[4-(trifluoromethoxy)benzene-1-sulfonyl]pyridin-3-amine;

2-[5-(ethoxymethyl)-1,3,4-oxadiazol-2-yl]-5-[4-(trifluoromethoxy)benzene-1-sulfonyl]pyridin-3-amine;

2-[5-(methoxymethyl)-1,3,4-oxadiazol-2-yl]-5-[4-(trifluoromethoxy)benzene-1-sulfonyl]pyridin-3-amine;

2-(5-{-[(pyridin-3-yl)oxy]methyl}-1,3,4-oxadiazol-2-yl)-5-[4-(trifluoromethoxy)benzene-1-sulfonyl]pyridin-3-amine;

2-{5-[(difluoromethoxy)methyl]-1,3,4-oxadiazol-2-yl}-5-[4-(trifluoromethoxy)benzene-1-sulfonyl]pyridin-3-amine;

2-(5-{[(2S)-oxolan-2-yl]methyl}-1,3,4-oxadiazol-2-yl)-5[4-(trifluoromethoxy)benzene-1-sulfonyl]pyridin-3-amine;

2-(5-{[(2R)-oxolan-2-yl]methyl}-1,3,4-oxadiazol-2-yl)-5-[4-(trifluoromethoxy)benzene-1-sulfonyl]pyridin-3-amine;

1-(5-{3-amino-5-[4-(trifluoromethoxy)benzene-1-sulfonyl]pyridin-2-yl}-1,3,4-oxadiazol-2-yl)ethan-1-ol;

2-(5-{3-amino-5-[4-(trifluoromethoxy)benzene-1-sulfonyl]pyridin-2-yl}-1,3,4-oxadiazol-2-yl)propan-2-ol;

(1S)-1-(5-{3-amino-5-[4-(trifluoromethoxy)benzene-1-sulfonyl]pyridin-2-yl}-1,3,4-oxadiazol-2-yl)-2-phenylethan-1-ol;

(S)-(5-{3-amino-5-[4-(trifluoromethoxy)benzene-1-sulfonyl]pyridin-2-yl}-1,3,4-oxadiazol-2-yl)(phenyl)methanol;

2-[3-(2-methoxypropan-2-yl)-1,2,4-oxadiazol-5-yl]-5-[4-(trifluoromethoxy)benzene-1-sulfonyl]pyridin-3-amine;

2-[3-(1-methoxyethyl)-1,2,4-oxadiazol-5-yl]-5-[4-(trifluoromethoxy)benzene-1-sulfonyl]pyridin-3-amine;

2-[3-(oxan-4-yl)-1,2,4-oxadiazol-5-yl]-5-[4-(trifluoromethoxy)benzene-1-sulfonyl]pyridin-3-amine;

2-{3-[(4-fluorophenoxy)methyl]-1,2,4-oxadiazol-5-yl}-5-[4-(trifluoromethoxy)benzene-1-sulfonyl]pyridin-3-amine;

2-[3-(cyclopropylmethyl)-1,2,4-oxadiazol-5-yl]-5-[4-(trifluoromethoxy)benzene-1-sulfonyl]pyridin-3-amine;
2-{3-[(oxolan-2-yl)methyl]-1,2,4-oxadiazol-5-yl}-5-[4-(trifluoromethoxy)benzene-1-sulfonyl]pyridin-3-amine;
2-(3-cyclopropyl-1,2,4-oxadiazol-5-yl)-5-[4-(trifluoromethoxy)benzene-1-sulfonyl]pyridin-3-amine;
2-[3-(oxolan-3-yl)-1,2,4-oxadiazol-5-yl]-5-[4-(trifluoromethoxy)benzene-1-sulfonyl]pyridin-3-amine;
2-(3-tert-butyl-1,2,4-oxadiazol-5-yl)-5-[4-(trifluoromethoxy)benzene-1-sulfonyl]pyridin-3-amine;
2-[3-(2-methoxyethyl)-1,2,4-oxadiazol-5-yl]-5-[4-(trifluoromethoxy)benzene-1-sulfonyl]pyridin-3-amine;
2-[3-(methoxymethyl)-1,2,4-oxadiazol-5-yl]-5-[4-(trifluoromethoxy)benzene-1-sulfonyl]pyridin-3-amine;
(5-{3-amino-4-chloro-5-[4-(trifluoromethoxy)benzene-1-sulfonyl]pyridin-2-yl}-1,3,4-oxadiazol-2-yl)methanol;
(5-{3-amino-5-[3-(trifluoromethoxy)benzene-1-sulfonyl]pyridin-2-yl}-1,3,4-oxadiazol-2-yl)methanol;
(5-{3-amino-5-[2-(trifluoromethoxy)benzene-1-sulfonyl]pyridin-2-yl}-1,3,4-oxadiazol-2-yl)methanol;
5-amino-N-benzyl-6-[5-(hydroxymethyl)-1,3,4-oxadiazol-2-yl]-N-methylpyridine-3-sulfonamide;
{5-[3-amino-5-(benzenesulfonyl)pyridin-2-yl]-1,3,4-oxadiazol-2-yl}methanol;
(5-{3-amino-5-[4-(trifluoromethyl)benzene-1-sulfonyl]pyridin-2-yl}-1,3,4-thiadiazol-2-yl)methanol;
(5-{3-amino-6-bromo-5-[4-(trifluoromethoxy)benzene-1-sulfonyl]pyridin-2-yl}-1,3,4-oxadiazol-2-yl)methanol;
(5-{3-amino-6-chloro-5-[4-(trifluoromethoxy)benzene-1-sulfonyl]pyridin-2-yl}-1,3,4-oxadiazol-2-yl)methanol;
(5-{3-amino-5-[2-(propan-2-yl)benzene-1-sulfonyl]pyridin-2-yl}-1,3,4-oxadiazol-2-yl)methanol;
(5-{3-amino-4-bromo-5-[4-(trifluoromethoxy)benzene-1-sulfonyl]pyridin-2-yl}-1,3,4-oxadiazol-2-yl)methanol; and
2(5-{3-amino-5-[4-(trifluoromethoxy)benzene-1-sulfonyl]pyridin-2-yl}-1,2,4-oxadiazol-3-yl)ethan-1-ol.

14. A pharmaceutical composition comprising a therapeutically effective amount of a compound of claim 1, or a pharmaceutically acceptable salt thereof, in combination with a pharmaceutically acceptable carrier.

15. A compound of claim 1, or a pharmaceutically acceptable salt thereof, or a pharmaceutical composition of claim 14, for use in medicine.

16. A compound of claim 1, or a pharmaceutically acceptable salt thereof, or a pharmaceutical composition of claim 14, for use in the treatment of cystic fibrosis.

17. A method for treating cystic fibrosis in a subject comprising administering a therapeutically effective amount of a compound of claim 1, or a pharmaceutically acceptable salt thereof, to a subject in need thereof.

18. A pharmaceutical composition comprising a compound of claim 1, or a pharmaceutically acceptable salt thereof, and one or more correctors.

19. A method for treating cystic fibrosis in a subject comprising administering a compound of claim 1, or a pharmaceutically acceptable salt thereof, and one or more correctors, to a subject in need thereof.

20. A pharmaceutical composition comprising a compound of claim 1, or a pharmaceutically acceptable salt thereof, and one or more additional therapeutic agents.

21. The pharmaceutical composition of claim 20 wherein the additional therapeutic agents are selected from the group consisting of CFTR modulators and CFTR amplifiers.

22. The pharmaceutical composition of claim 20 wherein the additional therapeutic agents are CFTR modulators.

23. A method for treating cystic fibrosis in a subject comprising administering a compound of claim 1, or a pharmaceutically acceptable salt thereof, and one or more additional therapeutic agents.

24. The method of claim 23 wherein the additional therapeutic agents are selected from the group consisting of CFTR modulators and CFTR amplifiers.

25. The method of claim 23 the wherein the additional therapeutic agents are CFTR modulators.

26. The method of claim 23, wherein the additional therapeutic agents are CFTR correctors.

27. The method of claim 23, wherein the compound of claim 1, or a pharmaceutically acceptable salt thereof, is administered with one CFTR corrector.

28. The method of claim 23, wherein the compound of claim 1, or a pharmaceutically acceptable salt thereof, is administered with two CFTR correctors.

29. (5-{3-amino-5-[4-(trifluoromethoxy)benzene-1-sulfonyl]pyridin-2-yl}-1,3,4-oxadiazol-2-yl)methanol, a pharmaceutically acceptable salt thereof.

* * * * *

UNITED STATES PATENT AND TRADEMARK OFFICE
CERTIFICATE OF CORRECTION

PATENT NO. : 10,138,227 B2
APPLICATION NO. : 15/602892
DATED : November 27, 2018
INVENTOR(S) : Altenbach et al.

It is certified that error appears in the above-identified patent and that said Letters Patent is hereby corrected as shown below:

In the Specification

Column 10, Line 63, "$^{35}$ s" should be --$^{35}$S--

Column 32, Line 29, "2-{5[(S)..." should be --2-{5[($S$)...--

Column 32, Line 48, "N-[(5-..." should be --$N$-[(5-...--

Column 32, Line 51, "2-{5[(S)..." should be --2-{5[($S$)...--

Column 32, Line 54, "(2S)-2-..." should be --(2$S$)-2...--

Column 32, Line 57, "2-{5-[(1R)..." should be --2-{5-[(1$R$)...--

Column 32, Line 61, "2-{5-[(1 S)..." should be --2-{5-[(1$S$)...--

Column 33, Line 16, "2-(5-{[(2S)..." should be --2-(5-{[(2$S$)...--

Column 33, Line 19, "2-(5-{[(2R)..." should be --2-(5-{[(2$R$)...--

Column 33, Line 25, "2-{5-[(1R)..." should be --2-{5-[(1$R$)...--

Column 33, Line 27, "2-{5-[(1 S)..." should be --2-{5-[(1$S$)...--

Column 33, Line 39, "2-(5-{[(2S)..." should be --2-(5-{[(2$S$)...--

Column 33, Line 42, "2-(5-{[(2R)..." should be --2-(5-{[(2$R$)...--

Column 33, Line 49, "(1S)-1-..." should be --(1$S$)-1-...--

Signed and Sealed this
Fifteenth Day of October, 2019

Andrei Iancu
*Director of the United States Patent and Trademark Office*

Column 33, Line 52, "(S)-(5-..." should be --(-$S$)-(5-...--

Column 34, Line 40, ""R" or "S"" should be --"$R$" or "$S$"--

Column 34, Line 41, ""R"" should be --"$R$"--

Column 34, Line 42, ""S"" should be --"$S$"--

Column 34, Line 65, "cis or trans" should be --*cis* or *trans*--

Column 34, Line 67, "(cis)" should be --(*cis*)--

Column 35, Line 2, "(trans)" should be --(*trans*)--

Column 35, Line 3, "cis or trans" should be --*cis* or *trans*--

Column 35, Line 4, "cis and trans" should be --*cis* and *trans*--

Column 35, Line 9, "cis and trans" should be --*cis* and *trans*--

In the Claims

Column 97, Line 1, Claim 1, "$C_{3-7}$ alkyl" should be --$C_{1-4}$ alkyl--

Column 99, Line 28, Claim 13, "2-{5[(S)..." should be --2-{5[($S$)...--

Column 99, Line 45, Claim 13, "2-{-[(2-methyoxyethoxy)methyl]-1, 3, 4 thiadiozol-2-yl}" should be --2-{5-[(2-methyoxyethoxy)methyl]-1, 3, 4-thiadiozol-2-yl}--

Column 99, Line 48, Claim 13, "N-[(5-..." should be --$N$-[(5-...--

Column 99, Line 51, Claim 13, "2-{5[(S)..." should be --2-{5[($S$)...--

Column 99, Line 54, Claim 13, "(2S)-2-..." should be --(2$S$)-2...--

Column 99, Line 57, Claim 13, "2-{5-[(1R)..." should be --2-{5-[(1$R$)...--

Column 99, Line 62, Claim 13, "2-{5-[(1S)..." should be --2-{5-[(1$S$)...--

Column 100, Line 17, Claim 13, "2-(5-{[(2S)..." should be --2-(5-{[(2$S$)...--

Column 100, Line 20, Claim 13, "2-(5-{[(2R)..." should be --2-(5-{[(2$R$)...--

Column 100, Line 26, Claim 13, "2-{5-[(1R)..." should be --2-{5-[(1$R$)...--

Column 100, Line 29, Claim 13, "2-{5-[(1S)..." should be --2-{5-[(1$S$)...--

Column 100, Line 36, Claim 13, "2-(5{-[(pyridin-3-yl)oxy]methyl}" should be --2-(5-{[(pyridin-3-yl)oxy]methyl}--

Column 100, Line 42, Claim 13, "2-(5-{[(2S)..." should be --2-(5-{[(2$S$)...--

Column 100, Line 45, Claim 13, "2-(5-{[(2R)..." should be --2-(5-{[(2$R$)...--

Column 100, Line 52, Claim 13, "(1S)-1-..." should be --(1$S$)-1-...--

Column 100, Line 55, Claim 13, "(S)-(5-..." should be --($S$)-(5-...--

Column 101, Line 10, Claim 13, "2-(3-tert-butyl..." should be --2-(3-*tert*-butyl...--

Column 101, Lines 21-22, Claim 13, "5-amino-N-benzyl-6-[5-(hydroxymethyl)-1,3,4-oxadiazol-2-y-yl]-N-methylpyridine-3-sulfonamide" should be --5-amino-*N*-benzyl-6-[5-(hydroxymethyl)-1,3,4-oxadiazol-2-y-yl]-*N*-methylpyridine-3-sulfonamide--

UNITED STATES PATENT AND TRADEMARK OFFICE
CERTIFICATE OF CORRECTION

PATENT NO. : 10,138,227 B2
APPLICATION NO. : 15/602892
DATED : November 27, 2018
INVENTOR(S) : Altenbach et al.

Page 1 of 1

It is certified that error appears in the above-identified patent and that said Letters Patent is hereby corrected as shown below:

In the Claims

In Claim 29 please add "or" so the claim reads: (5-{3-amino-5-[4-(trifluoromethoxy)benzene-1-sulfonyl] pyridin-2-yl}-1,3,4-oxadiazol-2-yl)methanol, or a pharmaceutically acceptable salt thereof.

Signed and Sealed this
Second Day of June, 2020

Andrei Iancu
*Director of the United States Patent and Trademark Office*